United States Patent
Flygare et al.

(10) Patent No.: US 11,335,436 B2
(45) Date of Patent: May 17, 2022

(54) METHODS AND SYSTEMS FOR MULTIPLE TAXONOMIC CLASSIFICATION

(71) Applicant: University of Utah Research Foundation, Salt Lake City, UT (US)

(72) Inventors: Steven Flygare, Salt Lake City, UT (US); Keith Simmon, Salt Lake City, UT (US); Chase Miller, Salt Lake City, UT (US); Yi Qiao, Salt Lake City, UT (US); Karen Eilbeck, Salt Lake City, UT (US); Gabor Marth, Salt Lake City, UT (US); Mark Yandell, Salt Lake City, UT (US); Robert Schlaberg, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 913 days.

(21) Appl. No.: 15/724,476

(22) Filed: Oct. 4, 2017

(65) Prior Publication Data
US 2018/0365375 A1    Dec. 20, 2018

Related U.S. Application Data

(63) Continuation of application No. PCT/US2016/029067, filed on Apr. 22, 2016.

(60) Provisional application No. 62/152,782, filed on Apr. 24, 2015.

(51) Int. Cl.
*G16B 30/10*    (2019.01)
*G16B 30/00*    (2019.01)
*G16B 40/00*    (2019.01)
*G16B 40/20*    (2019.01)

(52) U.S. Cl.
CPC ............. *G16B 30/10* (2019.02); *G16B 30/00* (2019.02); *G16B 40/00* (2019.02); *G16B 40/20* (2019.02)

(58) Field of Classification Search
None
See application file for complete search history.

(56) References Cited

U.S. PATENT DOCUMENTS

| | | |
|---|---|---|
| 2012/0004111 A1 | 1/2012 | Colwell et al. |
| 2012/0114661 A1 | 5/2012 | Ginsburg et al. |
| 2014/0129152 A1 | 5/2014 | Beer et al. |
| 2014/0288844 A1 | 9/2014 | Hasan et al. |

FOREIGN PATENT DOCUMENTS

| | | |
|---|---|---|
| WO | WO2014/060305 A1 | 11/2013 |
| WO | WO-2016172643 A2 | 10/2016 |

OTHER PUBLICATIONS

Afshinnekoo, et al. Geospatial Resolution of Human and Bacterial Diversity with City-Scale Metagenomics. Cell Syst. Jul. 29, 2015;1(1):97-97.e3. doi: 10.1016/j.cels.2015.07.006. Epub Jul. 29, 2015.
Akobeng. Understanding diagnostic tests 3: Receiver operating characteristic curves. Acta Paediatr. May 2007;96(5):644-7. Epub Mar. 21, 2007.
Altschul, et al. Basic local alignment search tool. J Mol Biol. Oct. 5, 1990;215(3):403-10.
Anders, et al. Differential expression analysis for sequence count data. Genome Biol. 2010;11(10):R106. doi: 10.1186/GB-2010-11-10-r106. Epub Oct. 27, 2010.
Anthony, et al. A strategy to estimate unknown viral diversity in mammals. MBio. Sep. 3, 2013;4(5):e00598-13. doi: 10.1128/mBio.00598-13.
Audano, et al. KAnalyze: a fast versatile pipelined k-mer toolkit. Bioinformatics. Jul. 15, 2014;30(14):2070-2. doi: 10.1093/bioinformatics/btu152. Epub Mar. 18, 2014.
Borozan, et al. Evaluation of alignment algorithms for discovery and identification of pathogens using RNA-Seq. PLoS One. Oct. 30, 2013;8(10):e76935. doi: 10.1371/journal.pone.0076935. eCollection 2013.
Buchfink, et al. Fast and sensitive protein alignment using DIAMOND. Nat Methods. Jan. 2015;12(1):59-60. doi: 10.1038/nmeth.3176. Epub Nov. 17, 2014.
Caliendo, et al. Better tests, better care: improved diagnostics for infectious diseases. Clin Infect Dis. Dec. 2013;57 Suppl 3:S139-70. doi: 10.1093/cid/cit578.
Cantalupo, et al. HeLa nucleic acid contamination in the cancer genome atlas leads to the misidentification of human papillomavirus 18. J Virol. Apr. 2015;89(8):4051-7. doi: 10.1128/JVI.03365-14. Epub Jan. 28, 2015.
Chiu. Viral pathogen discovery. CurrOpin Microbiol. Aug. 2013;16(4):468-78. doi: 10.1016/j.mib.2013.05.001. Epub May 29, 2013.
Cole, et al. Ribosomal Database Project: data and tools for high throughput rRNA analysis. Nucleic Acids Res. Jan. 2014;42(Database issue):D633-42. doi: 10.1093/nar/gkt1244. Epub Nov. 27, 2013.
Consortium, et al. The MicroArray Quality Control (MAQC) project shows inter- and intraplatform reproducibility of gene expression measurements. Nat Biotechnol. Sep. 2006;24(9):1151-61.
Desantis, et al. Greengenes, a chimera-checked 16S rRNA gene database and workbench compatible with ARB. Appl Environ Microbiol. Jul. 2006;72(7):5069-72.

(Continued)

*Primary Examiner* — Joseph Woitach
(74) *Attorney, Agent, or Firm* — Morgan, Lewis & Bockius, LLP; Brett A. Lovejoy; Evelyn S. Chou

(57) ABSTRACT

Described herein are methods of identifying a plurality of polynucleotides, as well as detecting presence, absence, or abundance of a plurality of taxa in a sample. Also provided are systems for performing methods of the disclosure.

40 Claims, 35 Drawing Sheets

(56) References Cited

OTHER PUBLICATIONS

Dickson, et al. The role of the microbiome in exacerbations of chronic lung diseases. Lancet. Aug. 23, 2014;384(9944):691-702. doi: 10.1016/S0140-6736(14)61136-3.
Firth, et al. Detection of zoonotic pathogens and characterization of novel viruses carried by commensal Rattus norvegicus in New York City. MBio. Oct. 14, 2014;5(5):e01933-14. doi: 10.1128/mBio. 01933-14.
Flicek, et al. Ensembl 2014. Nucleic Acids Res. Jan. 2014;42(Database issue):D749-55. doi: 10.1093/nar/gkt1196. Epub Dec. 6, 2013.
Gilbert, et al. The Earth Microbiome project: successes and aspirations. BMC Biol. Aug. 22, 2014;12:69. doi: 10.1186/s12915-014-0069-1.
Gire, et al. Genomic surveillance elucidates Ebola virus origin and transmission during the 2014 outbreak. Science. Sep. 12, 2014;345(6202):1369-72. doi: 10.1126/science.1259657. Epub Aug. 28, 2014.
Goujon, et al. Human MX2 is an interferon-induced post-entry inhibitor of HIV-1 infection. Nature. Oct. 24, 2013;502(7472):559-62. doi: 10.1038/nature12542. Epub Sep. 18, 2013.
Grabherr, et al. Full-length transcriptome assembly from RNA-Seq data without a reference genome. Nat Biotechnol. May 15, 2011;29(7):644-52. doi: 10.1038/nbt.1883.
Graf. Evaluation of Metagenomics for the Detection of Respiratory Pathogens Directly from Clinical Samples. In Journal of Molecular Diagnostics. Nov. 1, 2014. vol. 16, No. 6, pp. 728-728.
Grard, et al. A novel rhabdovirus associated with acute hemorrhagic fever in central Africa. PLoS Pathog. Sep. 2012;8(9):e1002924. doi: 10.1371/journal.ppat.1002924. Epub Sep. 27, 2012.
Griebel, et al. Modelling and simulating generic RNA-Seq experiments with the flux simulator. Nucleic Acids Res. Nov. 1, 2012;40(20):10073-83. doi: 10.1093/nar/gks666. Epub Sep. 7, 2012.
Haller, et al. Mx GTPases: dynamin-like antiviral machines of innate immunity. Trends Microbiol. Mar. 2015;23(3):154-63. doi: 10.1016/j.tim.2014.12.003. Epub Jan. 6, 2015.
Hu, et al. Association between adverse clinical outcome in human disease caused by novel influenza A H7N9 virus and sustained viral shedding and emergence of antiviral resistance. Lancet. Jun. 29, 2013;381(9885):2273-9. doi: 10.1016/S0140-6736(13)61125-3. Epub May 29, 2013.
Hu, et al. Gene expression profiles in febrile children with defined viral and bacterial infection. Proc Natl Acad Sci USA. Jul. 30, 2013;110(31):12792-7. doi: 10.1073/pnas.1302968110. Epub Jul. 15, 2013.
Huang, et al. Temporal dynamics of host molecular responses differentiate symptomatic and asymptomatic influenza a infection. PLoS Genet. Aug. 2011;7(8):e1002234. doi: 10.1371/journal.pgen. 1002234. Epub Aug. 25, 2011.
Hudson, et al. A novel diagnostic approach may reduce inappropriate antibiotic use for acute respiratory infections. Expert Rev Anti Infect Ther. Mar. 2014;12(3):279-82. doi: 10.1586/14787210.2014. 881717. Epub Feb. 6, 2014.
International Search Report and Written Opinion dated Oct. 14, 2016 for International PCT Patent Application No. PCT/US2016/029067.
Jain, et al. Community-acquired pneumonia requiring hospitalization among U.S. children. N Engl J Med. Feb. 26, 2015;372(9):835-45. doi: 10.1056/NEJMoa1405870.
Koljalg, et al. Towards a unified paradigm for sequence-based identification of fungi. Mol Ecol. Nov. 2013;22(21):5271-7. doi: 10.1111/mec.12481. Epub Sep. 24, 2013.
Lax, et al. Longitudinal analysis of microbial interaction between humans and the indoor environment. Science. Aug. 29, 2014;345(6200):1048-52. doi: 10.1126/science.1254529.
Li, et al. The EMBL-EBI bioinformatics web and programmatic tools framework. Nucleic Acids Res. Jul. 1, 2015;43(W1):W580-4. doi: 10.1093/nar/gkv279. Epub Apr. 6, 2015.

Lipkin. The changing face of pathogen discovery and surveillance. Nat Rev Microbiol. Feb. 2013;11(2):133-41. doi: 10.1038/nrmicro2949. Epub Jan. 3, 2013.
Louis, et al. The gut microbiota, bacterial metabolites and colorectal cancer. Nat Rev Microbiol. Oct. 2014;12(10):661-72. doi: 10.1038/nrmicro3344. Epub Sep. 8, 2014.
Lusk. Diverse and widespread contamination evident in the unmapped depths of high throughput sequencing data. PLoS One. Oct. 29, 2014;9(10):e110808. doi: 10.1371/journal.pone.0110808. eCollection 2014.
Marcais, et al. A fast, lock-free approach for efficient parallel counting of occurrences of k-mers. Bioinformatics. Mar. 15, 2011;27(6):764-70. doi: 10.1093/bioinformatics/btr011. Epub Jan. 7, 2011.
Mariotti, et al. Mollicutes contamination: a new strategy for an effective rescue of cancer cell lines. Biologicals. Jan. 2012;40(1):88-91. doi: 10.1016/j.biologicals.2011.10.006. Epub Nov. 9, 2011.
Mayer, et al. Gut/brain axis and the microbiota. J Clin Invest. Mar. 2, 2015;125(3):926-38. doi: 10.1172/JCI76304. Epub Feb. 17, 2015.
McDonald, et al. An improved Greengenes taxonomy with explicit ranks for ecological and evolutionary analyses of bacteria and archaea. ISME J. Mar. 2012;6(3):610-8. doi: 10.1038/ismej.2011. 139. Epub Dec. 1, 2011.
McDonald, et al. The Biological Observation Matrix (BIOM) format or: how I learned to stop worrying and love the ome-ome. Gigascience. Jul. 12, 2012;1(1):7. doi: 10.1186/2047-217X-1-7.
Merchant, et al. Unexpected cross-species contamination in genome sequencing projects. PeerJ. Nov. 20, 2014;2:e675. doi: 10.7717/peerj.675. eCollection 2014.
Miller, et al. bam.iobio: a web-based, real-time, sequence alignment file inspector. Nat Methods. Dec. 2014;11(12):1189. doi: 10.1038/nmeth.3174.
Naccache, et al. A cloud-compatible bioinformatics pipeline for ultrarapid pathogen identification from next-generation sequencing of clinical samples. Genome Res. Jul. 2014;24(7):1180-92. doi: 10.1101/gr.171934.113. Epub Jun. 4, 2014.
Naccache, et al. The perils of pathogen discovery: origin of a novel parvovirus-like hybrid genome traced to nucleic acid extraction spin cols. J Virol. Nov. 2013;87(22):11966-77. doi: 10.1128/JVI.02323-13. Epub Sep. 11, 2013.
Olarerin-George, et al. Assessing the prevalence of mycoplasma contamination in cell culture via a survey of NCBI's RNA-seq archive. Nucleic Acids Res. Mar. 11, 2015 ;43(5):2535-42. doi: 10.1093/nar/gkv136. Epub Feb. 24, 2015.
Patro, et al. Sailfish enables alignment-free isoform quantification from RNA-seq reads using lightweight algorithms. Nat Biotechnol. May 2014;32(5):462-4. doi: 10.1038/nbt.2862. Epub Apr. 20, 2014.
Petti. Interpretive criteria for identification of bacteria and fungi by DNA target sequencing. Clinical and Laboratory Standards Institute; 2008.
Pierce. An introduction to information theory: symbols, signals and noise. Edn. 2nd rev. Dover Publications, New York. 1980.
Rinke, et al. Insights into the phylogeny and coding potential of microbial dark matter. Nature. Jul. 25, 2013;499(7459):431-7. doi: 10.1038/nature12352. Epub Jul. 14, 2013.
Rosseel, et al. False-positive results in metagenomic virus discovery: a strong case for follow-up diagnosis. Transbound Emerg Dis. Aug. 2014;61(4):293-9. doi: 10.1111/tbed.12251. Epub Jun. 10, 2014.
Rotmistrovsky, et al. BMTagger: Best Match Tagger for removing human reads from metagenomics datasets. Bioinformatics. 2011.
Sayers, et al. Database resources of the National Center for Biotechnology Information. Nucleic Acids Res. Jan. 2010;38(Database issue):D5-16. doi: 10.1093/nar/gkp967. Epub Nov. 12, 2009.
Shakya, et al. Comparative metagenomic and rRNA microbial diversity characterization using archaeal and bacterial synthetic communities. Environ Microbiol. Jun. 2013;15(6): 1882-99. doi: 10.1111/1462-2920.12086. Epub Feb. 6, 2013.
Sherrard, et al. Antimicrobial resistance in the respiratory microbiota of people with cystic fibrosis. Lancet. Aug. 23, 2014;384(9944):703-13. doi: 10.1016/S0140-6736(14)61137-5.

(56) References Cited

OTHER PUBLICATIONS

Smuts, et al. Novel hybrid parvovirus-like virus, NIH-CQV/PHV, contaminants in silica columnbased nucleic acid extraction kits. J Virol. Jan. 2014;88(2):1398. doi: 10.1128/JVI.03206-13. Epub Dec. 11, 2013.
Strong, et al. Microbial contamination in next generation sequencing: implications for sequence-based analysis of clinical samples. PLoS Pathog. Nov. 20, 2014;10(11):e1004437. doi: 10.1371/journal.ppat.1004437. eCollection 2014.
Subramanian, et al. Persistent gut microbiota immaturity in malnourished Bangladeshi children. Nature. Jun. 19, 2014;510(7505):417-21. doi: 10.1038/nature13421. Epub Jun. 4, 2014.
Suzek, et al. UniRef: comprehensive and non-redundant UniProt reference clusters. Bioinformatics. May 15, 2007;23(10):1282-8. Epub Mar. 22, 2007.
Trapnell, et al. TopHat: discovering splice junctions with RNA-Seq. Bioinformatics. May 1, 2009;25(9):1105-11. doi: 10.1093/bioinformatics/btp120. Epub Mar. 16, 2009.
Trapnell, et al. Transcript assembly and quantification by RNA-Seq reveals unannotated transcripts and isoform switching during cell differentiation. Nat Biotechnol. May 2010;28(5):511-5. doi: 10.1038/nbt.1621. Epub May 2, 2010.
Wilson, et al. Actionable diagnosis of neuroleptospirosis by next-generation sequencing. N Engl J Med. Jun. 19, 2014;370(25):2408-17. doi: 10.1056/NEJMoa1401268. Epub Jun. 4, 2014.
Wood, et al. Kraken: ultrafast metagenomic sequence classification using exact alignments. Genome Biol. Mar. 3, 2014;15(3):R46. doi: 10.1186/GB-2014-15-3-r46.
Xie, et al. SOAPdenovo-Trans: de novo transcriptome assembly with short RNA-Seq reads. Bioinformatics. Jun. 15, 2014;30(12):1660-6. doi: 10.1093/bioinformatics/btu077. Epub Feb. 13, 2014.

Yarza, et al. Uniting the classification of cultured and uncultured bacteria and archaea using 16S rRNA gene sequences. Nat Rev Microbiol. Sep. 2014;12(9):635-45. doi: 10.1038/nrmicro3330.
Yilmaz, et al. The SILVA and "All-species Living Tree Project (LTP)" taxonomic frameworks. Nucleic Acids Res. Jan. 2014;42(Database issue):D643-8. doi: 10.1093/nar/gkt1209. Epub Nov. 28, 2013.
Zaas, et al. A host-based RT-PCR gene expression signature to identify acute respiratory viral infection. Sci Transl Med. Sep. 18, 2013;5(203):203ra126. doi: 10.1126/scitranslmed.3006280.
Zaas, et al. Gene expression signatures diagnose influenza and other symptomatic respiratory viral infections in humans. Cell Host Microbe. Sep. 17, 2009;6(3):207-17. doi: 10.1016/j.chom.2009.07.006. Epub Aug. 6, 2009.
Zaharia, et al. Faster and more accurate sequence alignment with SNAP. arXiv preprint arXiv:1111.5572. Nov. 23, 2011.
Zhang, et al. A greedy algorithm for aligning DNA sequences. J Comput Biol. Feb.-Apr. 2000;7(1-2):203-14.
Zhao, et al. RAPSearch2: a fast and memory-efficient protein similarity search tool for next-generation sequencing data. Bioinformatics. Jan. 1, 2012;28(1):125-6. doi: 10.1093/bioinformatics/btr595. Epub Oct. 28, 2011.
Zhao. The gut microbiota and obesity: from correlation to causality. Nat Rev Microbiol. Sep. 2013;11(9):639-47. doi: 10.1038/nrmicro3089. Epub Aug. 5, 2013.
Ounit et al., 2015 "CLARK: fast and accurate classification of metagenomic and genomic sequences using discriminative k-mers," BMC Genomics 16(1), p. 236.
Jolanta Kawulok et al., "CoMeta: Classification of Metagenomes Using k-mers", PLOS ONE, (Apr. 17, 2015), vol. 10, No. 4, doi:10.1371/journal.pone.0121453, p. e0121453. [1] Category: X, Claims: 1-46, 65-69.

| Sample | Approach | Platform, Reads | Reads/Sample | Time/Sample [s] Taxonomer | Time/Sample [s] RDP | Rank | ρ |
|---|---|---|---|---|---|---|---|
| Stool | 16S (V4) amplicon | HiSeq (1x150bp) | 1.6x10⁴ | 0.7 min | 311 min | Order | 0.960 |
| | | | | | | Genus | 0.858 |
| Environment, human, pets | 16S (V4) amplicon | MiSeq (2x150bp) | 7.3x10⁴ | 1.8 min | 644 min | Order | 0.997 |
| | | | | | | Genus | 0.826 |
| Respiratory | RNA-Seq | HiSeq (2x100 bp) | 1.6x10⁶ | 27.4 min | 7,245 min | Order | 0.992 |
| | | | | | | Genus | 0.955 |

FIG. 2E

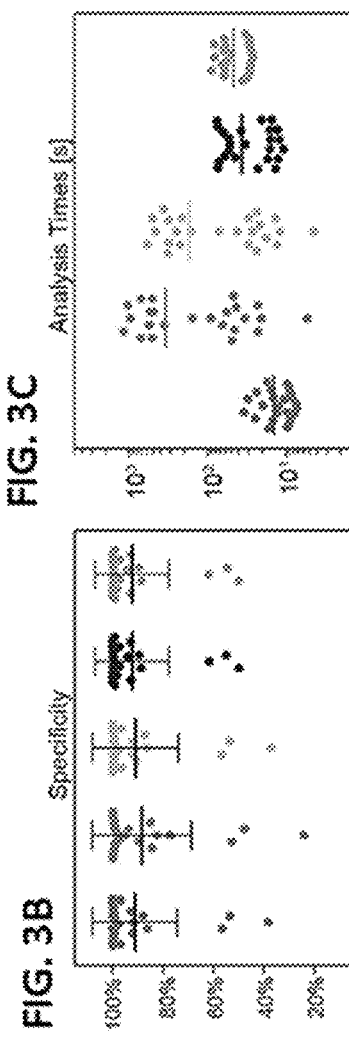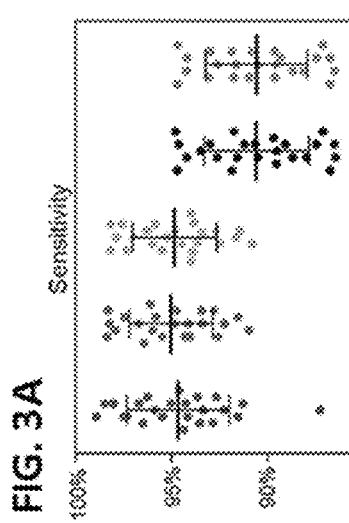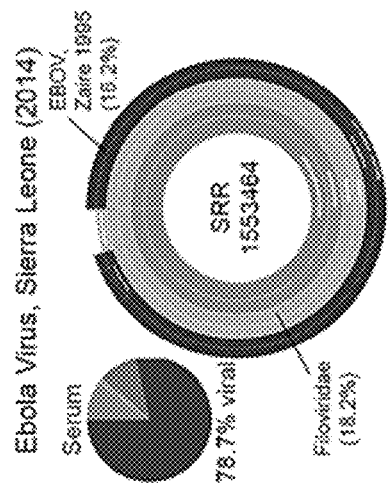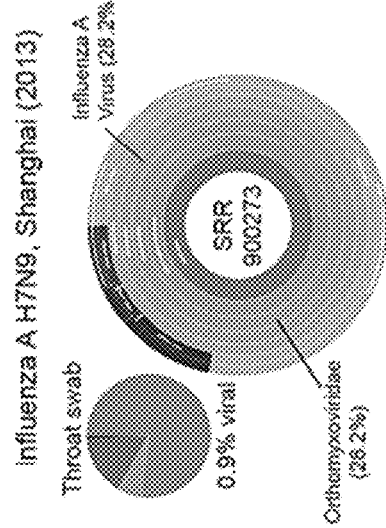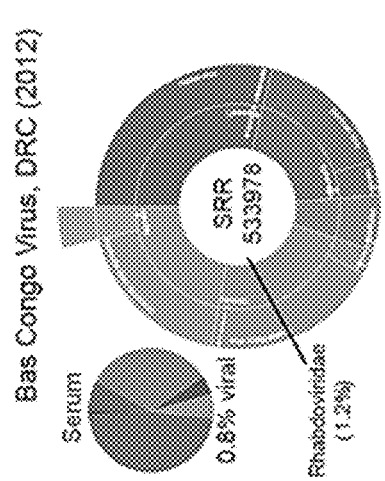
FIG. 3A  FIG. 3B  FIG. 3C  FIG. 3D  FIG. 3E  FIG. 3F

FIG. 4E

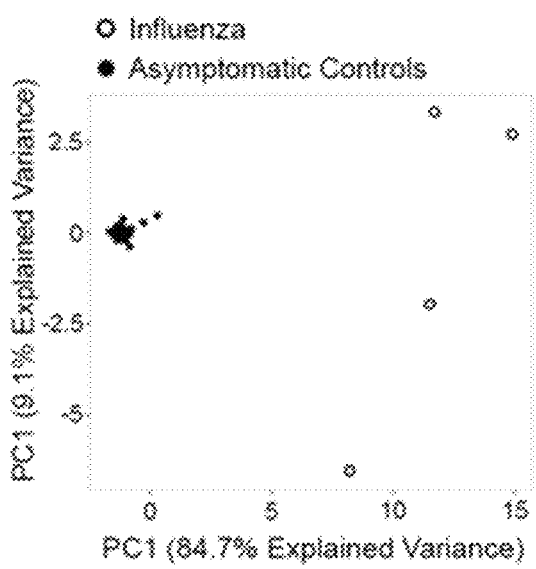

FIG. 4F

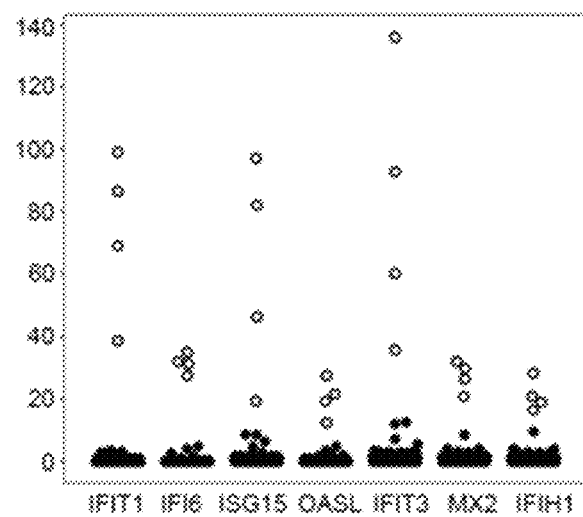

FIG. 4G

| Term | GO Accession | Background frequency | Sample frequency | P-value | Up/Down |
|---|---|---|---|---|---|
| Defense response to virus | 0051607 | 148 | 22 | 3.3E-31 | Up |
| Response to virus | 0009615 | 252 | 23 | 4.7E-28 | Up |
| Defense response to other organism | 0098542 | 328 | 23 | 1.9E-25 | Up |
| Response to other organism | 0051707 | 645 | 26 | 1.9E-23 | Up |
| Response to external biotic stimulus | 0043207 | 645 | 26 | 1.9E-23 | Up |
| Immune effector process | 0002252 | 413 | 23 | 3.4E-23 | Up |
| Response to biotic stimulus | 0009607 | 674 | 26 | 5.7E-23 | Up |
| Type I interferon signaling pathway | 0060337 | 68 | 15 | 1.9E-22 | Up |
| Cellular response to type I interferon | 0071357 | 68 | 15 | 1.9E-22 | Up |
| Response to type I interferon | 0034340 | 69 | 15 | 2.3E-22 | Up |

FIG. 4H

| Term | GO Accession | Background frequency | Sample frequency | P-value | Up/Down |
|---|---|---|---|---|---|
| 2'-5'-oligoadenylate synthetase activity | 0001730 | 4 | 4 | 5.15E-07 | Up |
| Double-stranded RNA binding | 0003725 | 53 | 6 | 5.45E-06 | Up |
| Adenylyltransferase activity | 0070568 | 23 | 4 | 5.46E-04 | Up |

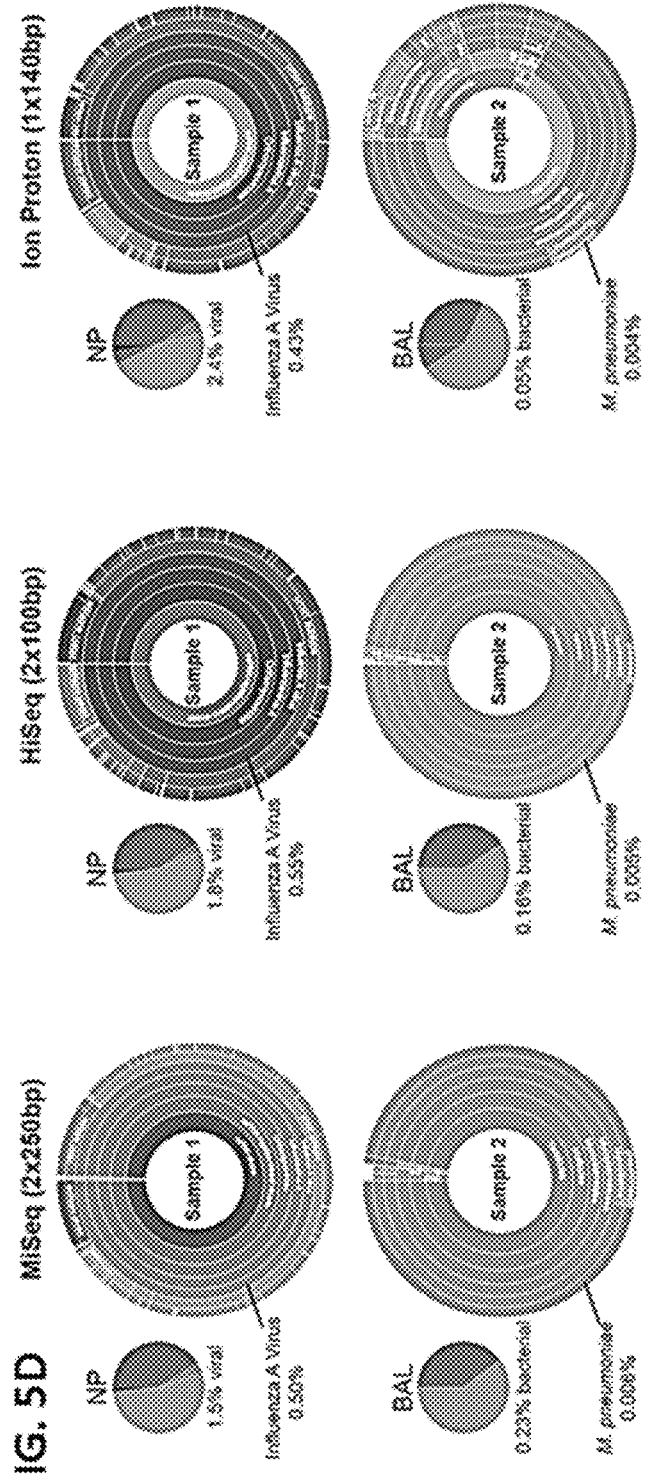
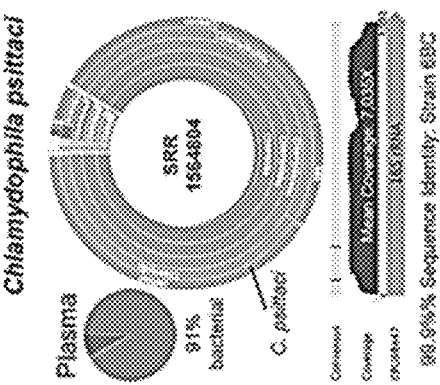
FIG. 5A  FIG. 5B  FIG. 5C  FIG. 5D

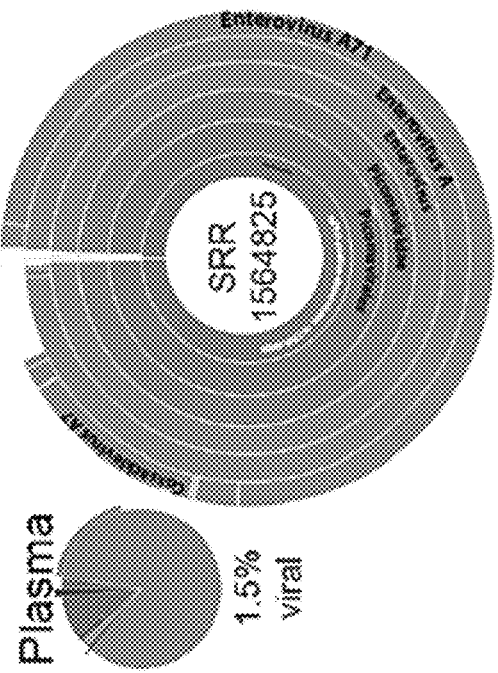
FIG. 16A
*E. meningoseptica*
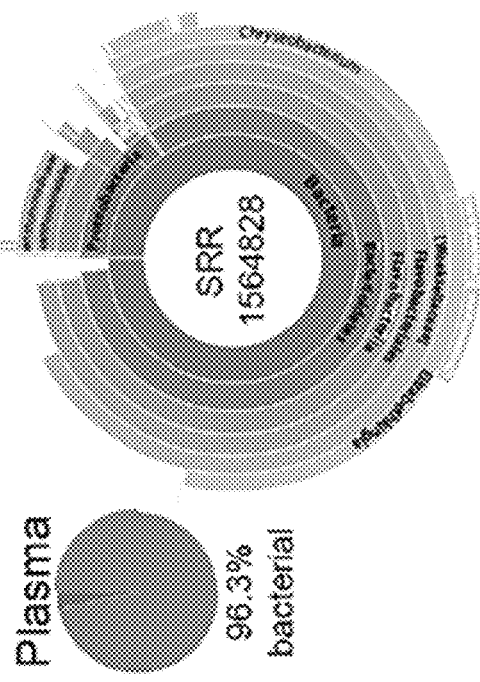
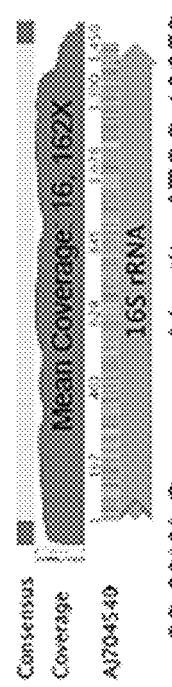
FIG. 16B
Coxsackievirus

| Sample Composition | Total Reads, Pathogen | Application | Subtraction | Binning | Classification | Protein Search | Total Time | % Reads Classified |
|---|---|---|---|---|---|---|---|---|
| | 6,599,164 HCoV | Taxonomer | - | 5m | 22s | 10s | 5.5m | 99% |
| | | Kraken | - | - | 1.5m | - | 1.5m | 99% |
| | | SURPI | 3.3m | - | 74m | 15m | 92m | 98% |
| | 7,542,552 Influenza A virus | Taxonomer | - | 8m | 40s | 30s | 9.2m | 77% |
| | | Kraken | - | - | 1.5m | - | 1.5m | 66% |
| | | SURPI | 9.8m | - | 208m | 18m | 236m | 78% |
| | 6,252,311 HMPV | Taxonomer | - | 5.2m | 56s | 10s | 6.3m | 97% |
| | | Kraken | - | - | 1.3m | - | 1.3m | 93% |
| | | SURPI | 56m | - | 648m | 24m | 728m | 95% |

FIG. 18

| Binner Databases | Flags | Sources | Versions | Sequences | k-mers | Sources |
|---|---|---|---|---|---|---|
| Human genome | 2 | NCBI / SILVA | GRCh38 / 4/10/2014 | 455 +81 LSU +158 SSU | 2,257,262,659 | ftp.ncbi.nlm.nih.gov/genomes/Homo_sapiens/Assembled_chromosomes/seq/ www.arb-silva.de/documentation/release-119 |
| Human transcripts | 32 | NCBI | 4/10/2014 | 98,746 | 79,809,821 | ftp.ncbi.nlm.nih.gov/genomes/H_sapiens/RNA/ |
| Human mitochondria | 512 | Mitomap | 4/10/2014 | 26,829 | 248,056 | mitomap.org/bin/view.pl/MITOMAP/Mitobank |
| Bacterial genomes | 1 | NCBI | 4/10/2014 | 5,189 | 5,433,934,380 | ftp.ncbi.nlm.nih.gov/genomes/ |
| Bacterial SSU | 128 | SILVA | 119_ref | 1,473,625 | 43,354,161 | www.arb-silva.de/documentation/release-119 |
| Bacterial LSU | 256 | SILVA | 119_ref | 41,505 | 4,817,477 | www.arb-silva.de/documentation/release-119 |
| Plastids LSU/SSU | 16384 | SILVA | 119_ref | 2,946 LSU 10,458 SSU | 2,148,466 | www.arb-silva.de/documentation/release-119 |
| Fungal genomes | 4 | NCBI | 4/10/2014 | 1,146 | 585,739,768 | ftp.ncbi.nlm.nih.gov/genomes/ |
| Fungal LSU/SSU | 64 | SILVA | 119_ref | 2,317 LSU 21,106 SSU | 2,306,754 | www.arb-silva.de/documentation/release-119 |
| Fungal ITS | 1024 | UNITE | 07/04/2014 | 409,493 | 19,398,519 | unite.ut.ee/index.php |
| Viruses (NCBI) | 8 | NCBI | 8/7/2014 | 1,668,565 | 279,444,799 | entrez search with query (txid10239[Organism] and not txid131567[Organism] and not gbdiv_pat[PROP]) |
| Phages | 16 | NCBI | 4/10/2014 | 14,440 | 69,802,836 | Phage_tax_ID's per viralzone+: viralzone.expasy.org/all_by_protein/256.html and viralzone.expasy.org/all_by_species/663.html |
| PhiX174 | 4096 | NCBI | | 1 | 5,366 | NC_001422 |
| Other Eukaryotes LSU/SSU | 2048 | SILVA | 119_ref | 86,633 | 16,062,986 | |
| Repeat markers | 8192 | Repeatma sker | | 383 | 16,419 | www.repeatmasker.org |
| Adapter sequences | | | | 0 | 0 | |
| ERCC controls | | | | 0 | 0 | |

FIG. 19

| | MiSeq (2 x 250 bp) | | | HiSeq (2 x 100 bp) | | | Ion Proton (1 x ~140 bp) | | |
|---|---|---|---|---|---|---|---|---|---|
| Bin | Reads (n) | % | Pathogen reads (%) | Reads (n) | % | Pathogen reads (%) | Reads (n) | % | Pathogen reads (%) |
| Influenza A | | | | | | | | | |
| Human | 2,383,619 | 78.3 | | 23,365,714 | 80.8 | | 16,004,966 | 86.0 | |
| Fungal | 2,824 | 0.1 | | 57,141 | 0.2 | | 88,237 | 0.5 | |
| ITS | 101 | 0.0 | | 3,065 | 0.0 | | 1,088 | 0.0 | |
| Bacteria | 105,307 | 3.5 | | 922,407 | 3.2 | | 783,684 | 4.2 | |
| 16S | 21,776 | 0.7 | | 215,163 | 0.7 | | 501,958 | 2.7 | |
| Phage | 1,328 | 0.0 | | 2,943 | 0.0 | | 3 | 0.0 | |
| Viral | 44,670 | 1.5 | 99.5 | 538,290 | 1.9 | 99.3 | 467,567 | 2.5 | 99.2 |
| Other | 476,256 | 15.7 | | 3,786,107 | 13.1 | | 719,070 | 3.9 | |
| Ambiguous | | | | | | | | | |
| Unknown | 3,958 | 0.1 | | 26,939 | 0.1 | | 36,934 | 0.2 | |
| Mycoplasma | | | | | | | | | |
| Human | 3,015,081 | 88.2 | | 26,438,464 | 89.9 | | 15,464,350 | 94.4 | |
| Fungal | 3,290 | 0.1 | | 67,372 | 0.2 | | 42,548 | 0.3 | |
| ITS | 48 | 0.0 | | 3,636 | 0.0 | | 459 | 0.0 | |
| Bacteria | 1,749 | 0.1 | | 9,454 | 0.0 | | 7,917 | 0.1 | |
| 16S | 309 | 0.0 | 69.3 | 2,951 | 0.0 | 65.9 | 2,650 | 0.0 | 30.5 |
| Phage | 1,270 | 0.0 | | 3,158 | 0.0 | | 0 | 0.0 | |
| Viral | 64 | 0.0 | | 509 | 0.0 | | 295 | 0.0 | |
| Other | 391,584 | 11.5 | | 2,834,912 | 5.0 | | 825,431 | 5.0 | |
| Ambiguous | | | | | | | | | |
| Unknown | 1,255 | 0.0 | | 20,841 | 0.1 | | 34,997 | 0.2 | |

FIG. 20

METHODS AND SYSTEMS FOR MULTIPLE TAXONOMIC CLASSIFICATION

CROSS-REFERENCE

This application is a continuation of PCT application PCT/US2016/029067, filed on Apr. 22, 2016, which claims the benefit of U.S. Provisional Application No. 62/152,782, filed Apr. 24, 2015, which application is incorporated herein by reference.

BACKGROUND OF THE INVENTION

Metagenomics, the genomic analysis of a population of microorganisms, makes possible the profiling of microbial communities in the environment and the human body at unprecedented depth and breadth. Its rapidly expanding use is revolutionizing our understanding of microbial diversity in natural and man-made environments and is linking microbial community profiles with health and disease. To date, most studies have relied on PCR amplification of microbial marker genes (e.g. bacterial 16S rRNA), for which large, curated databases have been established. More recently, higher throughput and lower cost sequencing technologies have enabled a shift towards enrichment-independent metagenomics. These approaches reduce bias, improve detection of less abundant taxa, and enable discovery of novel pathogens While conventional, pathogen-specific nucleic acid amplification tests are highly sensitive and specific, they require a priori knowledge of likely pathogens. The result is increasingly large, yet inherently limited diagnostic panels to enable diagnosis of the most common pathogens. In contrast, enrichment-independent high-throughput sequencing allows for unbiased, hypothesis-free detection and molecular typing of a theoretically unlimited number of common and unusual pathogens. Wide availability of next-generation sequencing instruments, lower reagent costs, and streamlined sample preparation protocols are enabling an increasing number of investigators to perform high-throughput DNA and RNA-seq for metagenomics studies. However, analysis of sequencing data is still forbiddingly difficult and time consuming, requiring bioinformatics skills, computational resources, and microbiological expertise that is not available to many laboratories, especially diagnostic ones.

SUMMARY OF THE INVENTION

In view of the foregoing, more computationally efficient, accurate, and easy-to-use tools for comprehensive diagnostic and metagenomics analyses are needed. The methods and systems described herein address this need, and provide other advantages as well.

In one aspect, the present disclosure provides a method of identifying a plurality of polynucleotides in a sample from a sample source. In some embodiments, the method comprises providing sequencing reads for a plurality of polynucleotides from the sample, and for each sequencing read: (a) performing with a computer system a sequence comparison between the sequencing read and a plurality of reference polynucleotide sequences, wherein the comparison comprises calculating k-mer weights as a measure of how likely it is that k-mers within the sequencing read are derived from a reference sequence within the plurality of reference polynucleotide sequences; (b) identifying the sequencing read as corresponding to a particular reference sequence in a database of reference sequences if the sum of k-mer weights for the reference sequence is above a threshold level; and (c) assembling a record database comprising reference sequences identified in step (b), wherein the record database excludes reference sequences to which no sequencing read corresponds.

In another aspect, the present disclosure provides a method of identifying one or more taxa in a sample from a sample source, the method comprising: (a) providing sequencing reads for a plurality of polynucleotides from the sample, and for each sequencing read: (i) performing with a computer system a sequence comparison between the sequencing read and a plurality of reference polynucleotide sequences, wherein the comparison comprises calculating k-mer weights as a measure of how likely it is that k-mers within the sequencing read are derived from a reference sequence within the plurality of reference polynucleotide sequences; and (ii) calculating a probability that the sequencing read corresponds to a particular reference sequence in a database of reference sequences based on the k-mer weights, thereby generating a sequence probability; (b) calculating a score for the presence or absence of one or more taxa based on the sequence probabilities corresponding to sequences representative of said one or more taxa; and (c) identifying the one or more taxa as present or absent in the sample based on the corresponding scores. In some embodiments, the one or more taxa comprise a first bacterial strain identified as present and a second bacterial strain identified as absent based on one or more nucleotide differences in sequence. In some embodiments, the first bacterial strain is identified as present and the second bacterial strain is identified as absent based on a single nucleotide difference in sequence. In some embodiments, the method further comprises identifying a condition of the sample source by comparison of the results of step (c) to a biosignature.

In some embodiments of any of the various aspects of the disclosure, each reference sequence in the database of reference sequences is associated with, prior to the comparison, a reference k-mer weight as a measure of how likely it is that a k-mer within the reference sequence originates from the reference sequence. In some embodiments, the database of reference sequences comprise sequences from a plurality of taxa, and each reference sequence in the database of reference sequences is associated with a reference k-mer weight as a measure of how likely it is that a k-mer within the reference sequence originates from a taxon within the plurality of taxa. One or more of the steps may be performed for all sequencing reads in parallel, such as the step of performing the sequence comparison. The method may further comprise quantifying an amount of polynucleotides corresponding to the reference sequences identified in step (b) based on a number of corresponding sequencing readings. In some embodiments, the method further comprises determining presence, absence, or abundance of a plurality of taxa in the sample based on results of step (b), wherein the plurality of reference polynucleotide sequences comprise groups of sequences corresponding to individual taxa in the plurality of taxa. A sequencing read identified as belonging to a particular taxon in the plurality of taxa and not present among the group of sequences corresponding to that taxon can be added to the group of sequences corresponding to that taxon for use in later sequence comparisons. In some embodiments, determining the presence, absence, or abundance of a taxon in the plurality of taxa comprises resolving a tie between two possible taxa to which a sequencing read corresponds, wherein resolving the tie comprises determining a sum of k-mer weights for the reference sequence along each branch of a phylogenetic tree. In some cases, a particular individual is identified as the sample source.

The database of reference sequences can comprise any of a variety of reference sequences. In some embodiments, the reference sequences are from one or more of bacteria, archaea, chromalveolata, viruses, fungi, plants, fish, amphibians, reptiles, birds, mammals, and humans. In some cases, the database of reference sequences consists of sequences from a reference individual or a reference sample source. In this case, the method may further comprise identifying the polynucleotides from the sample source as being derived from the reference individual or the reference sample source. In some embodiments, the database of reference sequences comprises k-mers having one or more mutations with respect to known polynucleotide sequences, such that a plurality of variants of the known polynucleotide sequences are represented in the database of reference sequences. The database of reference sequences can comprise marker gene sequences for taxonomic classification of bacterial sequences, such as 16S rRNA sequences. In some embodiments, the database of reference sequences comprises sequences of human transcripts.

In some embodiments, the database of reference sequences consists of sequences associated with a condition. One or more such sequences may form a biosignature for the condition, a plurality of which may together form the reference database. In some cases, the record database is associated with a condition of the sample source to establish a biosignature for the condition. When sequences are associated with a condition, the method may further comprise identifying a condition of the sample source by comparison of the record database to a biosignature, including identifying the sample source as having the condition. The condition may be contamination, such as food contamination, surface contamination, or environmental contamination. In some embodiments, the condition is infection. Biosignatures (e.g. of infection) can comprise (i) sequences of host transcript or levels of sequences of host transcripts; and/or (ii) sequences of one or more infectious agents. In some embodiments, the infection is influenza and the biosignature consists of sequences of one or more of IFIT1, IFI6, IFIT2, ISG15, OASL, IFIT3, NT5C3A, MX2, IFITM1, CXCL10, IFI44L, MX1, IFIH1, OAS2, SAMD9, RSAD2, DDX58. The sample source can be any of a variety of sample sources. In some cases, the sample source is a subject. Where sequences are associated with a condition, the method may further comprise monitoring treatment in an infected subject by identifying the presence or absence of the biosignature in samples from the infected subject at multiple times after beginning treatment. Treatment of the infected subject can be adjusted based on results of the monitoring.

In some embodiments, methods of the present disclosure comprise selecting, and optionally taking, medical action based on the results of sequence and/or taxa identification. For example, medical action can comprise administering a pharmaceutical composition, such as an antibiotic. In some embodiments, the antibiotic is selected based on efficacy against taxa identified in the sample.

In some embodiments, the database of reference sequences comprises polynucleotide sequences reverse-translated from amino acid sequences. Reverse-translating can use a non-degenerate code comprising a single codon for each amino acid. Where a non-degenerate code is used, a sequencing read can be translated to an amino acid sequence and then reverse-translated using the non-degenerate code prior to comparison with the reverse-translated reference sequences.

In some embodiments, the k-mer weight relates a count of a particular k-mer within a particular reference sequence, a count of the particular k-mer among a group of sequences comprising the reference sequence, and a count of the particular k-mer among all reference sequences in the database of reference sequences. In some embodiments, step (b) is completed for 20,000 sequencing reads in less than 1.5 seconds. The 20,000 sequencing reads can comprise sequences from two or more of bacteria, viruses, fungi, and humans. In some embodiments, steps (a)-(c) are performed by a computer system in response to a user request. In some embodiments, the user uploads the sequencing reads to the computer system, and the method is performed concurrently with the upload. In some embodiments, the user uploads a plurality of sequencing reads to the computer system, and results of the sequence analysis are reported to the user for one or more of the plurality of sequencing reads while other sequencing reads of the plurality of sequencing reads are uploading. For example, a sequencing file containing a plurality of sequencing reads may be broken into smaller components (e.g. subsets of one or more sequencing reads), and components uploaded first may be analyzed and reported while the remainder of the file continues to upload. The computer system may be remote with respect to the user. The method can further comprise sequencing the plurality of polynucleotides from the sample to generate the sequencing reads.

In one aspect, the present disclosure provides a method of detecting a plurality of taxa in a sample. In some embodiments, the method comprising providing sequencing reads for a plurality of polynucleotides from the sample, and for each sequencing read: (a) assigning the sequencing read to a first taxonomic group based on a first sequence comparison between the sequencing read and a first plurality of polynucleotide sequences from the different first taxonomic groups, wherein at least two sequencing reads are assigned to different taxonomic groups; (b) performing with a computer system a second sequence comparison between the sequencing read and a second plurality of polynucleotide sequences corresponding to members of the first taxonomic group, wherein the comparison comprises counting a number of k-mers within the sequencing read of at least 5 nucleotides in length that exactly match one or more k-mers within a reference sequence in the second plurality of polynucleotide sequences; (c) classifying the sequencing read as belonging to a second taxonomic group that is more specific than the first taxonomic group if a measure of similarity between the sequencing read and reference sequence is above a first threshold level; (d) if no similarity above the first threshold level is identified in (c), classifying the sequencing read as belonging to the second taxonomic group based on similarity above a second threshold level determined by comparing with the computer system a sequence derived from translating the sequencing read and a third set of reference sequences corresponding to amino acid sequences of members of the first taxonomic group; and (e) identifying the presence, absence, or abundance of the plurality of taxa in the sample based on the classifying of the sequencing reads. Step (b) may further comprise calculating k-mer weights as measures of how likely it is that k-mers within the sequencing read are derived from a reference sequence in the second plurality of polynucleotide sequences. In some embodiments, the third set of reference sequences consist of polynucleotide sequences derived from reverse-translating the corresponding amino acid sequences. The method can further comprise performing with the computer system a relaxed sequence comparison between the sequencing read and the second plurality of polynucleotide sequences if the similarity in (d) is below the second threshold, wherein the relaxed sequence comparison is less stringent than the second sequence comparison. In some embodiments, classifying the sequencing read in step (c) comprises resolving a tie between two or more possible taxonomic groups based on a k-mer weight as a measure of how likely it is that the sequencing read corresponds to a polynucleotide from an ancestor of one of the possible taxonomic groups. In some embodiments, step (a) comprises assigning sequencing reads to two or more taxa selected from bacteria, viruses, fungi, or humans. In some embodiments, a sequencing read classified as belonging to the second taxonomic group and not present among the group of sequences corresponding to the second taxonomic group is added to the group of sequences corresponding to the second taxonomic group for use in later sequence comparisons. The second plurality of nucleotide sequences may comprise marker gene sequences for taxonomic classification of bacterial sequences, such as 16S rRNA sequences. The second plurality of nucleotide sequences may comprise sequences of human transcripts.

In some embodiments, the method further comprises diagnosing a condition based on a degree of similarity between the plurality of taxa detected in the sample and a biological signature for the condition. The condition can be contamination of the sample, or infection of a subject. When the condition is infection of a subject, the infection can be assessed based on the presence or amount of (i) sequences of host transcripts; and/or (ii) sequences of one or more infectious agents. The method can further comprise monitoring treatment in an infected subject by detecting presence, absence, or abundance of a plurality of taxa in samples from the infected subject at multiple times after beginning treatment, and optionally changing treatment of the infected subject based on results of the monitoring. The method may further comprise classifying the sequencing read as corresponding to a gene transcript if the measure of similarity between the sequencing read and reference sequence is above the first threshold level. Where a sequencing read is classified as corresponding to a gene transcript, the method may further comprise diagnosing a condition based on a degree of similarity between the plurality of taxa detected in the sample and a biological signature for the condition.

In one aspect, the disclosure provides systems for performing any of the methods described herein. In some embodiments, the system is configured for identifying a plurality of polynucleotides in a sample from a sample source based on sequencing reads for the plurality of polynucleotides. For example, the system may comprise one or more computer processors programmed to, for each sequencing read: (a) perform a sequence comparison between the sequencing read and a plurality of reference polynucleotide sequences, wherein the comparison comprises calculating k-mer weights as measures of how likely it is that k-mers within the sequencing read are derived from a reference sequence within the plurality of reference polynucleotide sequences; (b) identify the sequencing read as corresponding to a particular reference sequence in a database of reference sequences if the sum of k-mer weights for the reference sequence is above a threshold level; and (c) assemble a record database comprising reference sequences identified in step (b), wherein the record database excludes reference sequences to which no sequencing read corresponds. The system may further comprise a reaction module in communication with the computer processor, wherein the reaction module performs polynucleotide sequencing reactions to produce the sequencing reads.

In some embodiments, the system is configured for identifying one or more taxa in a sample from a sample source based on sequencing reads for a plurality of polynucleotides. For example, the system may comprise one or more computer processors programmed to: (a) for each sequencing read, perform a sequence comparison between the sequencing read and a plurality of reference polynucleotide sequences, wherein the comparison comprises calculating k-mer weights as measures of how likely it is that k-mers within the sequencing read are derived from a reference sequence within the plurality of reference polynucleotide sequences; (b) for each sequencing read, calculate a probability that the sequencing read corresponds to a particular reference sequence in a database of reference sequences based on the k-mer weights, thereby generating a sequence probability; (c) calculate a score for the presence or absence of one or more taxa based on the sequence probabilities corresponding to sequences representative of said one or more taxa; and (d) identify the one or more taxa as present or absent in the sample based on the corresponding scores. The system may further comprise a reaction module in communication with the computer processor, wherein the reaction module performs polynucleotide sequencing reactions to produce the sequencing reads.

In one aspect, the disclosure provides a computer-readable medium comprising code that, upon execution by one or more processors, implements a method according to any of the methods disclosed herein. In some embodiments, execution of the computer readable medium implements a method of identifying a plurality of polynucleotides in a sample from a sample source based on sequencing reads for the plurality of polynucleotides. In one embodiment, the execution of the computer readable medium implements a method comprising: (a) for each of the sequencing reads, performing a sequence comparison between the sequencing read and a plurality of reference polynucleotide sequences, wherein the comparison comprises calculating k-mer weights as measures of how likely it is that k-mers within the sequencing read are derived from a reference sequence within the plurality of reference polynucleotide sequences; (b) for each of the sequencing reads, identifying the sequencing read as corresponding to a particular reference sequence in a database of reference sequences if the sum of k-mer weights for the reference sequence is above a threshold level; and (c) assembling a record database comprising reference sequences identified in step (b), wherein the record database excludes reference sequences to which no sequencing read corresponds.

In some embodiments, the execution of the computer readable medium implements a method of identifying one or more taxa in a sample from a sample source based on sequencing reads for a plurality of polynucleotides, the method comprising: (a) for each of the sequencing reads, performing a sequence comparison between the sequencing read and a plurality of reference polynucleotide sequences, wherein the comparison comprises calculating k-mer weights as a measure of how likely it is that k-mers within the sequencing read are derived from a reference sequence within the plurality of reference polynucleotide sequences; (b) for each of the sequencing reads, calculating a probability that the sequencing read corresponds to a particular reference sequence in a database of reference sequences based on the k-mer weights, thereby generating a sequence probability; (c) calculating a score for the presence or absence of one or more taxa based on the sequence probabilities corresponding to sequences representative of said one or more taxa; and (d) identifying the one or more taxa as present or absent in the sample based on the corresponding scores.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 2A-E show performance of an embodiment of Taxonomer's 'Classifier' module for bacterial and fungal classification, as well as bacterial community profiling. Numbers below the bars indicate the reads (%) represented by the bottom bar at the corresponding position. Numbers above the bars indicate the reads (%) of the first bar above the bottom bar at the corresponding position.

FIGS. 3A-F show performance characteristics of an embodiment of Taxonomer's 'Protonomer' module for virus detection.

FIGS. 4A-H show performance characteristics of an embodiment of Taxonomer's 'Classifier' module for host transcript expression profiling.

FIGS. 5A-D illustrate results for detecting previously unrecognized infections or laboratory contamination and compatibility with commonly used sequencers.

FIGS. 16A-B illustrate results showing that an embodiment of Taxonomer was able to correctly identify *Elizabethkingia meningoseptica* in sample SAMN03015718 (SRR1564828) and Enterovirus A in plasma from a patient with suspected Ebola virus disease in Sierra Leone (SRR1564825).

FIG. 18 shows example processing times of an embodiment of Taxonomer compared to the classification pipelines SURPI and Kraken.

FIG. 19 provides example reference databases in accordance with embodiments of the disclosure.

FIG. 20 provides results of sequence comparisons performed in accordance with embodiments of the disclosure.

DETAILED DESCRIPTION OF THE INVENTION

Figure 1A:
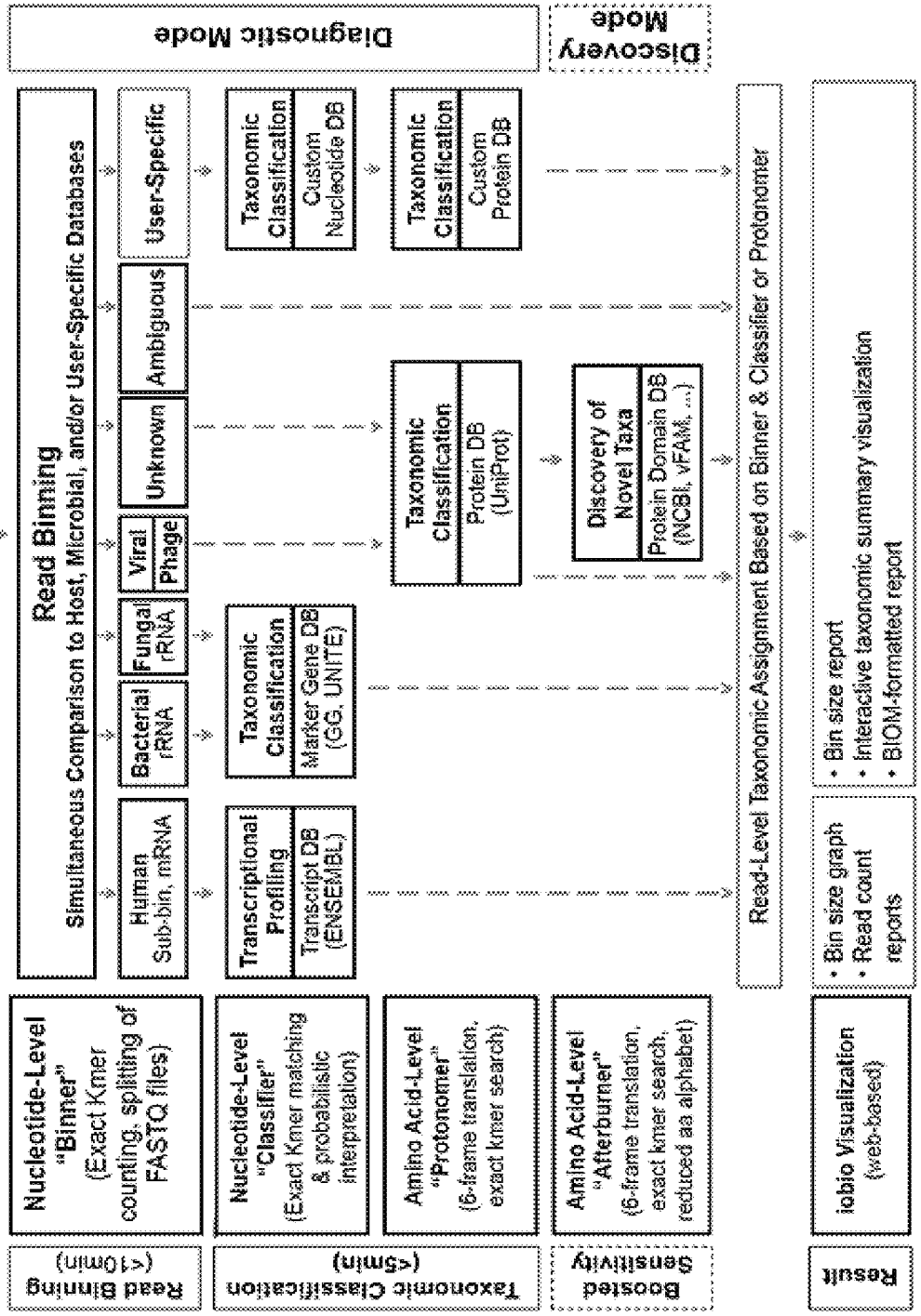
FIGS. 1A-B provide an overview of the structure and user interface of a system in accordance with an embodiment of the disclosure, referred to as Taxonomer.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The systems and methods of this disclosure as described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory*

Manual (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, N.Y. (1995); Gait, *"Oligonucleotide Synthesis: A Practical Approach"* IRL Press, London (1984); Nelson and Cox, *Lehninger, Principles of Biochemistry*, $3^{rd}$ Ed., W.H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and systems and methods are described, it is to be understood that this disclosure is not limited to the specific systems and methods, compositions, targets and uses described, as such may, of course, vary. It is also to be understood that the terminology used herein is for the purpose of describing particular aspects only and is not intended to limit the scope of the present disclosure, which will be limited only by appended claims.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

"Differentially expressed," as applied to nucleotide sequence or polypeptide sequence in a subject, refers to over-expression or under-expression of that sequence when compared to that detected in a control. Underexpression also encompasses absence of expression of a particular sequence as evidenced by the absence of detectable expression in a test subject when compared to a control.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

A "control" is an alternative subject or sample used in an experiment for comparison purpose.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "determining", "measuring", "evaluating", "assessing," "assaying," and "analyzing" can be used interchangeably herein to refer to any form of measurement, and include determining if an element is present or not (for example, detection). These terms can include both quantitative and/or qualitative determinations. Assessing may be relative or absolute. "Detecting the presence of" can include determining the amount of something present, as well as determining whether it is present or absent.

The term specificity, or true negative rate, can refer to a test's ability to exclude a condition correctly. For example, in a classification algorithm, the specificity of the algorithm may refer to the proportion of reads known not to be from an organism in a given taxonomic bin, which will not be placed in the taxonomic bin. In some cases, this is calculated by determining the proportion of true negatives (reads not placed in the bin that are not from the taxonomic bin) to the total number of reads that are not derived from an organism within the taxonomic bin (the sum of the reads that are not placed in a given taxonomic bin and are not derived from an organism within that taxonomic bin and reads that are placed in that taxonomic bin that are not derived from an organism within that taxonomic bin).

The term sensitivity, or true positive rate, can refer to a test's ability to identify a condition correctly. For example, in a classification algorithm, the sensitivity of a test may refer to the proportion of reads known to be from an organism in a given taxonomic bin, which will be placed in the taxonomic bin. In some cases, this is calculated by determining the proportion of true positives (reads placed in the bin that are from the taxonomic bin) to the total number of reads that are derived from an organism within the taxonomic bin (the sum of the reads that are placed in a given taxonomic bin and are derived from an organism within that taxonomic bin and reads that are not placed in that taxonomic bin that are derived from an organism within that taxonomic bin).

The quantitative relationship between sensitivity and specificity can change as different classification cut-offs are chosen. This variation can be represented using ROC curves. The x-axis of a ROC curve shows the false-positive rate of an assay, which can be calculated as (1—specificity). The y-axis of a ROC curve reports the sensitivity for an assay. This allows one to determine a sensitivity of an assay for a given specificity, and vice versa.

As used here, the term "adaptor" or "adapter" are used interchangeably and can refer to an oligonucleotide that may be attached to the end of a nucleic acid. Adaptor sequences may comprise, for example, priming sites, the complement of a priming site, recognition sites for endonucleases, common sequences and promoters. Adaptors may also incorporate modified nucleotides that modify the properties of the adaptor sequence. For example, phosphorothioate groups may be incorporated in one of the adaptor strands.

The terms "taxon" (plural "taxa"), "taxonomic group," and "taxonomic unit" are used interchangeably to refer to a group of one or more organisms that comprises a node in a clustering tree. The level of a cluster is determined by its hierarchical order. In one embodiment, a taxon is a group tentatively assumed to be a valid taxon for purposes of phylogenetic analysis. In another embodiment, a taxon is any of the extant taxonomic units under study. In yet another embodiment, a taxon is given a name and a rank. For example, a taxon can represent a domain, a sub-domain, a kingdom, a sub-kingdom, a phylum, a sub-phylum, a class, a sub-class, an order, a sub-order, a family, a subfamily, a genus, a subgenus, or a species. In some embodiments, taxa can represent one or more organisms from the kingdoms eubacteria, protista, or fungi at any level of a hierarchal order.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. In general, an exact match indicates 100% identity over the length of the shortest of the sequences being compared (or over the length of both sequences, if identical).

In one aspect, the disclosure provides a method of identifying a plurality of polynucleotides in a sample source. In some embodiments, the method comprises providing sequencing reads for a plurality of polynucleotides from the sample, and for each sequencing read: (a) performing with a computer system a sequence comparison between the sequencing read and a plurality of reference polynucleotide sequences, wherein the comparison comprises calculating k-mer weights as a measure of how likely it is that k-mers within the sequencing read are derived from a reference sequence within the plurality of reference polynucleotide sequences; (b) identifying the sequencing read as corresponding to a particular reference sequence in a database of reference sequences if the sum of k-mer weights for the reference sequence is above a threshold level; and (c) assembling a record database comprising reference sequences identified in step (b), wherein the record database excludes reference sequences to which no sequencing read corresponds.

In another aspect, the disclosure provides a method of identifying one or more taxa in a sample from a sample source. In some embodiments, the method comprises (a) providing sequencing reads for a plurality of polynucleotides from the sample, and for each sequencing read: (i) performing with a computer system a sequence comparison between the sequencing read and a plurality of reference polynucleotide sequences, wherein the comparison comprises calculating k-mer weights as a measure of how likely it is that k-mers within the sequencing read are derived from a reference sequence within the plurality of reference polynucleotide sequences; and (ii) calculating a probability that the sequencing read corresponds to a particular reference sequence in a database of reference sequences based on the k-mer weights, thereby generating a sequence probability; (b) calculating a score for the presence or absence of one or more taxa based on the sequence probabilities corresponding to sequences representative of said one or more taxa; and (c) identifying the one or more taxa as present or absent in the sample based on the corresponding scores. In some cases, the one or more taxa comprises a first bacterial strain identified as present and a second bacterial strain identified as absent based on one or more nucleotide differences in sequence. In some cases, the first bacterial strain is identified as present and the second bacterial strain is identified as absent based on a single nucleotide difference in sequence.

In general, a sequencing read (also referred to as a "read" or "query sequence") refers to the inferred sequence of nucleotide bases in a nucleic acid molecule. A sequencing read may be of any appropriate length, such as about or more than about 20 nt, 30 nt, 36 nt, 40 nt, 50 nt, 75 nt, 100 nt, 150 nt, 200 nt, 250 nt, 300 nt, 400 nt, 500 nt, or more in length. In some embodiments, a sequencing read is less than 200 nt, 150 nt, 100 nt, 75 nt, or fewer in length. Sequencing reads can be "paired," meaning that they are derived from different ends of a nucleic acid fragment. Paired reads can have intervening unknown sequence or overlap. In some cases, the sequencing read is a contig or consensus sequence assembled from separate overlapping reads. A sequencing read may be analyzed in terms of component k-mers. In general, "k-mer" refers to the subsequences of a given length k that make up a sequencing read. For example, a the sequence "AGCTCT" can be divided into the 3-nt subsequences "AGC," "GCT," "CTC," and "TCT." In this example, each of these subsequences is a k-mer, wherein k=3. K-mers may be overlapping or non-overlapping.

Sequence comparison may comprise one or more comparison steps in which one or more k-mers of a sequencing read are compared to k-mers of one or more reference sequences (also referred to simply as a "reference"). In some embodiments, a k-mer is about or more than about 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 75 nt, 100 nt, or more in length. In some embodiments, a k-mer is about or less than about 30 nt, 25 nt, 20 nt, 15 nt, 10 nt, or fewer in length. The k-mer may be in the range of 3 nt to 13 nt, 5 nt to 25 nt in length, 7 nt to 99 nt, or 3 nt to 99 nt in length. The length of k-mer analyzed at each step may vary. For example, a first comparison may compare k-mers in a sequencing read and a reference sequence that are 21 nt in length, whereas a second comparison may compare k-mers in a sequencing read and a reference sequence that are 7 nt in length. For any given sequence in a comparison step, k-mers analyzed may be overlapping (such as in a sliding window), and may be of same or different lengths. While k-mers are generally referred to herein as nucleic acid sequences, sequence comparison also encompasses comparison of polypeptide sequences, including comparison of k-mers consisting of amino acids.

A reference sequence includes any sequence to which a sequencing read is compared. Typically, the reference sequence is associated with some known characteristic, such as a condition of a sample source, a taxonomic group, a particular species, an expression profile, a particular gene, an associated phenotype such as likely disease progression, drug resistance or pathogenicity, increased or reduced predisposition to disease, or other characteristic. Typically, a reference sequence is one of many such reference sequences in a database. A variety of databases comprising various types of reference sequences are available, one or more of which may serve as a reference database either individually or in various combinations. Databases can comprise many species and sequence types, such as NR, UniProt, SwissProt, TrEMBL, or UniRef90. Databases can comprise specific kinds of sequences from multiple species, such as those used for taxonomic classification of species, such as bacteria. Such databases can be 16S databases, such as The Greengenes database, the UNITE database, or the SILVA database. Marker genes other than 16S may be used as reference sequences for the identification of microorganisms (e.g. bacteria), such as metabolic genes, genes encoding structural proteins, proteins that control growth, cell cycle or reproductive regulation, housekeeping genes or genes that encode virulence, toxins, or other pathogenic factors. Specific examples of marker genes include, but are not limited to, 18S rDNA, 23 S rDNA, gyrA, gyrB gene, groEL, rpoB gene, fusA gene, recA gene, sod A, coxI gene, and nifD gene. Reference databases can comprise internal transcribed sequences (ITS) databases, such as UNITE, ITSoneDB, or ITS2. Databases can comprise multiple sequences from a single species, such as the human genome, the human transcriptome, model organisms such as the mouse genome, the yeast transcriptome, or the *C. elegans* proteome, or disease vectors such as bat, tick, or mosquitoes and other domestic and wild animals. In some embodiments, the reference database comprises sequences of human transcripts. Reference sequences in databases can comprise DNA sequences, RNA sequences, or protein sequences. Reference sequences in databases can comprise sequences from a plurality of taxa. In some cases, the reference sequences are from a reference individual or a reference sample source. Examples of reference individual genomes are, for example, a maternal genome, a paternal genome, or the genome of a non-cancerous tissue sample. Examples of reference individuals or sample sources are the human genome, the mouse genome, or the genomes of particular serovars, genovars, strains, variants or otherwise characterized types of bacteria, archea, viruses, phages, fungi, and parasites. The database can comprise polymorphic reference sequences that contain one or more mutations with respect to known polynucleotide sequences. Such polymorphic reference sequences can be different alleles found in the population, such as SNPs, indels, microdeletions, microexpansions, common rearrangements, genetic recombinations, or prophage insertion sites, and may contain information on their relative abundance compared to non-polymorphic sequences. Polymorphic reference sequences may also be artificially generated from the reference sequences of a database, such as by varying one or more (including all) positions in a reference genome such that a plurality of possible mutations not in the actual reference database are represented for comparison. The database of reference sequences can comprise reference sequences of one or more of a variety of different taxonomic groups, including but not limited to bacteria, archaea, chromalveolata, viruses, fungi, plants, fish, amphibians, reptiles, birds, mammals, and humans. In some cases, the database of reference sequences consists of sequences from one or more reference individuals or a reference sample sources (e.g. 10, 100, 1000, 10000, 100000, 1000000, or more), and each reference sequence in the database is associated with its corresponding individual or sample source. In some embodiments, an unknown sample may be identified as originating from an individual or sample source represented in the reference database on the basis of a sequence comparison.

In some embodiments, each reference sequence in the database of reference sequences is associated with, prior to the comparison, a k-mer weight as a measure of how likely it is that a k-mer within the reference sequence originates from the reference sequence. Alternatively, the database of reference sequences can comprise sequences from a plurality of taxa, and each reference sequence in the database of reference sequences is associated with a k-mer weight as a measure of how likely it is that a k-mer within the reference sequence originates from a taxon within the plurality of taxa. Calculating the k-mer weight can comprise comparing a reference sequence in the database to the other reference sequences in the database, such as by a method described herein. The k-mer values thus associated with sequences or taxa in the database may then be used in determining k-mer weights for k-mers within sequencing reads.

In general, comparing k-mers in a read to a reference sequence comprises counting k-mer matches between the two. The stringency for identifying a match may vary. For example, a match may be an exact match, in which the nucleotide sequence of the k-mer from the read is identical to the nucleotide sequence of the k-mer from the reference. Alternatively, a match may be an incomplete match, where 1, 2, 3, 4, 5, 10, or more mismatches are permitted. In addition to counting matches, a likelihood (also referred to as a "k-mer weight" or "KW") can be calculated. In some embodiments, the k-mer weight relates a count of a particular k-mer within a particular reference sequence, a count of the particular k-mer among a group of sequences comprising the reference sequence, and a count of the particular k-mer among all reference sequences in the database of reference sequences. In one embodiment, the k-mer weight is calculated according to the following formula, which calculates the k-mer weight as a measure of how likely it is that a particular k-mer ($K_i$) originates from a reference sequence ($ref_i$) as follows:

$$KWref_i(K_i) = \frac{C_{ref}(K_i)/C_{db}(K_i)}{C_{db}(K_i)/\text{Total kmer count}} \quad \text{(Eqn. 1)}$$

C represents a function that returns the count of $K_i$. $C_{ref}(K_i)$ indicates the count of the $K_i$ in a particular reference. $C_{db}(K_i)$ indicates the count of $K_i$ in the database. This weight provides a relative, database specific measure of how likely it is that a k-mer originated from a particular reference. Prior to comparing a sequencing read to the database of reference sequences, the k-mer weight (or measurement of likelihood that a k-mer originates from a given reference sequence) can be calculated for each k-mer and reference sequence in the database. In some cases, when a reference databases comprises sequences from a plurality of taxa, each reference sequence can be associated with a measure of likelihood, or k-mer weight, that a k-mer within the reference sequence originates from a taxon within a plurality of taxa. As a non-limiting example, a reference database can comprise sequences from multiple species of canines, and the k-mer weight could be calculated by relating the count of a given k-mer in all canine sequences to its count in the entire database, which includes other taxa. In some examples, the k-mer weight measuring how likely it is that a k-mer originates from a specific taxon is calculated by defining $C_{ref}(K_i)$ in the above equation as a function that returns the total count of $K_i$ in a particular taxon.

For each reference sequence, reference database derived weights for a plurality of k-mers within a sequencing read may be added and compared to a threshold value. The threshold value can be specific to the collection of reference sequences in the database and may be selected based on a variety of factors, such as average read length, whether a specific sequence or source organism is to be identified as present in the sample, and the like. If the sum of k-mer weights for the reference sequence is above the threshold level, the sequencing read may be identified as corresponding to the reference sequence, and optionally the organism or taxonomic group associated with the reference sequence. In some cases, the read is assigned to the reference sequence with the maximum sum of k-mer weights, which may or may not be required to be above a threshold. In the case of a tie, where a sequence read has an equal likelihood of belonging to more than one reference sequence as measured by k-mer weight, the sequence read can be assigned to the taxonomic lowest common ancestor (LCA) taking into account the read's total k-mer weight along each branch of the phylogenetic tree. In general, correspondence with a reference sequence, organism, or taxonomic group indicates that it was present in the sample.

In some aspects, the methods comprise calculating a probability. In some cases, a probability is calculated for a sequencing read generated from a plurality of polynucleotides. In some cases, the probability is the probability (or likelihood) that the sequencing read corresponds to a particular reference sequence in a database of reference sequences based on the k-mer weights. A probability may be calculated for each sequencing read, thereby generating a plurality of sequence probabilities. In some cases, the presence or absence of one or more taxa in a sample may be determined based on the sequence probabilities. For example, the probability may identify a first bacterial strain as being present in the sample and a second bacterial strain as being absent in the sample. In some cases, the probability is represented as a percentage (%) or as a fraction. In some cases, a probability is provided as a score representative of the probability. The score can be based on any arbitrary scale so long as the score is indicative of the probability (e.g. a probability that an individual sequence corresponds to a particular reference sequence, or a probability that a particular taxon is present in the sample). The probability or a score representative of the probability may be used to determine the presence or absence of one or more taxa within a sample. For example, a probability or score above a threshold value may be indicative of presence, and/or a probability or score below a threshold value may be indicative of absence. In some embodiments, presence or absence is reported as a probability, rather than an absolute call. Example methods for calculating such probabilities are provided herein. In general, embodiments described herein in terms of presence or absence likewise encompass calculating a probability or score for such presence or absence.

Results of methods described herein will typically be assembled in a record database. In some embodiments, the record database comprises reference sequences identified as present in the sample and excludes reference sequences to which no sequencing read was found to correspond, such as by failure to match a sequencing read above a set threshold level. The software routines used to generate the sequence record database and to compare sequencing reads to the database can be run on a computer. The comparison can be performed automatically upon receiving data. The comparison can be performed in response to a user request. The user request can specify which reference database to compare the sample to. The computer can comprise one or more processors. Processors may be associated with one or more controllers, calculation units, and/or other units of a computer system, or implanted in firmware as desired. If implemented in software, the routines may be stored in any computer readable memory, such as in RAM, ROM, flash memory, a magnetic disk, a laser disk, or other storage medium. The record database, sequencing reads, or a report summarizing the results of database construction or sequence read comparison may also be stored in any suitable medium, such as in RAM, ROM, flash memory, a magnetic disk, a laser disk, or other storage medium. Likewise, the record database, sequencing reads, or a report summarizing the results of database construction or sequence read comparison may be delivered to a computing device via any known delivery method including, for example, over a communication channel such as a telephone line, the internet, a wireless connection, etc., or via a transportable medium, such as a computer readable disk, flash drive, etc. . . . . A database, sequencing reads, or report may be communicated to a user at a local or remote location using any suitable communication medium. For example, the communication medium can be a network connection, a wireless connection, or an internet connection. A database or report can be transmitted over such networks or connections (or any other suitable means for transmitting information, including but not limited to mailing database summary, such as a print-out) for reception and/or for review by a user. The recipient can be but is not limited to the customer, an individual, a health care provider, a health care manager, or electronic system (e.g. one or more computers, and/or one or more servers). In some embodiments, the database or report generator sends the report to a recipient's device, such as a personal computer, phone, tablet, or other device. The database or report may be viewed online, saved on the recipient's device, or printed. The comparison of communicated sequencing reads to a database can occur after all the reads are uploaded. The comparison of communicated sequencing reads to a database can begin while the sequencing reads are in the process of being uploaded.

One or more steps of a method described herein may be performed in parallel for each of the plurality of sequencing reads. For example, each of the sequencing reads in the plurality may be subjected in parallel to a first sequence comparison between the sequencing read and a plurality of reference polynucleotide sequences (e.g. reference polynucleotide sequences from a plurality of different taxa and/or a plurality of different reference databases). Comparison in parallel differs from certain stepwise comparison processes in that sequencing reads having a purported match in a first reference database are not subtracted from the query set of sequences for subsequent comparison with a second reference database. In such a stepwise process, sequences having a purported match in the first database may be incorrectly identified before comparison being run against a reference database containing a more accurate match (e.g. the correct sequence). Instead, by running a comparison against a plurality of different reference sequences corresponding to a plurality of different taxa, each sequence can be assigned to an optimal first taxonomic class prior to identifying with greater specificity a sequence or taxon to which a sequencing read corresponds. For example, sequencing reads may be first classified as corresponding to human, bacterial, or fungal sequences before identifying a particular gene, bacterial species, or fungal species to which the sequencing read corresponds. In some instances, this process is referred to as "binning." Parallel sequence comparison may comprise comparison with sequences from two or more different taxonomic groups, such as 3, 4, 5, 6, or more different taxonomic groups. In some embodiments, the different taxonomic groups may be selected from two or more of the following bacteria, archaea, chromalveolata, viruses, fungi, plants, fish, amphibians, reptiles, birds, mammals, and humans.

In some embodiments, a method may further comprise quantifying an amount of polynucleotides corresponding to a reference sequence identified in an earlier step. Quantification can be based on a number of corresponding sequencing reads identified. This can include normalizing the count by the total number of reads, the total number of reads associated with sequences, the length of the reference sequence, or a combination thereof. Examples of such normalization include FPKM and RPKM, but may also include other methods that take into account the relative amount of reads in different samples, such as normalizing sequencing reads from samples by the median of ratios of observed counts per sequence. A difference in quantity between samples can indicate a difference between the two samples. The quantitation can be used to identify differences between subjects, such as comparing the taxa present in the microbiota of subjects with different diets, or to observe changes in the same subject over time, such as observing the taxa present in the microbiota of a subject before and after going on a particular diet.

In some embodiments, a method may comprise determining the presence, absence, or abundance of specific taxa or nucleotide polymorphisms within samples based on results of an earlier step. In this case, the plurality of reference polynucleotide sequences typically comprise groups of sequences corresponding to individual taxa in the plurality of taxa. In some cases, at least 50, 100, 250, 500, 1000, 5000, 10000, 50000, 100000, 250000, 500000, or 1000000 different taxa are identified as absent or present (and optionally abundance, which may be relative) based on sequences analyzed by a method described herein. In some cases, this analysis is performed in parallel. In some embodiments, the methods, compositions, and systems of the present disclosure enable parallel detection of the presence or absence of a taxon in a community of taxa, such as an environmental or clinical sample, when the taxon identified comprises less than one per $10^9$, or one per $10^6$, or 0.05% of the total population of taxa in the source sample. In some cases, detection is based on sequencing reads corresponding to a polynucleotide that is present at less than 0.01% of the total nucleic acid population. The particular polynucleotide may be at least 20%, 30%, 40%, 50%, 60%, 70%, 80%, 85%, 90%, 91%, 92%, 93%, 94%, 95%, 96% or 97% homologous to other nucleic acids in the population. In some cases, the particular polynucleotide is less than 75%, 50%, 40%, 30%, 20%, or 10% homologous to other nucleic acids in the population. Determining the presence, absence, or abundance of specific taxa can comprise identifying an individual subject as the source of a sample. For example, a reference database may comprise a plurality of reference sequences, each of which corresponds to an individual organism (e.g. a human subject), with sequences from a plurality of different subject represented among the reference sequences. Sequencing reads for an unknown sample may then be compared to sequences of the reference database, and based on identifying the sequencing reads in accordance with a described method, an individual represented in the reference database may be identified as the sample source of the sequencing reads. In such a case, the reference database may comprise sequences from at least $10^2$, $10^3$, $10^4$, $10^5$, $10^6$, $10^7$, $10^8$, $10^9$, or more individuals.

In some cases, a sequencing read does not have a match to a reference sequence at the level of a particular taxonomic group (e.g. at the species level), or at any taxonomic level. When no match is found, the corresponding sequence may be added to a reference database on the basis of known characteristics. In some cases, when a sequence is identified as belonging to a particular taxon in the plurality of taxa, and is not present among the group of sequences corresponding to that taxon, it is added to the group of sequences corresponding to the taxon for use in later sequence comparisons. For example, if a bacterial genome is identified as belonging to a particular taxon, such as a genus or family, but the genome comprises sequence that is not present in the sequences associated with that taxon, the bacterial genome can be added to the sequence database. Likewise, if the sample is derived from a particular source or condition, the sequencing read may be added to a reference database of sequences associated with that source or condition for use in identifying future samples that share the same source or condition. As a further example, a sequence that does not have a match at a lower level but does have a match at a higher level, as identified according to a method described herein, may be assigned to that higher level while also adding the sequencing read to the plurality of reference sequences that correspond to that taxonomic group. Reference databases so updated may be used in later sequence comparisons.

In determining the presence, absence or abundance of a taxon in a plurality of taxa (or polymorphism among a plurality of polymorphisms), two possible taxa may be tied for the assignment of a particular sequencing read. In such cases, the tie may be resolved. In one example, a tie is resolved by determining a sum of k-mer weights for the reference sequences along each branch of a phylogenetic tree connecting the taxa. The sequencing read may then be assigned to the node connected to the branch with the highest sum of k-mer weights.

A reference database can consist of sequences (and optionally abundance levels of sequences) associated with one or more conditions. Multiple conditions may be represented by one or more sequences in the reference database, such as 10, 50, 100, 1000, 10000, 100000, 1000000, or more conditions. For example, a reference database may consist of thousands of groups of sequences, each group of sequences being associated with a different bacterial contaminant, such that contamination of a sample by any of the represented bacteria may be detected by sequence comparison according to a method of the disclosure. A condition can be any characteristic of a sample or source from which a sample is derived. For example, the reference database may consist of a set of genes that are associated with contamination by microorganisms, infection of a subject from which the sample is derived, or a host response to pathogens. Other conditions include, but are not limited to, contamination (e.g. environmental contamination, surface contamination, food contamination, air contamination, water contamination, cell culture contamination), stimulus response (e.g. drug responder or non-responder, allergic response, treatment response), infection (e.g. bacterial infection, fungal infection, viral infection), disease state (e.g. presence of disease, worsening of disease, disease recovery), and a healthy state.

Where the reference database consists of sequences associated with infectious disease or contamination, the sequences may be derived from and associated with any of a variety of infectious agents. The infectious agent can be bacterial. Non-limiting examples of bacterial pathogens include *Mycobacteria* (e.g. *M. tuberculosis*, *M. bovis*, *M. avium*, *M. leprae*, and *M. africanum*), *rickettsia*, *mycoplasma*, *chlamydia*, and *legionella*. Other examples of bacterial infections include, but are not limited to, infections caused by Gram positive *bacillus* (e.g., *Listeria*, *Bacillus* such as *Bacillus anthracis*, *Erysipelothrix* species), Gram negative *bacillus* (e.g., *Bartonella*, *Brucella*, *Campylobacter*, *Enterobacter*, *Escherichia*, *Francisella*, *Hemophilus*, *Klebsiella*, *Morganella*, *Proteus*, *Providencia*, *Pseudomonas*, *Salmonella*, *Serratia*, *Shigella*, *Vibrio* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, and *Neisseria* species. Specific examples of infectious bacteria include, but are not limited to: *Helicobacter pyloris*, *Legionella pneumophilia*, *Mycobacteria tuberculosis*, *M. avium*, *M. intracellular e*, *M. kansaii*, *M. gordonae*, *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus viridans*, *Streptococcus faecalis*, *Streptococcus bovis*, *Streptococcus pneumoniae*, *Haemophilus influenzae*, *Bacillus antracis*, *Erysipelothrix rhusiopathiae*, *Clostridium tetani*, *Enterobacter aerogenes*, *Klebsiella pneumoniae*, *Pasteurella multocida*, *Fusobacterium nucleatum*, *Streptobacillus moniliformis*, *Treponema pallidium*, *Treponema pertenue*, *Leptospira*, *Rickettsia*, and *Actinomyces israelii*, *Acinetobacter*, *Bacillus*, *Bordetella*, *Borrelia*, *Brucella*, *Campylobacter*, *Chlamydia*, *Chlamydophila*, *Clostridium*, *Corynebacterium*, *Enterococcus*, *Haemophilus*, *Helicobacter*, *Mycobacterium*, *Mycoplasma*, *Stenotrophomonas*, *Treponema*, *Vibrio*, *Yersinia*, *Acinetobacter baumanii*, *Bordetella pertussis*, *Brucella abortus*, *Brucella canis*, *Brucella melitensis*, *Brucella suis*, *Campylobacter jejuni*, *Chlamydia pneumoniae*, *Chlamydia trachomatis*, *Chlamydophila psittaci*, *Clostridium botulinum*, *Clostridium difficile*, *Clostridium perfringens*, *Corynebacterium diphtheriae*, *Enterobacter sazakii*, *Enterobacter agglomerans*, *Enterobacter cloacae*, *Enterococcus faecalis*, *Enterococcus faecium*, *Escherichia coli*, *Francisella tularensis*, *Helicobacter pylori*, *Legionella pneumophila*, *Leptospira interrogans*, *Mycobacterium leprae*, *Mycobacterium tuberculosis*, *Mycobacterium ulcerans*, *Mycoplasma pneumoniae*, *Pseudomonas aeruginosa*, *Rickettsia rickettsii*, *Salmonella typhi*, *Salmonella typhimurium*, *Salmonella enterica*, *Shigella sonnei*, *Staphylococcus epidermidis*, *Staphylococcus saprophyticus*, *Stenotrophomonas maltophilia*, *Vibrio cholerae*, *Yersinia pestis*, and the like.

Sequences in the reference database may be associated with viral infectious agents. Non-limiting examples of viral pathogens include the herpes virus {e.g., human cytomegalomous virus (HCMV), herpes simplex virus 1 (HSV-1), herpes simplex virus 2 (HSV-2), varicella zoster virus (VZV), Epstein-Barr virus), influenza A virus and Hepatitis C virus (HCV) (see Munger et al, Nature Biotechnology (2008) 26: 1179-1186; Syed et al, Trends in Endocrinology and Metabolism (2009) 21:33-40; Sakamoto et al, Nature Chemical Biology (2005) 1:333-337; Yang et al, Hepatology (2008) 48: 1396-1403) or a picomavirus such as Coxsackievirus B3 (CVB3) (see Rassmann et al, Anti-viral Research (2007) 76: 150-158). Other exemplary viruses include, but are not limited to, the hepatitis B virus, HIV, poxvirus, hepadnavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In certain embodiments, the virus is an enveloped virus. Examples include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses A1-22, 24 (CA1-22 and CA24, CA23 (echovirus 9)), human coxsackieviruses (B1-6 (CB1-6)), human echoviruses 1-7, 9, 11-27, 29-33, vilyuish virus, simian enteroviruses 1-18 (SEV1-18), porcine enteroviruses 1-11 (PEV1-11), bovine enteroviruses 1-2 (BEV1-2), hepatitis A virus, rhinoviruses, hepatoviruses, cardio viruses, aphthoviruses and echoviruses. The virus may be phage. Examples of phages include, but are not limited to T4, T5, λ phage, T7 phage, G4, P1, φ6, *Thermoproteus tenax* virus 1, M13, MS2, Qβ, φX174, Φ29, PZA, Φ15, BS32, B103, M2Y (M2), Nf, GA-1, FWLBc1, FWLBc2, FWLLm3, B4. The reference database may comprise sequences for phage that are pathogenic, protective, or both. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalo-myelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O'nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively).

Infectious agents with which sequences in the reference database may be associated can be fungal. Examples of infectious fungal infectious agents include, without limitation *Aspergillus, Blastomyces, Coccidioides, Cryptococcus, Histoplasma, Paracoccidioides, Sporothrix*, and at least three genera of Zygomycetes. Secondary infections that can worsen diaper rash include fungal organisms (for example yeasts of the genus *Candida*). The above fungi, as well as many other fungi, can cause disease in pets and companion animals. The present teaching is inclusive of substrates that contact animals directly or indirectly. Examples of organisms that cause disease in animals include *Malassezia furfur, Epidermophyton floccosur, Trichophyton mentagrophytes,* *Trichophyton rubrum, Trichophyton tonsurans, Trichophyton equinum, Dermatophilus congolensis, Microsporum canis, Microsporu audouinii, Microsporum gypseum, Malassezia ovale, Pseudallescheria, Scopulariopsis, Scedosporium,* and *Candida albicans*. Further examples of fungal infectious agent include, but are not limited to, *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus,* or *Rhizopus arrhizus*.

Another example of infectious agents with which sequences in a reference database may be associated are parasites. Non-limiting examples of parasites include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp.

The reference database may combine sequences associated with different infectious agents (e.g. reference sequences associated with infection by a variety of bacterial agents, a variety of viral agents, and a variety of fungal agents). Moreover, the reference database may comprise sequences identified as originating from a pathogen that has not yet been identified or classified.

Reference sequences associated with a condition also include genetic markers for drug resistance, pathogenicity, and disease. A variety of disease-associated markers are known, which may be represented in the reference database. A disease-associated marker may be a causal genetic variant. In general, causal genetic variants are genetic variants for which there is statistical, biological, and/or functional evidence of association with a disease or trait. A. single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), mter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epi genetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants are known in the art. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Additional non-limiting examples of causal genetic variants are described in WO2014015084A2 and US20100022406. Examples of drug resistance markers include enzymes conferring resistance to various aminoglycoside antibiotics such as G418 and neomycin (e.g., an aminoglycoside 3'-phosphotransferase, 3'APH II, also known as neomycin phosphotransferase II (nptII or "neo")), Zeocin™ or bleomycin (e.g., the protein encoded by the ble gene from *Streptoalloteichus hindustanus*), hygromycin (e.g., hygromycin resistance gene, hph, from *Streptomyces hygroscopicus* or from a plasmid isolated from *Escherichia coli* or *Klebsiella pneumoniae*, which codes for a kinase (hygromycin phosphotransferase, HPT) that inactivates Hygromycin B through phosphorylation), puromycin (e.g., the *Streptomyces alboniger* puromycin-N-acetyl-transferase (pac) gene), or blasticidin (e.g., an acetyl transferase encoded by the bls gene from *Streptoverticillum* sp. JCM 4673, or a deaminase encoded by a gene such as bsr, from *Bacillus cereus* or the BSD resistance gene from *Aspergillus terreus*). Other exemplary drug resistance markers are dihydrofolate reductase (DHFR), adenosine deaminase (ADA), thymidine kinase (TK), and hypoxanthine-guanine phosphoribosyltransferase (HPRT). Proteins such as P-glycoprotein and other multidrug resistance proteins act as pumps through which various cytotoxic compounds, e.g., chemotherapeutic agents such as vinblastine and anthracyclines, are expelled from cells. Exemplary markers of pathogenicity include: factors involved in outer-membrane protein expression, microbial toxins, factors involved in biofilm formation, factors involved in carbohydrate transport and metabolism, factors involved in cell envelope synthesis, and factors involved in lipid metabolism. Exemplary markers of pathogenicity can include, but are not limited to gp120, ebola virus envelope protein, or other glycosylated viral envelope proteins or viral proteins.

The reference database may consist of host expression profiles associated with a healthy state and/or one or more disease states, in which certain combinations of expressed genes (or levels of expression of particular genes) identify a condition of a subject. The groups of genes may be overlapping. The reference database consisting of sequences associated with a condition may comprise both host expression profiles and groups of sequences associated with other conditions (e.g. reference sequences associated with various infectious agents).

In cases where the reference database consists of sequences associated with a condition, the method may comprise identifying the condition in the sample or the source from which the sample is derived. The condition may be identified based on the presence or change in 10%, 20%, 30%, 40%, 50%, 60%, 70%, 80%, 90%, or 100% of the components of a biosignature. Alternatively, a condition may be identified based on the presence or change in less than 20%, 10%, 1%, 0.1%, 0.01%, 0.001%, 0.0001%, or 0.00001% of the components of a biosignature. In some embodiments, a sample is identified as affected by the condition if at least 80% of the sequences and/or taxa associated with the condition are identified as present (or present at a level associated with the condition). In some embodiments, the sample is identified as affected by the condition if at least 90%, 95%, 99%, or all sequences or taxa (or quantities of these) associated with the condition are present. Where the condition is one of being from a particular individual, such as an individual subject (e.g. a human in a database of sequences from a plurality of different humans), identifying the sample as being affected by the condition comprises identifying the sample as being from the individual to whom the sequences in the database correspond. In some embodiments, identifying a subject as the source of the sample is based on only a fraction of the subject's genomic sequence (e.g. less than 50%, 25%, 10%, 5%, or less).

The presence, absence, or abundance of particular sequences, polymorphisms, or taxa can be used for diagnostic purposes, such as inferring that a sample or subject has a particular condition (e.g. an illness), has had a particular condition, or is likely to develop a particular condition if sequence reads associated with the condition (e.g. from a particular disease-causing organism) are present at higher levels than a control (e.g. an uninfected individual). In another embodiment, the sequencing reads can originate from the host and indicate the presence of a disease-causing organism by measuring the presence, absence, or abundance of a host gene in a sample. The presence, absence, or abundance can be used to determine the need for a treatment or care intensity, inform the choice of a treatment, infer effectiveness of a treatment, wherein a decrease in the number of sequencing reads from a disease-causing agent after treatment, or a change in the presence, absence, or abundance of specific host-response genes, indicates that a treatment is effective, whereas no change or insufficient change indicates that the treatment is ineffective. The sample can be assayed before or one or more times after treatment is begun. In some examples, the treatment of the infected subject is altered based on the results of the monitoring.

In some cases, one or more samples (e.g. blood, plasma, other body fluids, tissues, swab samples etc.) having a known condition may be used to establish a biosignature for that condition. The biosignature may be established by associating the record database with the condition. The condition can be any condition described herein. For example, a plurality of samples from a particular environmental source may be used to identify sequences and/or taxa associated with that environmental source, thereby establishing a biosignature consisting of those sequences and/or taxa so associated. In general, the term "biosignature" is used to refer to an association of the presence, absence, or abundance of a plurality of sequences and/or taxa with a particular condition, such as a classification, diagnosis, prognosis, and/or predicted outcome of a condition in a subject; a sample source; contamination by one or more contaminants; or other condition. A biosignature may be used as a reference database associated with a condition for the identification of that condition in another sample. In one embodiment, the establishing the biosignature comprises a determination of the presence, absence, and/or quantity of at least 10, 50, 100, 1000, 10000, 100000, 1000000, or more sequences and/or taxa in a sample using a single assay. Establishing a biosignature may comprise comparing sequencing reads for one or more samples representative of the condition with one or more samples not representative of the condition. For example, a biosignature can consist of gene expression involved in a host response (e.g. an immune response) among individuals infected by a virus, which sequences may be compared to sequences from subjects that are not infected or are infected by some other agent (e.g. bacteria). In such case, the presence, absence, or abundance of particular sequencing reads may be associated with a viral rather than a bacterial infection. In another example, the biosignature can consist of sequences of genes involved in a variety of antiviral responses, the presence, absence, or abundance of sequencing reads associated with which can be indicative of a specific class or type of viral infection. In some embodiments, the biosignature associated with a reference database consists of the sequences (and optionally levels) of host transcripts and/or the sequences (and optionally levels) of transcripts or genomes of one or more infectious agents. In one particular example, the condition is influenza infection and the biosignature consists of sequences of one or more of (e.g. 1, 2, 3, 4, 5, 6, 7, 8, 9, 10, 11, 12, or all of) IFIT1, IFI6, IFIT2, ISG15, OASL, IFIT3, NT5C3A, MX2, IFITM1, CXCL10, IFI44L, MX1, IFIH1, OAS2, SAMD9, RSAD2, and DDX58. In another example, the reference database could be common mutations or gene fusions found in cancerous cells, and the presence, absence, or abundance of sequencing reads associated with the biosignature can indicate that the patient has or does not have detectable cancer, what type of cancer a detectable cancer is, a preferred treatment method, whether existing treatment is effective, and/or prognosis.

In another example, the reference database can comprise sequences associated with contamination, such as polynucleotide and/or amino acid sequences from food contaminants, surface contaminants, or environmental contaminants. Examples of common food contaminants are *Escherichia coli, Clostridium botulinum, Salmonella, Listeria,* and *Vibrio cholerae.* Examples of surface contaminants are *Escherichia coli, Clostridium botulinum, Salmonella, Listeria, Vibrio cholerae,* influenza virus, methicillin-resistant *Staphylococcus aureus,* vancomycin-resistant Enterococci, *Pseudomonas* spp., *Acinetobacter* spp., *Clostridium difficile,* and norovirus. Examples of environmental contaminants are fungi such as *Aspergillus* and *Wallemia sebi*; chromalveolata such as dinoflagellates; amoebae; viruses; and bacteria. Contaminants may be infectious agents, examples of which are provided herein.

In some cases, the database of references sequence comprises polynucleotide sequences reverse-translated from amino acid sequences. In this context, translation refers to the process of using the codon code to determine an amino acid sequence from a nucleotide sequence. The standard codon code is degenerate, such that multiple three-nucleotide codons encode the same amino acid. As such, reverse-translation often produces a variety of possible sequences that could encode a particular amino acid sequence. In some embodiments, to simplify this process, reverse-translation can use a non-degenerate code, such that each amino acid is only represented by a single codon. For example, in the standard DNA codon system, phenylalanine is encoded by "TTT" and "TTC." A non-degenerate code would only associate one of the codons with phenylalanine. A sequencing read can be compared to this non-degenerate, reverse-translated sequence by any of the methods described herein. Furthermore, the sequencing read can be translated into all six reading-frames and reverse-translated using the same non-degenerate code to generate six polynucleotides that do not include alternate codons prior to comparing. By reverse-translating a reference amino acid sequence, and comparing it to sequencing reads translated then reverse-translated using the same reverse-translation code, nucleic acid sequences may be analyzed in the protein space.

Comparing sequences in accordance with a method of the disclosure can provide a variety of benefits. For example, computational resources used in the performance of a method may be substantially decreased relative to a reference method, such as a method based on traditional sequence alignment. For example the speed with which a plurality of sequences in a sample are identified may be substantially increased. In some embodiments, identifying sequencing reads as corresponding to a particular reference sequence in a database of reference sequences may be completed for 20,000 sequences in less than 1.5 seconds. In some embodiments, at least about 500000, 1000000, 2000000, 3000000, 4000000, 5000000, 10000000, or more sequences are identified per minute. The set of sequences and processor used for benchmarking sequence identification processivity may be any that are described herein. In some embodiments, the sequencing reads used for benchmarking comprise sequences from two or more of bacteria, viruses, fungi, and humans. Performance of a method described herein may be defined relative to a reference tool, such as SURPI (see e.g. Naccache, S. N. et al. A cloud-compatible bioinformatics pipeline for ultrarapid pathogen identification from next-generation sequencing of clinical samples. Genome research 24, 1180-1192 (2014)) or Kraken (see e.g. Wood, D. E. & Salzberg, S. L. Kraken: ultrafast metagenomic sequence classification using exact alignments. Genome biology 15, R46 (2014)). In some embodiments, a method of the disclosure is at least 5-fold, 10-fold, 50-fold, 100-fold, 250-fold or more faster than SURPI in reaching results that are at least as accurate as SURPI using the same data set and computer hardware. In some embodiments, a method of the present disclosure provides improved accuracy relative to a reference analysis tool. For example, accuracy may be improved by at least 5%, 6%, 7%, 8%, 9%, 10%, 15%, 20%, 25%, or more, using the same data set and computer hardware. In some embodiments, sequences and/or taxa present in a known sample are identifies with an accuracy of at least about 80%, 85%, 90%, 95%, 96%, 97%, 98%, 99%, or higher. In some embodiments, the methods provided herein are operable to distinguish between two or more different polynucleotides based on only a few sequence differences. For example, methods provided herein may be utilized to distinguish between two or more strains of taxa (e.g. bacterial strains) based on a low degree of sequence variation between the compared taxa. In some embodiments, one or more taxa comprise a first bacterial strain identified as present and a second bacterial strain identified as absent based on one or more nucleotide differences in sequence (e.g. 1, 2, 3, 4, 5, 6, 7, 8, 9, 10, 25, 50, or more differences). In some embodiments, taxa are distinguished based on fewer than 25, 10, 5, 4, 3, 2, or fewer sequence differences. In some embodiments, the first bacterial strain is identified as present and the second bacterial strain is identified as absent based on a single nucleotide difference in sequence (e.g. a SNP).

Sequencing data for analysis may be provided by a user, which may have been produced by any suitable means. Sequencing data may also be generated by isolating polynucleotides from a sample and sequencing a plurality of the polynucleotides. Samples from which polynucleotides may be derived for analysis by the present methods and systems can be from any of a variety of sources. Non-limiting examples of sample sources include environmental sources, industrial sources, one or more subjects, and one or more populations of microbes. Examples of environmental sources include, but are not limited to agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. Polynucleotides may be isolated from chromalveolata such as malaria, and dinoflagellates. Examples of subjects from which polynucleotides may be isolated include multicellular organisms, such as fish, amphibians, reptiles, birds, and mammals. Examples of mammals include be primates (e.g., apes, monkeys, gorillas), rodents (e.g., mice, rats), cows, pigs, sheep, horses, dogs, cats, or rabbits. In preferred embodiments, the mammal is a human. In some cases, the sample is an individual subject. A sample may comprise a sample from a subject, such as whole blood; blood products; red blood cells; white blood cells; buffy coat; swabs; urine; sputum; saliva; semen; lymphatic fluid; amniotic fluid; cerebrospinal fluid; peritoneal effusions; pleural effusions; biopsy samples; fluid from cysts; synovial fluid; vitreous humor; aqueous humor; bursa fluid; eye washes; eye aspirates; plasma; serum; pulmonary lavage; lung aspirates; animal, including human, tissues, including but not limited to, liver, spleen, kidney, lung, intestine, brain, heart, muscle, pancreas, cell cultures, as well as lysates, extracts, or materials and fractions obtained from the samples described above or any cells and microorganisms and viruses that may be present on or in a sample. A sample may comprise cells of a primary culture or a cell line. Examples of cell lines include, but are not limited to 293-T human kidney cells, A2870 human ovary cells, A431 human epithelium, B35 rat neuroblastoma cells, BHK-21 hamster kidney cells, BR293 human breast cells, CHO chinese hamster ovary cells, CORL23 human lung cells, HeLa cells, or Jurkat cells. The sample may comprise a homogeneous or mixed population of microbes, including one or more of viruses, bacteria, protists, monerans, chromalveolata, archaea, or fungi. Examples of viruses include, but are not limited to human immunodeficiency virus, ebola virus, rhinovirus, influenza, rotavirus, hepatitis virus, West Nile virus, ringspot virus, mosaic viruses, herpesviruses, lettuce big-vein associated virus. Non-limiting examples of bacteria include *Staphylococcus aureus, Staphylococcus aureus Mu3; Staphylococcus epidermidis, Streptococcus agalactiae, Streptococcus pyogenes, Streptococcus pneumonia, Escherichia coli, Citrobacter koseri, Clostridium perfringens, Enterococcus faecalis, Klebsiella pneumonia, Lactobacillus acidophilus, Listeria monocytogenes, Propionibacterium granulosum, Pseudomonas aeruginosa, Serratia marcescens, Bacillus cereus Staphylococcus aureus Mu50 Yersinia enterocolitica Staphylococcus simulans Micrococcus luteus* and *Enterobacter aerogenes* Examples of fungi include, but are not limited to *Absidia corymbifera, Aspergillus niger, Candida albicans, Geotrichum candidum, Hansenula anomala, Microsporum gypseum, Monilia, Mucor, Penicilliusidia corymbifera, Aspergillus niger, Candida albicans, Geotrichum candidum, Hansenula anomala, Microsporum gypseum, Monilia, Mucor, Penicillium expansum, Rhizopus, Rhodotorula, Saccharomyces bayabus, Saccharomyces carlsbergensis, Saccharomyces uvarum*, and *Saccharomyces cerivisiae*. A sample can also be processed samples such as preserved, fixed and/or stabilised samples. A sample can comprise or consist essentially of RNA. A sample can comprise or consist essentially of DNA. In some embodiments, cell-free polynucleotides (e.g. cell-free DNA and/or cell-free RNA) are analyzed. In general, cell-free polynucleotides are extracellular polynucleotides present in a sample (e.g. a sample from which cells have been removed, a sample that is not subjected to a lysis step, or a sample that is treated to separate cellular polynucleotides from extracellular polynucleotides). For example, cell-free polynucleotides include polynucleotides released into circulation upon death of a cell, and are isolated as cell-free polynucleotides from the plasma fraction of a blood sample.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent with or without the use of an automated nucleic acid extractor, e.g., the Model 341 DNA Extractor available from Applied Biosystems (Foster City, Calif.); (2) stationary phase adsorption methods; and (3) salt-induced nucleic acid precipitation methods, such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads. In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical The extracted polynucleotides from the samples can be sequenced to genereate sequencing reads. Exemplary sequencing techniques can include, for example emulsion PCR (pyrosequencing from Roche 454, semiconductor sequencing from Ion Torrent, SOLiD sequencing by ligation from Life Technologies, sequencing by synthesis from Intelligent Biosystems), bridge amplification on a flow cell (e.g. Solexa/Illumina), isothermal amplification by Wildfire technology (Life Technologies) or rolonies/nanoballs generated by rolling circle amplification (Complete Genomics, Intelligent Biosystems, Polonator). Sequencing technologies like Heliscope (Helicos), SMRT technology (Pacific Biosciences) or nanopore sequencing (Oxford Nanopore) allow direct sequencing of single molecules without prior clonal amplification may be suitable sequencing platforms. Sequencing may be performed with or without target enrichment. In some cases, polynucleotides from a sample are amplified by any suitable means prior to and/or during sequencing.

As an example, DNA sequencing technology that is used in the disclosed methods can be the Helicos True Single Molecule Sequencing (tSMS) (e.g. as described in Harris T. D. et al., Science 320:106-109 [2008]). In a typical tSMS process, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step.

Another example process for sequencing polynucleotides is 454 sequencing (Roche) (e.g. as described in Margulies, M. et al. Nature 437:376-380 (2005)). In a first step, DNA is typically sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

A further example of suitable DNA sequencing technology is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

DNA sequencing may be by single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospholinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

The DNA sequencing technology that used in the disclosed methods may be nanopore sequencing (e.g. as described in Soni GV and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the disclosed methods is the chemical-sensitive field effect transistor (chemFET) array (see e.g. US20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a suitable DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

In one aspect, the disclosure provides a method of detecting a plurality of taxa in a sample. In one embodiment, the method comprises providing sequencing reads for a plurality of polynucleotides from the sample, and for each sequencing read: (a) assigning the sequencing read to a first taxonomic groups based on a first sequence comparison between the sequencing read and a first plurality of polynucleotide sequences from the different first taxonomic groups, wherein at least two sequencing reads are assigned to different taxonomic groups; (b) performing with a computer system a second sequence comparison between the sequencing read and a second plurality of polynucleotide sequences corresponding to members of the first taxonomic group, wherein the comparison comprises counting a number of k-mers within the sequencing read of at least 5 nucleotides in length that exactly match one or more k-mers within a reference sequence in the second plurality of polynucleotide sequences; (c) classifying the sequencing read as belonging to a second taxonomic group that is more specific than the first taxonomic group if a measure of similarity between the sequencing read and reference sequence is above a first threshold level; (d) if no similarity above the first threshold level is identified in (c), classifying the sequencing read as belonging to the second taxonomic group based on similarity above a second threshold level determined by comparing with the computer system a sequence derived from translating the sequencing read and a third set of reference sequences corresponding to amino acid sequences of members of the first taxonomic group; and (e) identifying the presence, absence, or abundance of the plurality of taxa in the sample based on the classifying of the sequencing reads. In some cases, a sequencing read may be identified as corresponding to a particular reference sequence, such as a gene transcript, if the measure of similarity between the sequencing read and reference sequence is above the first threshold level.

Sequence comparison may comprise any method of sequence comparison described herein. In some embodiments, sequence comparison comprises one or more comparison steps in which one or more k-mers of a sequencing read are compared to k-mers of one or more reference sequences (also referred to simply as a "reference"). In some embodiments, a k-mer is about or more than about 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 25 nt, 30 nt, 35 nt, 40 nt, 45 nt, 50 nt, 75 nt, 100 nt, or more in length. In some embodiments, a k-mer is about or less than about 30 nt, 25 nt, 20 nt, 15 nt, 10 nt, or fewer in length. The k-mer may be in the range of 3 nt to 13 nt, 5 nt to 25 nt in length, 7 nt to 99 nt, or 3 nt to 99 nt in length. The length of k-mer analyzed at each step may vary. For example, a first comparison may compare k-mers in a sequencing read and a reference sequence that are 21 nt in length, whereas a second comparison may compare k-mers in a sequencing read and a reference sequence that are 7 nt in length. For any given sequence in a comparison step, k-mers analyzed may be overlapping (such as in a sliding window), and may be of same or different lengths. While k-mers are generally referred to herein as nucleic acid sequences, sequence comparison also encompasses comparison of polypeptide sequences, including comparison of k-mers consisting of amino acids. Reference sequences and reference databases used in performing a sequence comparison can be any described herein, such as with regard to any of the various aspects of the disclosure.

In general, comparing k-mers in a read to a reference sequence comprises counting k-mer matches between the two. The stringency for identifying a match may vary. For example, a match may be an exact match, in which the nucleotide sequence of the k-mer from the read is identical to the nucleotide sequence of the k-mer from the reference. Alternatively, a match may be an incomplete match, where 1, 2, 3, 4, 5, 10, or more mismatches are permitted. In addition to counting matches, a likelihood (also referred to as a "k-mer weight" or "KW") can be calculated. In some embodiments, the k-mer weight relates a count of a particular k-mer within a particular reference sequence, a count of the particular k-mer among a group of sequences comprising the reference sequence, and a count of the particular k-mer among all reference sequences in the database of reference sequences. In one embodiment, the k-mer weight is calculated according to the following formula, which calculates the k-mer weight as a measure of how likely it is that a particular k-mer ($K_i$) originates from a reference sequence (ref) as follows:

$$KWref_i(K_i) = \frac{C_{ref}(K_i)/C_{db}(K_i)}{C_{db}(K_i)/\text{Total } kmer \text{ count}} \quad \text{(Eqn. 1)}$$

C represents a function that returns the count of $K_i$. $C_{ref}(K_i)$ indicates the count of the $K_i$ in a particular reference. $C_{db}(K_i)$ indicates the count of $K_i$ in the database. This weight provides a relative, database specific measure of how likely it is that a k-mer originated from a particular reference. Prior to comparing a sequencing read to the database of reference sequences, the k-mer weight (or measurement of likelihood that a k-mer originates from a given reference sequence) can be calculated for each k-mer and reference sequence in the database. In some cases, when a reference databases comprises sequences from a plurality of taxa, each reference sequence can be associated with a measure of likelihood, or k-mer weight, that a k-mer within the reference sequence originates from a taxon within a plurality of taxa. As a non-limiting example, a reference database can comprise sequences from multiple species of canines, and the k-mer weight could be calculated by relating the count of a given k-mer in all canine sequences to its count in the entire database, which includes other taxa. In some examples, the k-mer weight measuring how likely it is that a k-mer originates from a specific taxon is calculated by defining $C_{ref}(K_i)$ in the above equation as a function that returns the total count of $K_i$ in a particular taxon. Results may be stored in a record database, examples of which are described herein, such as with regard to any of the various aspects of the disclosure.

A single detection process may comprise multiple sequence comparison steps. One or more of the steps may be performed for all sequences to be evaluated by that step in parallel. In some embodiments, a sequencing read is assigned to a first taxonomic group based on a first sequence comparison between the sequencing read and a first plurality of polynucleotide sequences from the different first taxonomic groups, wherein at least two sequencing reads are assigned to different taxonomic groups. A first taxonomic group may be a broad class, assignment to which may specify which reference database or reference sequences should be used in a second comparison to identify the sequence or corresponding taxon with greater specificity. For example, assignment to a first taxonomic class can comprise assigning a sequence to any of bacteria, archaea, chromalveolata, viruses, fungi, plants, fish, amphibians, reptiles, birds, mammals, and humans. The first plurality of polynucleotides may be in the form of a reference database, which can comprise sequences from any of a variety of taxa to which a sequence may be assigned. The first comparison may be performed for all sequencing reads to be analyzed in parallel, such that assignment to a first taxonomic group comprises assignment to the group yielding the closest match among all groups to which a sequencing read is compared.

After assigning sequencing reads to a first taxonomic group, a second sequence comparison step may be performed, wherein a sequencing read and a second plurality of polynucleotide sequences corresponding to members of the first taxonomic group to which the read was assigned are compared. The second comparison will typically comprise counting a number of k-mers within the sequencing read of at least 5 nucleotides in length that exactly match one or more k-mers within a reference sequence in the second plurality of polynucleotide sequences. Examples of k-mer analyses are provided herein, such as with respect to any of the various aspects of the disclosure. The second plurality of sequences may be in the form of a second reference database. The second plurality of polynucleotide sequences may comprise or consist of the subset of sequences associated with the first taxonomic group to which the sequencing read was assigned, or only a subset of these. The second plurality of polynucleotide sequences may comprise or consist of sequences associated with the first taxonomic group that were not among the first polynucleotide sequences. The parameters for the second sequence comparison may be the same or different from the parameters used in the first sequence comparison. For example, k-mer length, k-mer weight threshold to identify a match, or stringency may be the same or different, each of which may be varied independently.

As a result of the second sequence comparison, a sequencing read may be classified as belonging to a second taxonomic group that is more specific than the first taxonomic group if a measure of similarity between the sequencing read and reference sequence is above a first threshold level. Threshold for making an identification may vary depending on the parameters of the comparison. Examples of possible thresholds are provided herein, such as with regard to any of the various aspects of the disclosure. Determining a threshold may comprise calculating a sum of k-mer weights for a given sequencing read, as described herein. The threshold value may be selected based on a variety of factors, such as average read length, the reference sequences to which the reads are compared, whether a specific sequence or source organism is to be identified as present in the sample, and the like. The threshold value can be specific to the set of specified reference sequences. If the sum of k-mer weights for the reference sequence is above the threshold level, the sequencing read may be identified as corresponding to the reference sequence, and optionally the organism or taxonomic group associated with the reference sequence. In some cases, the read is assigned to the reference sequence with the maximum sum of k-mer weights, which may or may not be required to be above a threshold. In the case of a tie, where a sequence read has an equal k-mer weight of belonging to more than one reference sequence, the sequence read can be assigned to the taxonomic lowest common ancestor (LCA) taking into account the read's total k-mer weight along each branch of the phylogenetic tree. In general, correspondence with a reference sequence, organism, or taxonomic group indicates that it was present in the sample. In general, a second taxonomic group is considered more specific than a first taxonomic group when the second taxonomic group is of a more specific hierarchical order. For example, the first taxonomic group may be at the level of family, while the second taxonomic group is at the level of genus or species. Where the first taxonomic group is at the species level, the second taxonomic group may be at the level of a specific individual. For example, a sequence may be identified as human in the first sequence comparison, and classification based on the second comparison may identify the particular human from which the sequence was derived, a process which may further involve comparison of groups of sequences.

In some cases, classifying a sequencing read is not possible on the basis of the second comparison, such as in the case where the maximum sum of k-mer weights for a sequencing read is below a threshold. In this case, classifying the sequence read as belonging to the second taxonomic group can be based on similarity above a second threshold level determined by comparing with the computer system a sequence derived from translating the sequencing read and a third set of reference sequences corresponding to amino acid sequences of members of the first taxonomic group. Methods for translating sequencing reads are described herein. The process may comprise translation of one or more reading frames, such as all 6 reading frames. Comparison may be at the level of amino acids, where the translated sequencing read is compared to a set of reference amino acid sequences. Alternatively, the translated sequencing reads may be reverse-translated, and compared to reference sequences derived from reverse-translating reference amino acid sequences. Methods for translating and reverse-translating are described herein, and include reverse-translating using a non-degenerate code. Reference amino acid sequences may be in the form of a reference database, examples of which are described herein.

In some cases, classifying a sequencing read is still not possible on the basis of the comparison to the third set of reference sequences, such as in the case where the maximum sum of k-mer weights for a sequencing read is below a threshold. In this case, the method may further comprise performing with the computer system a relaxed sequence comparison between the sequencing read and the second plurality of polynucleotide sequences. In general, the relaxed sequence comparison is less stringent than the second sequence comparison. Methods for reducing stringency of a sequencing comparison are described herein, such with regard to any of the various aspects of the disclosure. Classifying may then be possible based on identifying matching sequences at the lower stringency. A similar reduced-stringency analysis may be applied with respect to reverse-translated amino acid reference sequences, which may be performed in place of or in addition to reduced-stringency comparison of reference polynucleotide sequences.

At any given step, two or more reference sequences from different taxa may be identified as possibly corresponding to the sequencing read based on the parameters for comparison. In such cases, the tie will usually be resolved in order to assign the sequencing read to just one reference sequence or taxon. In some cases, resolving a tie between two or more possible taxonomic groups based on the k-mer weight that the sequencing read corresponds to a polynucleotide from an ancestor of one of the possible taxonomic groups. Methods for resolving such ties are described herein, such as with regard to any of the various aspects of the disclosure.

Once a sequence has been classified as belonging to a second taxonomic group that is more specific than the first taxonomic group, the presence, absence, or abundance (which may be relative abundance) of a plurality of taxa in the sample may be determined. Methods for making such a determination on the basis of identifying sequencing reads are provided herein, such as with regard to any of the various aspects of the disclosure. In some embodiments, a method may further comprise quantifying an amount of polynucleotides corresponding to a reference sequence identified in an earlier step. Quantification can be based on a number of corresponding sequencing reads identified. This can include normalizing the count by the total number of reads, the total number of reads associated with sequences, the length of the reference sequence, or a combination thereof. Examples of such normalization include FPKM and RPKM, but may also include other methods that take into account the relative amount of reads in different samples, such as normalizing sequencing reads from samples by the median of ratios of observed counts per sequence. A difference in quantity between samples can indicate a difference between the two samples. The quantitation can be used to identify differences between subjects, such as comparing the taxa present in the microbiota of subjects with different diets, or to observe changes in the same subject over time, such as observing the taxa present in the microbiota of a subject before and after going on a particular diet. If a sequencing read classified as belonging to the second taxonomic group is not present among the group of reference sequences associated with that second taxonomic group, it may be added to the group of reference sequences for use in future comparisons.

In some embodiments, a method may comprise determining the presence, absence, or abundance of specific taxa within samples based on results of an earlier step. In this case, the plurality of reference polynucleotide sequences typically comprise groups of sequences corresponding to individual taxa in the plurality of taxa. In some cases, at least 50, 100, 250, 500, 1000, 5000, 10000, 50000, 100000, 250000, 500000, or 1000000 different taxa are identified as absent or present (and optionally abundance, which may be relative) based on sequences analyzed by a method described herein. In some cases, this analysis is performed in parallel. In some embodiments, the methods, compositions, and systems of the present disclosure enable parallel detection of the presence or absence of a taxon in a community of taxa, such as an environmental or clinical sample, when the taxon identified comprises less than 0.05% of the total population of taxa in the source sample. In some cases, detection is based on sequencing reads corresponding to a polynucleotide that is present at less than 0.01% of the total nucleic acid population. The particular polynucleotide may be at least 20%, 30%, 40%, 50%, 60%, 70%, 80%, 85%, 90%, 91%, 92%, 93%, 94%, 95%, 96% or 97% homologous to other nucleic acids in the population. In some cases, the particular polynucleotide is less than 75%, 50%, 40%, 30%, 20%, or 10% homologous to other nucleic acids in the population. Determining the presence, absence, or abundance of specific taxa can comprise identifying an individual subject as the source of a sample. For example, a reference database may comprise a plurality of reference sequences, each of which corresponds to an individual organism (e.g. a human subject), with sequences from a plurality of different subject represented among the reference sequences. Sequencing reads for an unknown sample may then be compared to sequences of the reference database, and based on identifying the sequencing reads in accordance with a described method, an individual represented in the reference database may be identified as the sample source of the sequencing reads. In such a case, the reference database may comprise sequences from at least $10^2$, $10^3$, $10^4$, $10^5$, $10^6$, $10^7$, $10^8$, $10^9$, or more individuals.

In some cases, a sequencing read does not have a match to a reference sequence at the level of a particular taxonomic group (e.g. at the species level), or at any taxonomic level. When no match is found, the corresponding sequence may be added to a reference database on the basis of known characteristics. In some cases, when a sequence is identified as belonging to a particular taxon in the plurality of taxa, and is not present among the group of sequences corresponding to that taxon, it is added to the group of sequences corresponding to the taxon for use in later sequence comparisons. For example, if a bacterial genome is identified as belonging to a particular taxon, such as a genus or family, but the genome comprises sequence that is not present in the sequences associated with that taxon, the bacterial genome can be added to the sequence database. Likewise, if the sample is derived from a particular source or condition, the sequencing read may be added to a reference database of sequences associated with that source or condition for use in identifying future samples that share the same source or condition. As a further example, a sequence that does not have a match at a lower level but does have a match at a higher level, as identified according to a method described herein, may be assigned to that higher level while also adding the sequencing read to the plurality of reference sequences that correspond to that taxonomic group. Reference databases so updated may be used in later sequence comparisons.

In some embodiments, identifying the presence, absence, or abundance of the plurality of taxa may be used to diagnose a condition based on a degree of similarity between the plurality of taxa detected in the sample and a biological signature for the condition. The condition can be any of the conditions described herein with regard to any of the aspects of the disclosure. Example conditions include, but are not limited to, contamination (e.g. environmental contamination, surface contamination, food contamination, air contamination, water contamination, cell culture contamination), stimulus response (e.g. drug responder or non-responder, allergic response, treatment response), infection (e.g. bacterial infection, fungal infection, viral infection), disease state (e.g. presence of disease, worsening of disease, disease recovery), a healthy state, or the identity of a sample source (e.g. a specific location or an individual subject). Examples of these are provided herein. The method may comprise identifying the condition in the sample or the source from which the sample is derived. The condition may be identified based on the presence or change in 10%, 20%, 30%, 40%, 50%, 60%, 70%, 80%, 90%, or 100% of the components of a biosignature. Alternatively, a condition may be identified based on the presence or change in less than 20%, 10%, 1%, 0.1%, 0.01%, 0.001%, 0.0001%, or 0.00001% of the components of a biosignature. In some embodiments, a sample is identified as affected by the condition if at least 80% of the sequences and/or taxa associated with the condition are identified as present (or present at a level associated with the condition). In some embodiments, the sample is identified as affected by the condition if at least 90%, 95%, 99%, or all sequences or taxa (or quantities of these) associated with the condition are present. Where the condition is one of being from a particular individual, such as an individual subject (e.g. a human in a database of sequences from a plurality of different humans), identifying the sample as being affected by the condition comprises identifying the sample as being from the individual to whom the sequences in the database correspond. In some embodiments, identifying a subject as the source of the sample is based on only a fraction of the subject's genomic sequence (e.g. less than 50%, 25%, 10%, 5%, or less).

The presence, absence, or abundance of particular sequences or taxa can be used for diagnostic purposes, such as inferring that a sample or subject has a particular condition (e.g. an illness) if sequence reads from a particular disease-causing organism are present at higher levels than a control (e.g. an uninfected individual). In another embodiment, the sequencing reads can originate from the host and indicate the presence of a disease-causing organism by measuring the presence, absence, or abundance of a host gene in a sample. The presence, absence, or abundance can be used to infer effectiveness of a treatment, wherein a decrease in the number of sequencing reads from a disease-causing agent after treatment, or a change in the presence, absence, or abundance of specific host-response genes, indicates that a treatment is effective, whereas no change or insufficient change indicates that the treatment is ineffective. The sample can be assayed before or one or more times after treatment is begun. In some examples, the treatment of the infected subject is altered based on the results of the monitoring.

In some cases, one or more samples having a known condition may be used to establish a biosignature for that condition using a method of the disclosure. The biosignature may be established by associating the presence, absence, or abundance of the plurality of taxa with the condition. The condition can be any condition described herein. For example, a plurality of samples from a particular environmental source may be used to identify sequences and/or taxa associated with that environmental source, thereby establishing a biosignature consisting of those sequences and/or taxa so associated. Various examples are provided elsewhere herein. In one particular example, a sample (e.g. from an individual or a cell culture) is identified as being infected by an infectious agent based on only a host gene expression biosignature, only on identification of one or more sequences associated with the infectious agent, or a combination of the two. In cases where both host transcripts and infectious agent sequences are used in identifying a condition, the condition so identified may be that of a passive carrier (e.g. where viral sequences are detected, but a host immune response is not).

The method may further comprise any of isolating polynucleotides from a sample, amplifying polynucleotides, and/or sequencing polynucleotides to generate sequencing reads for comparison, such as by any of the methods described herein.

In one aspect, the disclosure provides systems for performing any of the methods described herein. In some embodiments, the system is configured for identifying a plurality of polynucleotides in a sample from a sample source based on sequencing reads for the plurality of polynucleotides. For example, the system may comprise a computer processor programmed to, for each sequencing read: (a) perform a sequence comparison between the sequencing read and a plurality of reference polynucleotide sequences, wherein the comparison comprises calculating k-mer weights as measures of how likely it is that k-mers within the sequencing read are derived from a reference sequence within the plurality of reference polynucleotide sequences; (b) identify the sequencing read as corresponding to a particular reference sequence in a database of reference sequences if the sum of k-mer weights for the reference sequence is above a threshold level; and (c) assemble a record database comprising reference sequences identified in step (b), wherein the record database excludes reference sequences to which no sequencing read corresponds. As another example, the system may comprise one or more computer processors programmed to: (a) for each sequencing read, perform a sequence comparison between the sequencing read and a plurality of reference polynucleotide sequences, wherein the comparison comprises calculating k-mer weights as measures of how likely it is that k-mers within the sequencing read are derived from a reference sequence within the plurality of reference polynucleotide sequences; (b) for each sequencing read, calculate a probability that the sequencing read corresponds to a particular reference sequence in a database of reference sequences based on the k-mer weights, thereby generating a sequence probability; (c) calculate a score for the presence or absence of one or more taxa based on the sequence probabilities corresponding to sequences representative of said one or more taxa; and (d) identify the one or more taxa as present or absent in the sample based on the corresponding scores.

The system may further comprise a reaction module in communication with the computer processor, wherein the reaction module performs polynucleotide sequencing reactions to produce the sequencing reads. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules or techniques which, in turn, may be implemented in hardware, firmware, software, or any combination thereof. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. In some embodiments, the computer is configured to receive a customer request to perform a detection reaction on a sample. The computer may receive the customer request directly (e.g. by way of an input device such as a keyboard, mouse, or touch screen operated by the customer or a user entering a customer request) or indirectly (e.g. through a wired or wireless connection, including over the internet). Non-limiting examples of customers include the subject providing the sample, medical personnel, clinicians, laboratory personnel, insurance company personnel, or others in the health care industry.

In one aspect, the disclosure provides a computer-readable medium comprising codes that, upon execution by one or more processors, implements a method according to any of the methods disclosed herein. In some embodiments, execution of the computer readable medium implements a method of identifying a plurality of polynucleotides in a sample from a sample source based on sequencing reads for the plurality of polynucleotides. In one embodiment, the execution of the computer readable medium implements a method comprising: (a) for each of the sequencing reads, performing a sequence comparison between the sequencing read and a plurality of reference polynucleotide sequences, wherein the comparison comprises calculating k-mer weights as measures of how likely it is that k-mers within the sequencing read are derived from a reference sequence within the plurality of reference polynucleotide sequences; (b) for each of the sequencing reads, identifying the sequencing read as corresponding to a particular reference sequence in a database of reference sequences if the sum of k-mer weights for the reference sequence is above a threshold level; and (c) assembling a record database comprising reference sequences identified in step (b), wherein the record database excludes reference sequences to which no sequencing read corresponds.

In another embodiment, the execution of the computer readable medium implements a method of identifying one or more taxa in a sample from a sample source based on sequencing reads for a plurality of polynucleotides, the method comprising: (a) for each of the sequencing reads, performing a sequence comparison between the sequencing read and a plurality of reference polynucleotide sequences, wherein the comparison comprises calculating k-mer weights as a measure of how likely it is that k-mers within the sequencing read are derived from a reference sequence within the plurality of reference polynucleotide sequences; (b) for each of the sequencing reads, calculating a probability that the sequencing read corresponds to a particular reference sequence in a database of reference sequences based on the k-mer weights, thereby generating a sequence probability; (c) calculating a score for the presence or absence of one or more taxa based on the sequence probabilities corresponding to sequences representative of said one or more taxa; and (d) identifying the one or more taxa as present or absent in the sample based on the corresponding scores.

Computer readable medium may take many forms, including but not limited to, a tangible storage medium, a carrier wave medium, or physical transmission medium. Non-volatile storage media include, for example, optical or magnetic disks, such as any of the storage devices in any computer(s) or the like, such as may be used to implement the calculation steps, processing steps, etc. Volatile storage media include dynamic memory, such as main memory of a computer. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Sample System Architecture

Figure 1B:
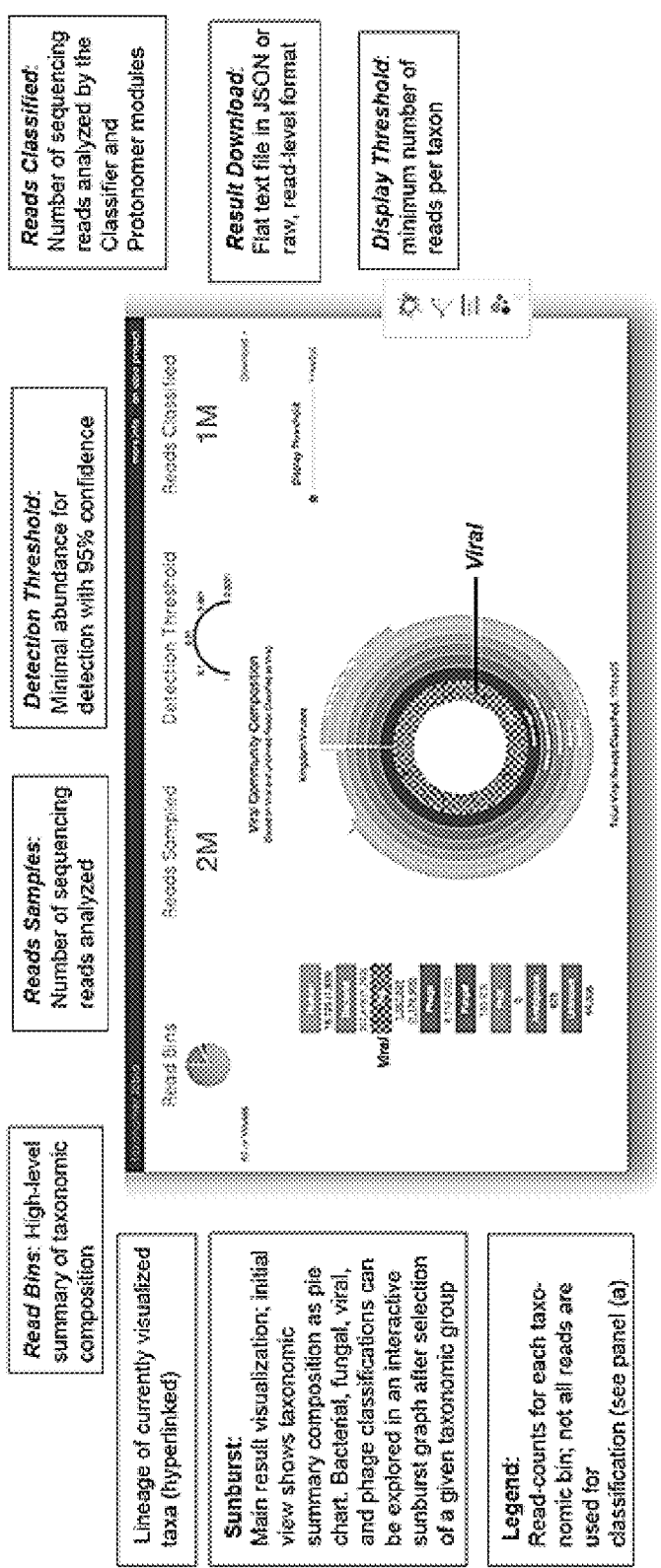

An example system in accordance with an embodiment of the disclosure was constructed. An overview of the structure and user interface of this system is illustrated in FIGS. 1A-B, and is referred to in these examples as Taxonomer. For the various analyses in these examples, raw FASTQ files were the input for Taxonomer, which comprised four main modules. The 'Binner' module categorized ("bins") sequencing reads into broad taxonomic groups (e.g. host and microbial) followed by comprehensive classification at the nucleotide ('Classifier' module) or amino acid-level ('Protonomer' and 'Afterburner' modules). In this example system, the 'Binner' module used exact k-mer counting for read assignment with a predefined minimum threshold. The 'Classifier' module applied exact k-mer matching and probabilistic taxonomic assignment for host transcript expression profiling and classification of bacteria and fungi at the nucleotide level. The 'Protonomer' module applied 6-frame translation for virus detection at the amino acid-level. When using discovery mode, sequencing reads that failed amino acid-level classification were subjected to the 'Afterburner' module, which used a reduced amino acid alphabet for increased sensitivity. Default classification databases included ENSEMBL (see Flicek, P. et al. *Ensembl 2014. Nucleic acids research* 42, D749-755 (2014)) (human transcripts), Greengenes (see DeSantis, T. Z. et al. *Greengenes, a chimera-checked 16S rRNA gene database and workbench compatible with ARB. Applied and environmental microbiology* 72, 5069-5072 (2006)) (bacteria), UNITE (see Koljalg, U et al. *Towards a unified paradigm for sequence-based identification of fungi. Molecular ecology* 22, 5271-5277 (2013)) (fungi), and UniRef90 (see Suzek, B. E., Huang, H, McGarvey, P., Mazumder, R. & Wu, C. H. *UniRef comprehensive and non-redundant UniProt reference clusters. Bioinformatics* 23, 1282-1288 (2007)) (viruses, phages). Microbial profiles can be provided in BIOM format (see McDonald, D. et al. *The Biological Observation Matrix (BIOM) format or: how I learned to stop worrying and love the ome-ome. GigaScience* 1, 7 (2012)). FASTQ formatted read subsets can be used for custom downstream analyses. To further remove barriers for clinical and academic adoption of metagenomics, a web interface was developed for Taxonomer that allows users to stream FASTQ files (local or through http access) to the analysis server and interactively visualize results in real-time (illustrated in FIG. 1B). Using the streaming web application, more than $1 \times 10^5$ paired-end reads can be analyzed and visualized in about 5 seconds with fast Internet connection. Features of Taxonomer are described in grey boxes. Additional features of Taxonomer are further described below.

The Binner database was created by counting unique 21 bp k-mers in different taxonomic or gene datasets. This was done using Kanalyze, version 0.9.7 (see Audano, P. & Vannberg, F. *KAnalyze: a fast versatile pipelined k-mer toolkit. Bioinformatics* 30, 2070-2072 (2014)), but could have alternatively used Jellyfish, version 2.3, (see Marcais, G. & Kingsford, C. *A fast, lock-free approach for efficient parallel counting of occurrences of k-mers. Bioinformatics* 27, 764-770 (2011)). Each taxonomic or gene dataset represented a "bin" in which query sequences could be placed based on their k-mer content. Each database was assigned a unique bitwise flag that allowed k-mers to belong to one or more bins to be recognized and counted. The database bins and flags are shown in FIG. 19. The k-mer counts were merged into a single binary file with two columns, the k-mers and the database flag. Additional columns for other information can be accommodated. The file was sorted lexicographically to optimize for rapid k-mer queries. Reads were then assigned to the taxonomic group(s) with which the most k-mers were shared. Some reference sequence databases are subsets or overlap with others (e.g. 'Human transcripts' and 'Human genome') and some sequences may be assigned varying taxID's (e.g. phage sequences may be annotated as viruses or as bacteria, if integrated as prophages). As a result, query sequences may share an equal number of k-mers with more than one reference database. The 'Binner' module assigns these query sequences as outlined below in Table 1. For web display, sub-bins were displayed as part of a larger bin, the organization of which is summarized for visualization in Table 2.

TABLE 1

Bin assignment for reads with equal numbers of k-mer matches to multiple Binner databases and k-mer matches below threshold.

| Equal k-mer count of . . . | And . . . | Assignment |
|---|---|---|
| 'Human transcripts' | 'Human genome' and/or 'Mitochondrial genomes' | 'Human transcripts' |
| 'Bacterial 16S' | 'Bacterial LSU' and/or 'Bacterial genomes' and/or 'Plastids LSU/SSU' | 'Bacterial 16S' |
| 'Fungal ITS' | 'Fungal genomes' and/or 'Fungal LSU/SSU' | 'Fungal ITS' |
| 'Phage' | 'Viruses (NCBI)' and/or 'Bacterial genomes' | 'Phage' |
| All other ties | | 'Ambiguous' |
| K-mer count < threshold | | 'Unknown' |

TABLE 2

Contents of visualized pie charts in the web portal.

| Bin | Sub-bins |
|---|---|
| Human | 'Human genome', 'Human transcripts', 'Mitochondrial genomes' |
| Bacterial | 'Bacterial genomes', 'Bacterial SSU', 'Bacterial LSU', 'Plastids LSU/SSU' |
| Fungal | 'Fungal genomes', 'Fungal LSU/SSU', 'Fungal ITS' |
| Viral | 'Viruses (NCBI)', 'Phage' |
| Other | 'Other Eukaryotes LSU/SSU' |
| Ambiguous | Any database combination not specified above |

Figure 6B:
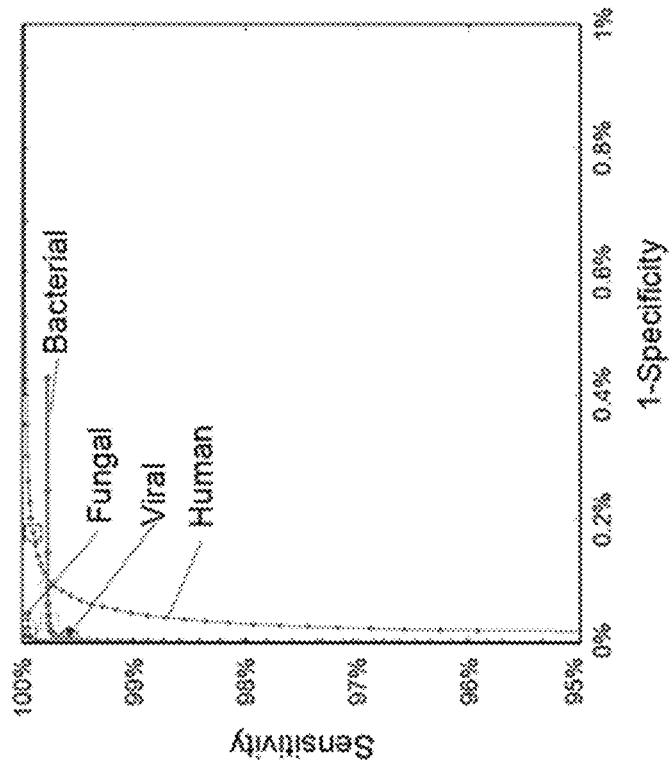
FIGS. 6A-D show performance characteristics of an embodiment of Taxonomer's 'Binner' module.
Figure 6A:
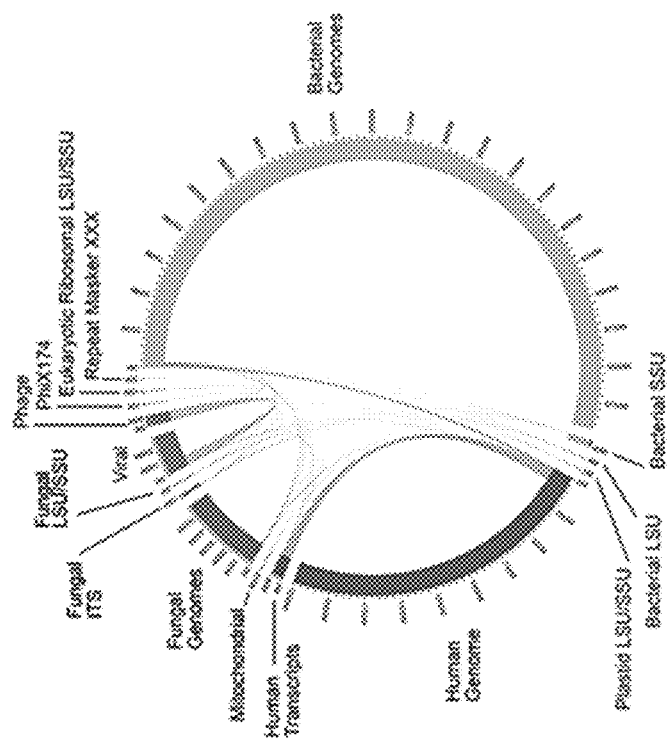

High binning accuracy was achieved through minimal intersections (0.47%) of k-mer content from comprehensive human and microbial reference databases (FIG. 6A-6B). Optimal k-mer cutoffs were determined by receiver operator characteristics analysis using Youden's indexes and F1 scores (see Akobeng, A. K. *Understanding diagnostic tests 3: Receiver operating characteristic curves. Acta Paediatr* 96, 644-647 (2007)) and ranged from 3 to 13 (Table 3, default, n=11). A default k-mer of 11 was chosen for the Binner module based on these results.

TABLE 3

Optimal k-mer cutoffs for bin assignments based on the Youden's Index and F1 Score.

| | Youden's Index | F1 Score |
|---|---|---|
| Human | 13 | 13 |
| Bacteria | 5 | 8 |
| Fungal | 3 | 4 |
| Virus | 3 | 4 |
| Parasite | 22 | 21 |

In order to eliminate binning based on reads containing adapter sequence, an adapter database can be provided; Binner can ignore k-mers present in the adapter database. In this example, Binner ignored k-mers present in Illumina TruSeq adapters. Furthermore, a database of spiked-in control sequences can be provided (e.g. database of External RNA Controls Consortium (ERCC) control sequences) to allow quantification of spike-in controls.

Classifier was used to identify the source of sequences after the sequences were subset by Binner. Classifier identified the source of a sequence based on exact k-mer matching. The k-mer weight for reference sequence was calculated in accordance with Equation 1 and reads were assigned to a reference sequence based on the sum of k-mer weights. In the case of a tie, the query sequence was assigned to the taxonomic lowest common ancestor (LCA) taking into account the read's total k-mer weight along each branch of the phylogenetic tree.

Sequence reads that were not classified above a threshold by Classifier and sequences that binner had placed in the viral category were additionally processed by Protonomer. Reads were translated in all six reading frames and then reverse-translated using a non-degenerate translation scheme. The UniRef90 protein database was reverse-translated using the same non-degenerate translation scheme. The reverse-translated sequences for each read were compared to the reverse-translated UniRef90 database with 30-bp k-mers (corresponding to 10 amino acids) in accordance with Equation 1 as described above.

Figure 8A:
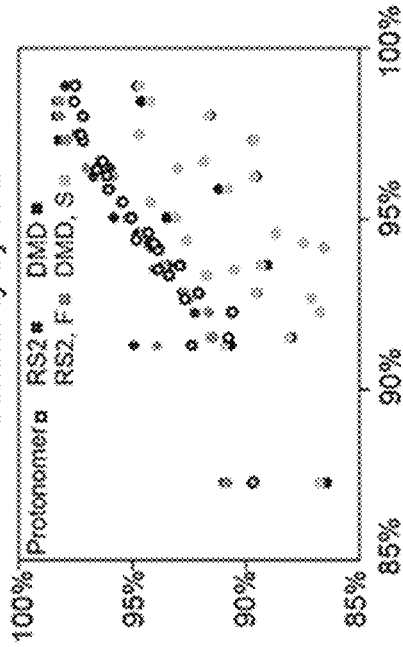
FIGS. 8A-C illustrate results for performance and sensitivity of an embodiment of Taxonomer's Protonomer module, RAPSearch2, and Diamond in placing viral reads in the correct taxonomic bin.

To increase recovery of distantly homologous proteins, Taxonomer employed the Afterburner module, a degenerate k-mer matching engine that employs a collapsed amino-acid alphabet. Afterburner used k-means clustering on the BLOSUM62 matrix to generate a compressed amino acid alphabet (see FIG. 8). This compressed alphabet results in higher sensitivity in classification with sequences that are more diverged at the expense of a higher false positive rate when compared with Protonomer.

Example 2: Sample Web-Service and Implementation

In this example, a web-service and implementation for Taxonomer as described in Example 1 are described. Complex metagenomic data can be processed quickly and effectively interpreted through web-based visualizations (FIG. 1B illustrates such an interface).

As reads were being streamed to the analysis server, a pie chart was presented summarizing the results of the binning procedure. When one of the bacterial, fungal, viral, or phage bins of the pie chart was selected, the results of the Classifier/Protonomer modules were displayed in a sunburst visualization.

Additional information was provided at the top of the web page about how many reads were sampled, the number of reads classified, and the detection threshold. The detection threshold informs a user about how abundant a particular organism must be in order to be detected with the number of reads sampled, thereby providing an indicator of the sensitivity of detection in the sample. In addition, a slider allowed the user to select an absolute cutoff for the minimum number of reads required in order to be displayed in the sunburst.

Example 3: Database Construction for Taxonomer

In this example, construction of databases for Taxonomer as described in Example 1 are described. The Classifier and Protonomer databases are modular, consisting only of multi-fasta files with a 'parent tag' on their definition lines. These tags describe each reference sequence's immediate phylogenetic parent-taxon.

Bacterial classification was based on a marker gene approach. The marker genes were 16S rRNA gene and genes from the Greengenes database (reference set with operational taxonomic units, OTU, clustered at 99%, version 13_8, FIG. 19). This reference set contained 203,452 OTU clusters from 1,262,986 reference sequences. The taxonomic lineage for each OTU was used to create a hierarchical taxonomy map to represent OTU relationships. To support the OTU 'species' concept, the taxonomy was completed for ranks in the taxonomic lineage that had no value. Unique dummy species names from the highest taxonomic rank available were used to fill empty values. Versions of the Greengenes database were formatted for use within BLAST, the RDP Classifier, and Kraken.

Fungal classification was also based on a marker gene approach. The marker genes were internal transcribed spacer, ITS, rRNA sequences, and the UNITE database (see Koljalg, U. et al. Towards a unified paradigm for sequence-based identification of fungi. Molecular ecology 22, 5271-5277 (2013)) (version sh_taxonomy_qiime_ver6_dynamic_s_09.02.2014, FIG. 19). This reference set contained 45,674 taxa (species hypothesis, SH) generated from 376,803 reference sequences with a default-clustering threshold of 98.5% and expert taxonomic curation. Dummy names were created for ranks that had no value. Versions of the UNITE database were formatted for use with BLAST, the RDP Classifier, and Kraken.

The viral protein database was created by using UniRef90 (see Suzek, B. E., Huang, H., McGarvey, P., Mazumder, R. & Wu, C. H. UniRef: comprehensive and non-redundant UniProt reference clusters. Bioinformatics 23, 1282-1288 (2007)) downloaded on Jun. 16, 2014. The database was reduced to 289,486 viral sequences based on NCBI taxonomy. Phage sequences were separated, leaving a total of 200,880 references for other viruses. NCBI taxonomy was used to determine the sequence relationship.

For testing purposes, an additional bacterial classification database was constructed from RefSeq (identical to Kraken's full database; n=210,627 total references; n=5,242 bacterial references, using NCBI taxonomy), and the complete ribosomal database project databases download on Sep. 24, 2014 (n=2,929,433 references, using RDP taxonomy).

Databases were constructed to maximize query speed. K-mers were stored in lexicographical order, and k-mer minimizers are used to point to blocks of k-mers in the database. Once a block of k-mers is isolated, a binary search was used to complete the query. In addition to storing the LCA of a k-mer, we also stored the k-mer count and every reference (up to an adjustable cutoff) with associated k-mer weight.

The Binner database consisted of two binary files: One with extension ".bmi", the other with extension ".btbi". The file with extension ".bmi" contained information about k-mer minimizers and pointers to blocks of k-mers in the ".btbi" file. The ".bmi" file contained rows with the following format:

TABLE 3a

| Variable types in .bmi file | |
| --- | --- |
| Variable type | Variable meaning |
| uint64_t | k-mer minimizer |
| uint64_t | Number of k-mers in block indexed by this minimizer |
| uint64_t | Byte offset to beginning of k-mer block in ".btbi" file |

The ".btbi" file had a header that is 176 bits. The header consisted of the following values and C variable types:

TABLE 4

| Variable types in .btbi file | |
| --- | --- |
| Variable type | Variable meaning |
| uint8_t | k-mer length (<32) |
| uint8_t | k-mer minimizer length (<16) |
| uint64_t | Unique k-mer count |
| uint64_t | Total k-mer count |
| int | k-mer cutoff |
| int | taxID cutoff |

Every k-mer block indexed by the ".bmi" file started with the following row in the ".btbi" file:

TABLE 5

| Structure of starting row of k-mer block indexed in .btbi file | |
| --- | --- |
| Variable type | Variable meaning |
| uint64_t* | Byte offsets to individual k-mers in this block |

All other rows after first row in k-mer block had the following format:

TABLE 6

| Structure of all other rows of k-mer block indexed in .btbi file | |
| --- | --- |
| Variable type | Variable meaning |
| uint64_t | k-mer |
| uint64_t | k-mer database designation |

The Classifier database consisted of 3 binary files with the following extensions: ".mi", ".tbi", and ".rsi". The file with extension ".mi" contained information about k-mer minimizers and pointers to blocks of k-mers in the ".tbi" file. The ".mi" file contains rows with the following format:

TABLE 7

Structure of rows in .mi file

| Variable type | Variable meaning |
| --- | --- |
| uint64_t | k-mer minimizer |
| uint64_t | Number of k-mers in block indexed by this minimizer |
| uint64_t | Byte offset to beginning of k-mer block in ".tbi" file |

The ".tbi" file has a header that is 176 bits. The header consisted of the following values and C variable types:

TABLE 8

Structure of the header row in .tbi file

| Variable type | Variable meaning |
| --- | --- |
| uint8_t | k-mer length (<32) |
| uint8_t | k-mer minimizer length (<16) |
| uint64_t | Unique k-mer count |
| uint64_t | Total k-mer count |
| int | k-mer cutoff |
| int | taxID cutoff |

Every k-mer block indexed by the ".mi" file started with the following row in the ".tbi" file:

TABLE 9

Structure of non-header rows in .tbi file

| Variable type | Variable meaning |
| --- | --- |
| uint64_t* | Byte offsets to individual k-mers in this block |

All other rows in a k-mer block after first row of the k-mer block had the following format in the ".tbi" file:

| Variable type | Variable meaning |
| --- | --- |
| uint64_t | k-mer |
| uint64_t | k-mer count |
| uint64_t | Byte offset to taxids and k-mer weights in ".rsi" file |

The ".rsi" file had the following format for each row:

TABLE 10

Structure of rows in .rsi file

| Variable type | Variable meaning |
| --- | --- |
| uint64_t | taxID count |
| uint64_t* | taxIDs |
| uint64_t* | k-mer weights for each taxID |

The Taxonomer database included individual k-mer weights for every taxID. This allowed Taxonomer to accumulate these weights across reads to increase both sequence query assignment sensitivity and specificity.

Example 4: Comparison of Taxonomer to SURPI

In this example, the performance of Taxonomer described in Example 1 was compared to SURPI (see e.g. Naccache, S. N. et al. A cloud-compatible bioinformatics pipeline for ultrarapid pathogen identification from next-generation sequencing of clinical samples. Genome research 24, 1180-1192 (2014)). Taxonomer used a non-greedy binning algorithm, as opposed to SURPI, which employs a greedy digital subtraction algorithm (see FIG. 7). The data analyzed in this example came from one of the 33 pediatric respiratory tract samples shown in FIG. 6D (RNA) and an additional nasopharyngeal sample (DNA). Of the reads classified as human by SURPI, 1% were classified by Taxonomer as fungal, to lower resolution (11%) or cannot confidently be differentiated between closely related bins (23%) when using a simultaneous binning strategy.

While high-level taxonomic assignments made by the two algorithms agreed for 73.8% of reads, Taxonomer assigned 16% of reads to an ambiguous origin (matching equally to multiple databases), whereas 96% of these were classified as human by SURPI. This was mostly due to highly conserved ribosomal and mitochondrial sequences, but similar effects were also apparent for fungal sequences, 18% of which classified as human by SURPI.

Taxonomer's alignment-free binning approach was able to capture more phage/viral sequences (7,426) than the alignment-based method (5,798), and resulted in fewer unclassified sequencing reads (3.2% vs. 4.5%). Consistent with the lower abundance of rRNA and mtRNA sequences in DNA sequencing data, Taxonomer had many fewer ambiguous assignments in the DNA dataset than the RNA dataset (0.04%, of which 40% were classified as human and 59% as viral by SURPI; overall agreement 98.7%). In addition to decreased numbers of false negatives, Binner also provides users of the Taxonomer web-service with a high-level overview of the contents of even the largest and most complicated dataset within the first second or so of computation.

Example 5: Assessment of Analysis Time and Completeness of Classification

In this example, the performance of Taxonomer described in Example 1 was compared to Kraken and SURPI. FIG. 18 presents time and classification percentages for Taxonomer, Kraken, and SURPI. For this analysis, an RNA-Seq data from three virus-positive respiratory tract samples with a range of host vs. microbial composition profiles was used (see e.g. Graf, E. H. Evaluation of Metagenomics for the Detection of Respiratory Viruses Directly from Clinical Samples. (2015)).

Kraken was the fastest tool; it required about 1.5 min/sample on average. However, possibly due to its reliance on nucleic acid-level classification only and use a single reference database, Kraken classified fewer reads than Taxonomer or SURPI. SURPI enabled amino acid-level searches for virus detection and discovery, but this greatly extended analysis times to between 1.5 and >12 hours per sample. Like SURPI, Taxonomer provided both nucleic acid and protein-based microbial classification, but Taxonomer also created a host-expression profile. Taxonomer achieved times similar to Kraken, requiring on average ~5 minutes to classify $5-8 \times 10^6$ paired-end reads using 16 CPUs. Moreover, Taxonomer classified the largest number of reads in 2 of the 3 samples and tied with SURPI for the third sample.

Figure 6D:
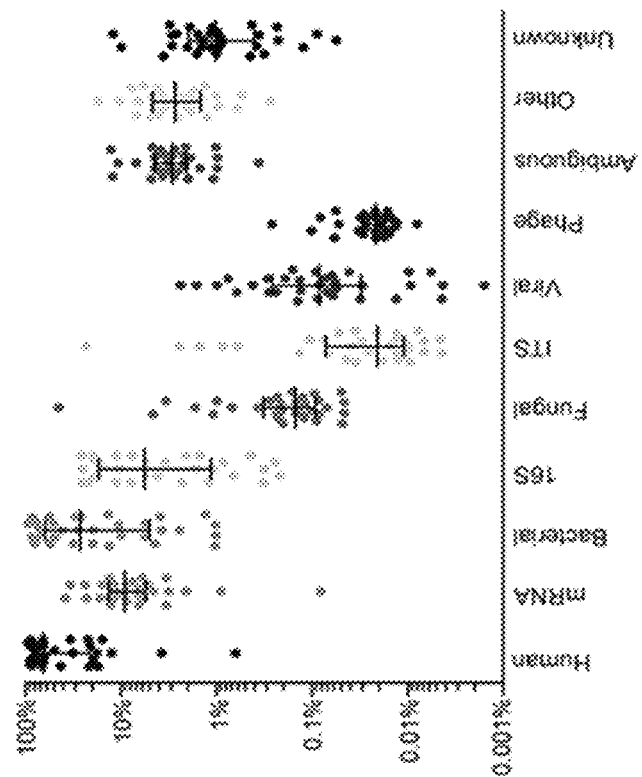
Figure 6C:
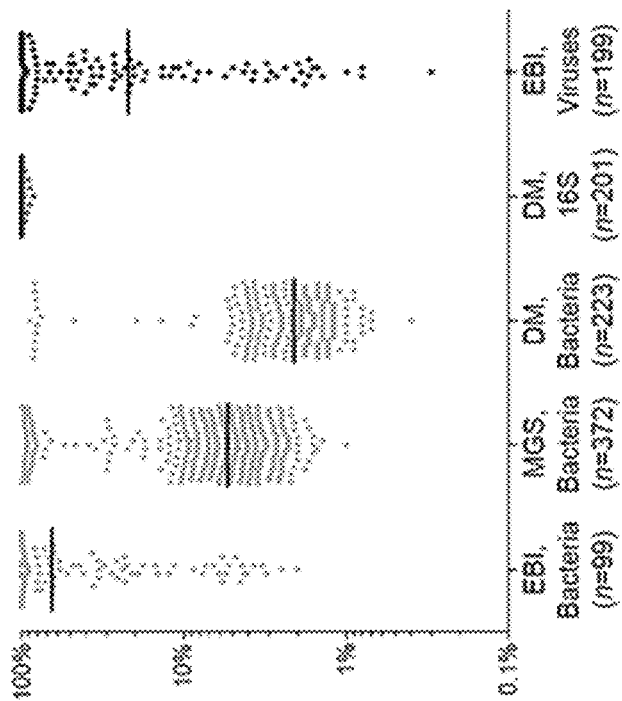
Figure 7:
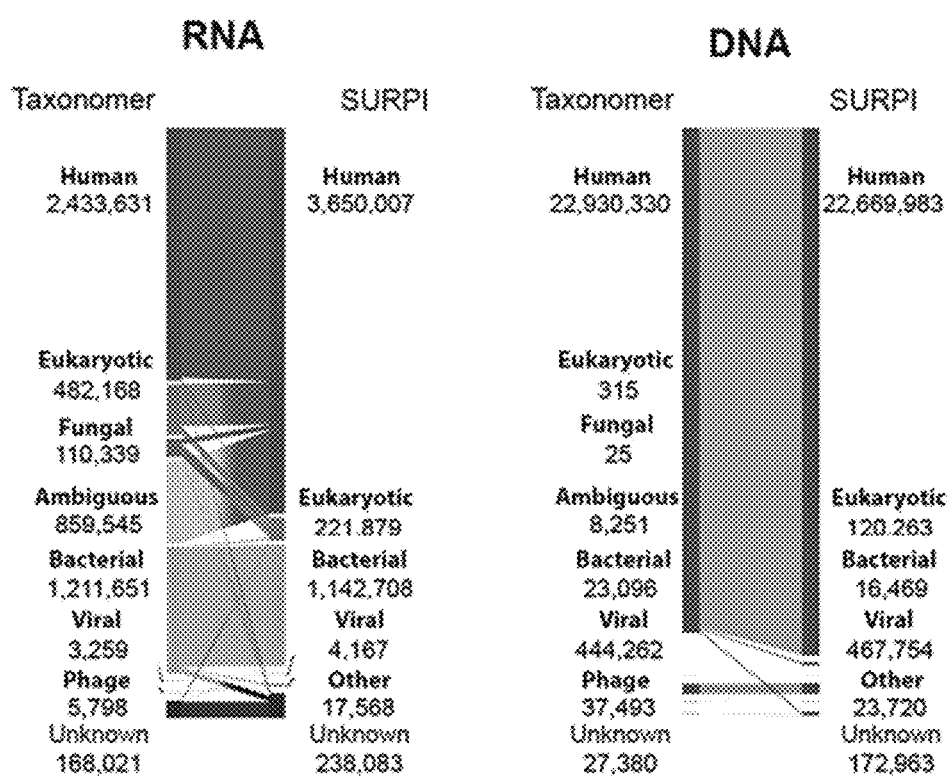
FIG. 7 illustrates results demonstrating an increase in accuracy achieved by calculating the number of k-mers shared between a sequencing read and each of the binning databases prior to read assignment (parallel approach).

Taxonomer provided fast, and effective means for read and contig classification, was substantially more accurate than the fastest available tools (Kraken and SURPI), and achieved accuracies on 16S amplicon data that closely approach the current standard, RDP. This was facilitated by Taxonomer's comprehensive databases, its k-mer weight approach, and its ability to carry out nucleotide and protein-based searches and classification within a single integrated algorithmic framework. On the datasets tested, Taxonomer was hours faster than SURPI and days faster than RDP. 16S sequences (but not synthetic reads derived from other genomic targets) from the same unrepresented bacteria are almost always correctly binned by Taxonomer (but not erroneously classified; see FIG. 6), highlighting the advantages of Taxonomer's marker gene-based approach, both for discovery of novel organisms and for avoiding misclassification pitfalls. FIG. 6B also shows receiver operator characteristics (ROC) curves for classification of human and microbial sequences by the 'Binner' module. A total of $1 \times 10^6$ synthetic 100 bp reads (80% human, 10% bacterial, 5% fungal, 1% viral, and 4% from parasites; 1% error rate) were analyzed with the 'Binner' module and interpreted for correct bin assignment to calculate sensitivity and specificity using minimum k-mer count thresholds for read binning ranging from 1 to 40. Boxed and circled thresholds represent optimal cutoffs as determined by F1 score and Youden's index, respectively (see Table 3). FIG. 6C shows that the sensitivity for binning of bacterial and viral reads can be low for phylogenetically distant species. Synthetic bacterial and viral reads were generated from single-cell sequencing-based draft bacterial genomes, bacterial genome scaffolds derived from metagenomic sequencing data, and recently published genome sequences. Sensitivity for correct binning (vs. assignment as 'Unknown') can be low for bacteria (median 2.1%, 5.4%, and 64.9%, respectively) and viruses (median 22.1%, 0% for n=56 of 199 viral genomes) not represented in the Binner database. In contrast, 16S sequences from the same unrepresented bacteria are almost always correctly binned (median 100%). This highlights the conservation of the 16S rRNA marker gene and the greater completeness of reference databases. As a result, organisms are still identified as present within the sample and can be placed within phylogenetic context. FIG. 6D shows the relative read abundance of different taxonomic bins as determined by the 'Binner' module for 33 pediatric respiratory tract samples positive for at least one respiratory virus, including median and interquartile range (IQR) for each bin ($6.3 \times 10^6 \pm 2 \times 10^6$ reads/sample). Relative abundances vary greatly for all bins but reached almost 4 orders of magnitude for the viral and fungal bins. A median of only 1% (IQR 0.4-2%) of reads could not be assigned a bin (unknown). A median of 9% of reads were derived from human mRNA, supporting the idea that host transcript expression profiling can be performed using total RNA-seq from nasopharyngeal samples.

Example 6: Bacterial and Fungal Classification

In this example, the embodiment of Taxonomer described in Example 1 was used to classify reads derived from bacterial and fungal samples. A comprehensive classification database can mitigate errors resulting from imperfect matches from query sequences to databases. The choice of default reference database can affect the specificity and sensitivity of a classifier. One solution is to use RefSeq, but the version of RefSeq (at the time of access) only contained some 5,000 sequenced bacterial taxa, whereas available 16S rRNA sequences suggest existence of at least 100,000 to 200,000 OTUs given existing sequence databases. Reads derived from taxa that are absent from the classification database can result in false negative and false positive classifications, especially at the genus and species level (FIG. 11).

Figure 11:
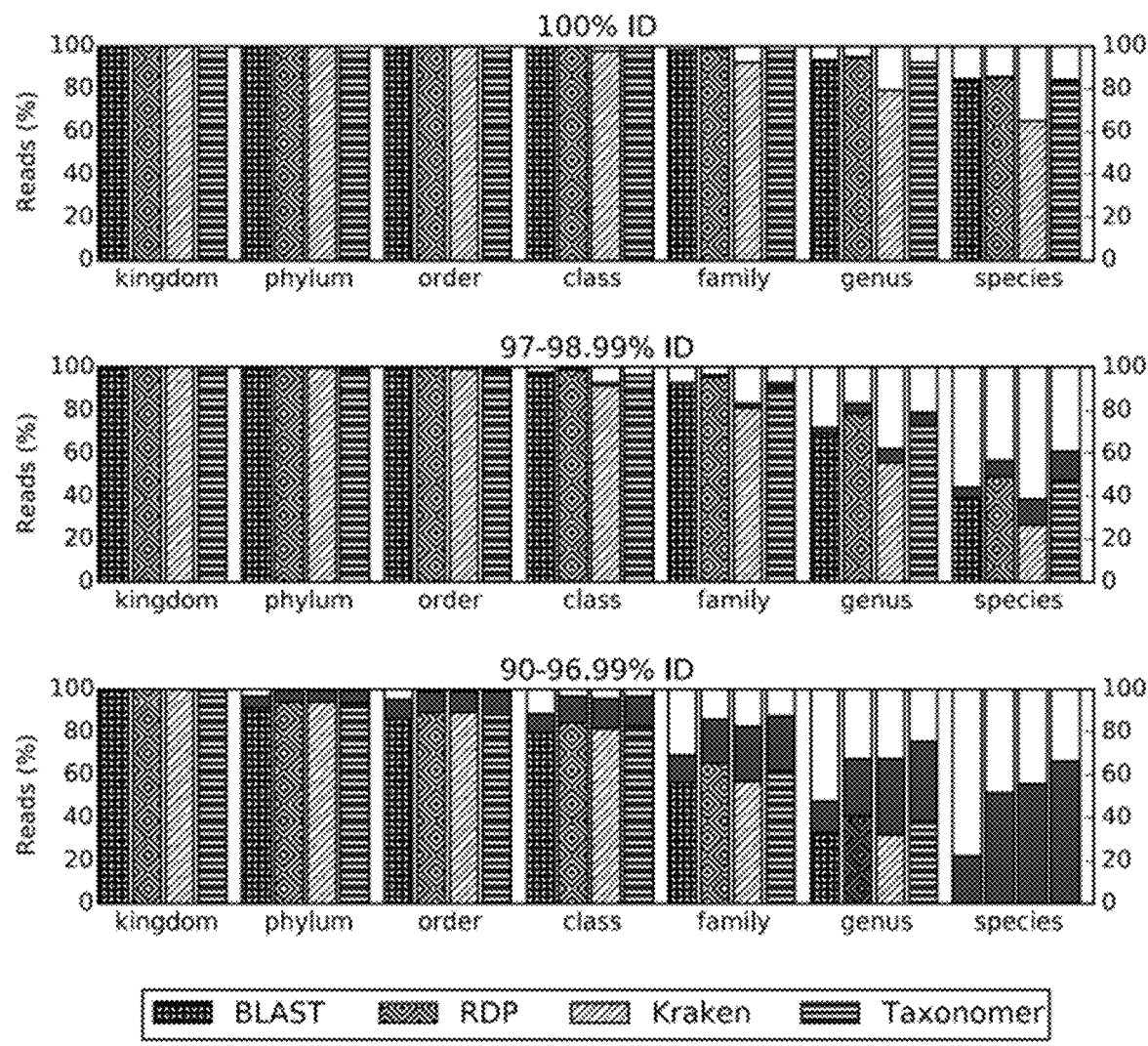
FIG. 11 illustrates results showing that query sequences not represented in the reference database cause false-positive and false-negative classifications, and that an embodiment of Taxonomer is less affected by this than other tools.

FIG. 11 shows that query sequences not represented in the reference database cause false-positive and false-negative classifications, and that Taxonomer is less affected than other tools. FIG. 11A shows the read-level classification accuracy for synthetic reads simulated (20× coverage) from SILVA references (n=10,000) with identical representation in the reference database as classified by BLAST, the RDP Classifier, Kraken, and Taxonomer. While only 84.2% (BLAST), 85.2% (RDP), 64.9% (Kraken), and 83.7% (Taxonomer) of reads are classified to the species level (an effect of highly conserved regions of the 16S gene not allowing species-level assignment), false-positive rates are minimal for all classification algorithms, 0.4% (BLAST), 0.7% (RDP), 0.02% (Kraken), and 0.1% (Taxonomer). FIG. 11B shows the same analysis with SILVA references (n=10,000), for whom highly similar, but non-identical references (97% to 98.99% pairwise sequence identity based on full-length MegaBLAST) are present in the reference database. Proportions of reads with species-level classification drop to 39.1% (BLAST), 49.0% (RDP), 26.9% (Kraken), and 47.4% (Taxonomer), and 5.3% (BLAST), 5.1% (RDP), 10.2% (Kraken), and 13.7% (Taxonomer) of reads are classified to taxa that are different from the source of the synthetic reads. FIG. 11C shows that this effect is even more pronounced for synthetic reads simulated from SILVA references (n=10,000) that only share 90% to 96.99% pairwise sequence identity with the closest match in the reference database (based on full-length MegaBLAST). In this case, species-level classification was not possible by the commonly used definition, and even genus-level classification drops to 33.0% (BLAST), 40.8% (RDP), 32.1% (Kraken), and 38.8% (Taxonomer). At the species-level, 22.1% (BLAST), 51.5% (RDP), 55.7% (Kraken), and 66.4% (Taxonomer) of reads are assigned to taxa other than those they were simulated from. All studies were performed with 250 bp paired-end 16S rDNA reads simulated at 20× coverage from randomly selected SILVA references with no error.

TABLE 11

Broad taxonomic classification of read 1 versus read 2 by SURPI differs for 2-9% of mate pairs. Broad taxonomic classification by SURPI (as per FIG. 2D) was determined for read 1 and read 2 of paired synthetic reads (SILVA 119) and RNA-Seq data (samples from FIG. 1B, limited to pairs passing quality filters, see methods). Broad taxonomic assignments were compared for concordance. Discordance ranged between 2-3% for synthetic 16S read pairs and from 3-9% for RNA-Seq data. Discordance was greatest for samples with higher abundance of bacterial reads (samples 2 and 3, FIG. 1B), presumably due to database incompleteness, inconsistent annotations, and because SURPI's assignment is based on the single reference sequence with the highest score.

| Sample | Read Length | Read pairs with discordant assignment, R1 vs. R2 (n) | Total pairs (n) | % |
|---|---|---|---|---|
| Synthetic 16S | 2 × 100 bp | 6,984 | 300,128 | 2.3 |
| Synthetic 16S | 2 × 250 bp | 2,888 | 119,009 | 2.4 |
| Sample 1 (FIG. 18) | 2 × 100 bp | 172,759 | 5,916,921 | 2.9 |

TABLE 11-continued

Broad taxonomic classification of read 1 versus read 2 by SURPI differs for 2-9% of mate pairs. Broad taxonomic classification by SURPI (as per FIG. 2D) was determined for read 1 and read 2 of paired synthetic reads (SILVA 119) and RNA-Seq data (samples from FIG. 1B, limited to pairs passing quality filters, see methods). Broad taxonomic assignments were compared for concordance. Discordance ranged between 2-3% for synthetic 16S read pairs and from 3-9% for RNA-Seq data. Discordance was greatest for samples with higher abundance of bacterial reads (samples 2 and 3, FIG. 1B), presumably due to database incompleteness, inconsistent annotations, and because SURPI's assignment is based on the single reference sequence with the highest score.

| Sample | Read Length | Read pairs with discordant assignment, R1 vs. R2 (n) | Total pairs (n) | % |
|---|---|---|---|---|
| Sample 2 (FIG. 18) | 2 × 100 bp | 586,486 | 6,261,301 | 9.4 |
| Sample 3 (FIG. 18) | 2 × 100 bp | 326,263 | 5,536,276 | 5.9 |

Figure 2A:
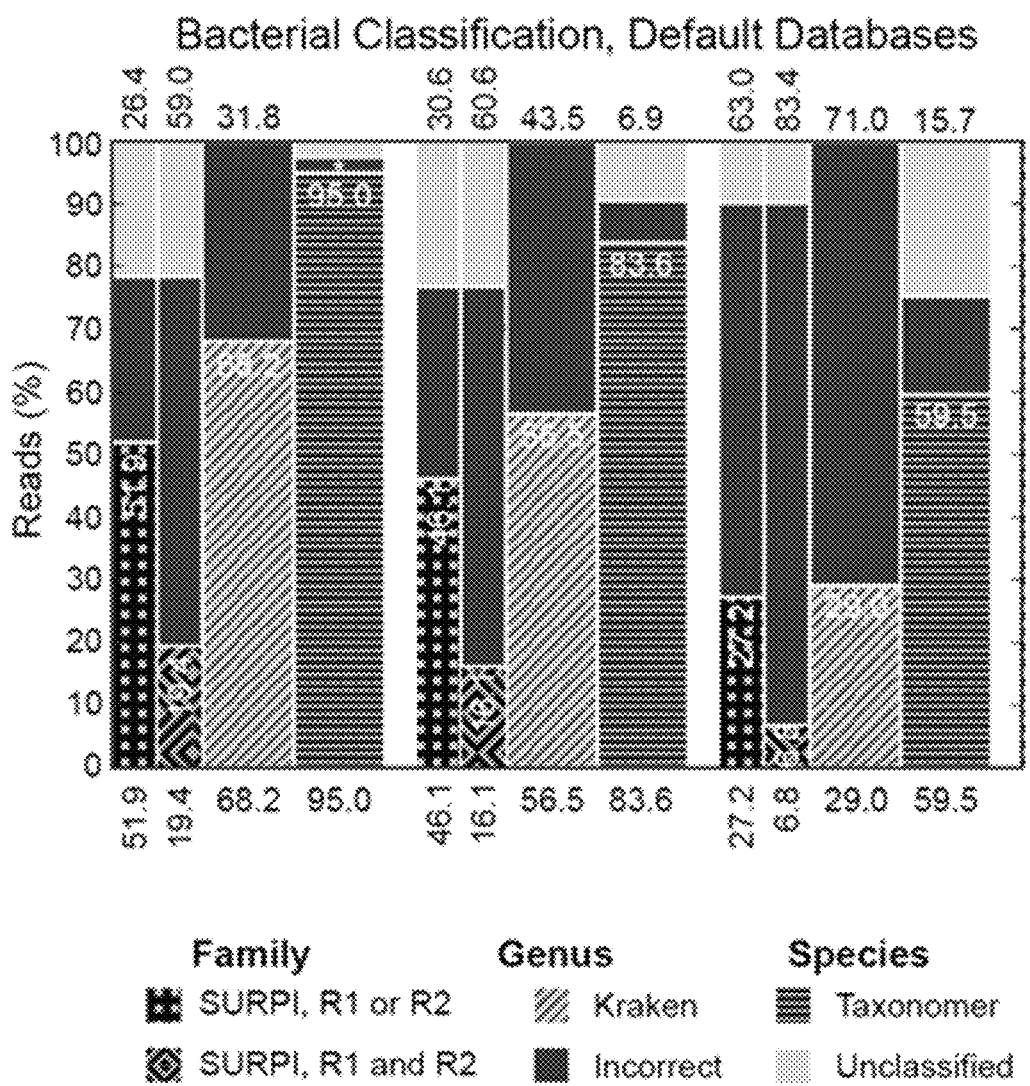
Figure 10:
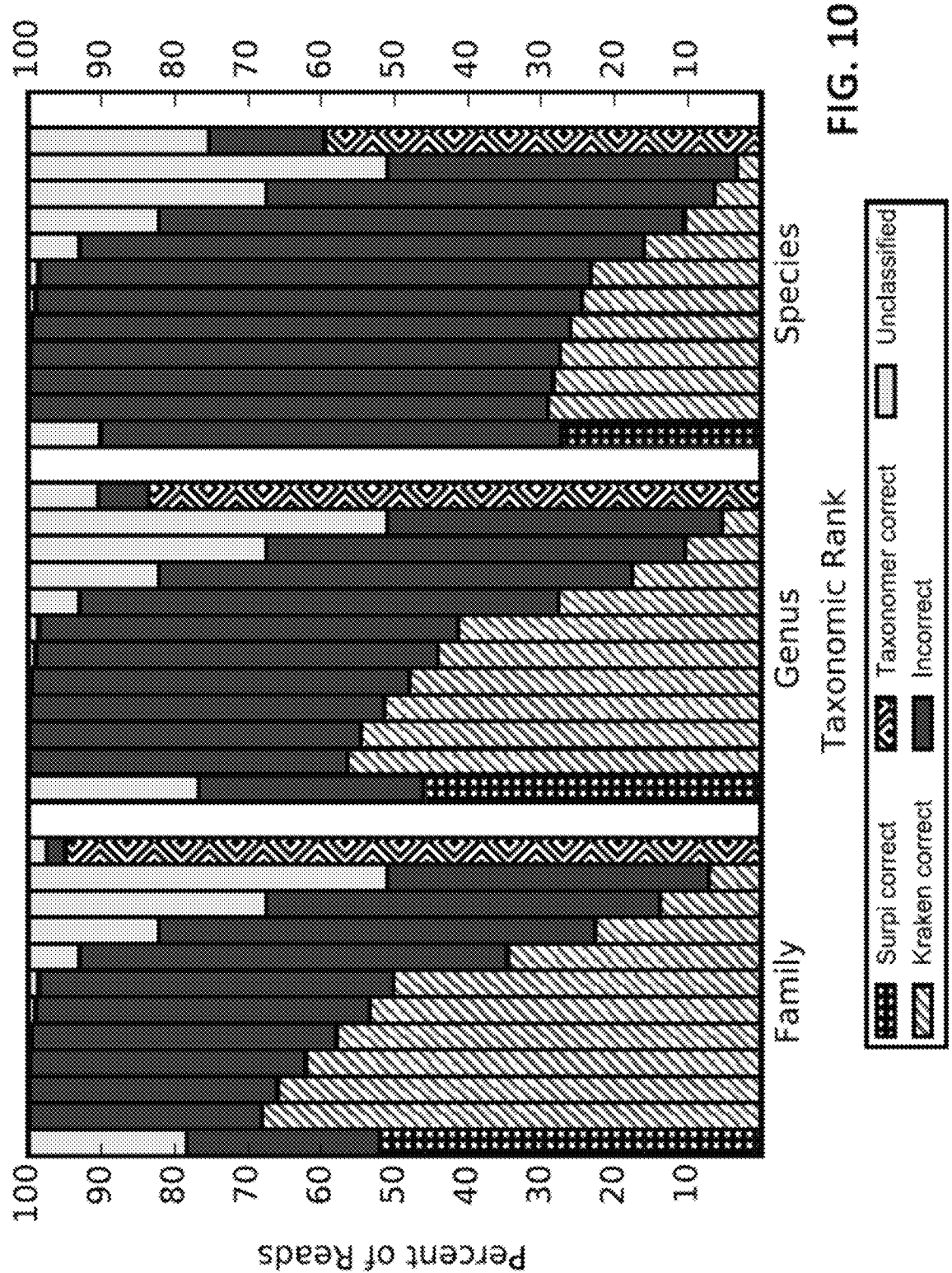
FIG. 10 shows the effect of different confidence cut-offs of Kraken compared to an embodiment of Taxonomer and SURPI.

Performance of classification tools is frequently only tested with synthetic reads derived from the reference database; such that perfect matches exist for all synthetic reads. For microbial classification, this is a highly artificial challenge, as novel species or strains are routinely encountered in clinical or environmental samples. To provide a more realistic challenge, synthetic reads were generated from bacterial 16S rRNA sequences in the SILVA database lacking perfect matches in Taxonomer's Greengenes-derived reference database (468 of 1013 source references, 46%, had no perfect match in the classification database, Table 12). Taxonomer employed a marker gene approach and a custom Greengenes-derived database for prokaryotic classification. Classification of the synthetic reads by Taxonomer, SURPI, and Kraken was compared using each tool's default settings and databases: nt (SURPI), RefSeq (Kraken), and Greengenes 99% OTU (Taxonomer). Kraken reports the taxon identifier for each read's final taxonomic assignment. An accessory script (Kraken-filter) can be used to apply confidence scores, although it was found that this value had little impact on results of the benchmarks (see FIG. 10). SURPI reports the best hit for its mapping tools, (SNAP, RAPSearch2), which were used for comparison. The results of this comparison (FIG. 2A) show that at the species level, for example, Taxonomer correctly classified 59.5%, incorrectly classified 15.7%, and failed to classify 24.8% of the reads. By comparison, Kraken classified 29% of the reads to the correct species, and exhibited a high false-positive rate, classifying every remaining read (71%) incorrectly. The results for SURPI have been split into two columns to reflect the fact that SURPI, unlike Taxonomer and Kraken, classifies each read from mate-pair reads independently, and in many cases these assignments are discordant (Table 11). Thus, the right-hand portion of the SURPI column records the classification rates when either read from a mate pair was classified correctly; the left-hand portion, records the rates for classifying both mates to the same taxon. As can be seen, SURPI underperforms both Taxonomer and Kraken.

TABLE 12

Sequence identity of full-length SILVA references used to generate synthetic read sets for FIGS. 2A-D and FIGS. 8-10 compared to the most similar reference sequence in the 'Classifier' database. Synthetic read sets were constructed using 1,013 randomly selected bacterial 16S sequences from the SILVA (release 119) database. The same full-length SILVA references were compared to the 'Classifier' reference database (Greengenes, 99% OTU clustering) using BLAST to determine sequence identity. Almost half of the SILVA reference sequences used have only imperfect matches in the 'Classifier' reference database. Only reference with ≥97% sequence identity were used to construct synthetic read sets for FIGS. 2, 10, 12, and 13.

| % ID (SILVA vs. Greengenes) | n | % |
|---|---|---|
| 100 | 545 | 53.8 |
| 99.5-99.99 | 261 | 25.8 |
| 99-99.49 | 117 | 11.5 |
| 98.5-98.99 | 31 | 3.1 |
| 98-98.49 | 26 | 2.6 |
| 97.5-97.99 | 22 | 2.2 |
| 97-97.49 | 11 | 1.1 |
| Total | 1,013 | 100 |

Figure 2B:
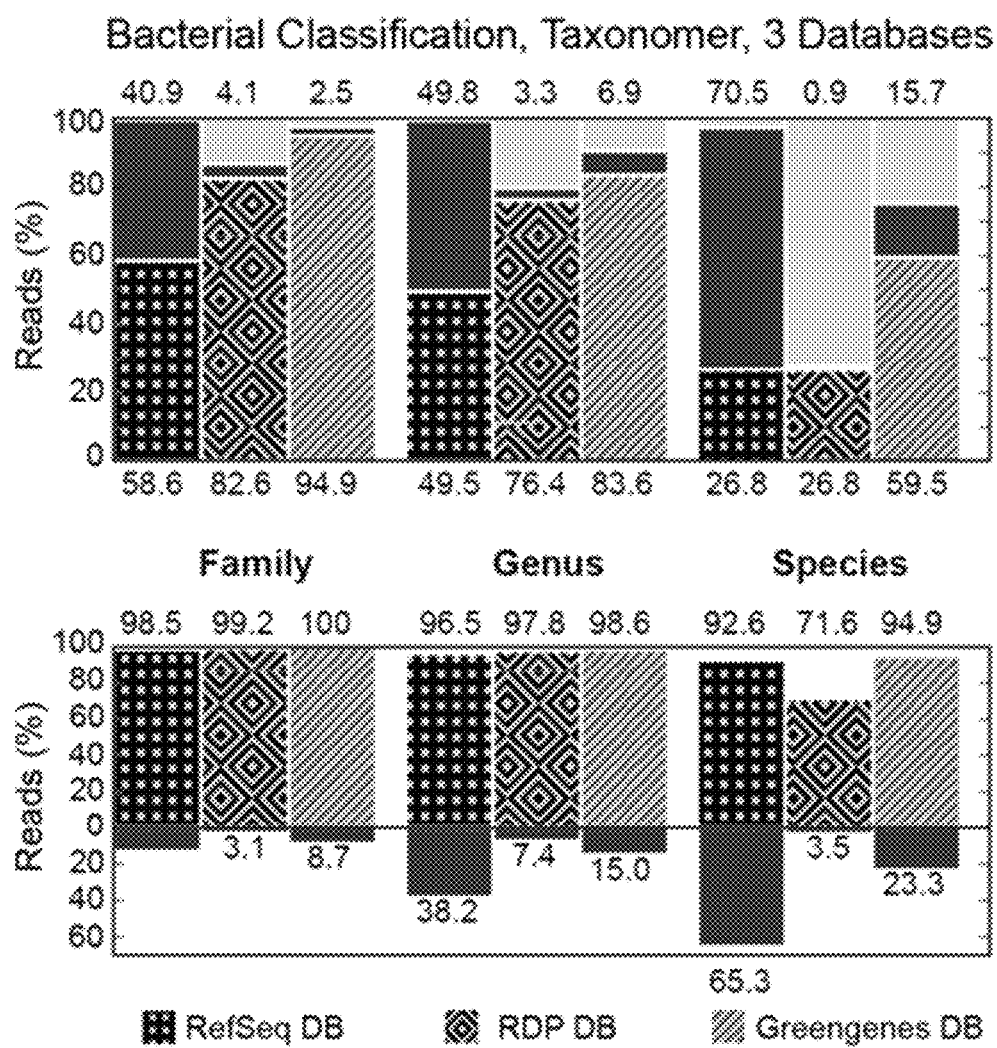

In order to show the effect of different databases on Taxonomer, the synthetic reads produced above were classified using RefSeq, the Kraken default, RDP, or Greengenes (Taxonomer default) databases (FIG. 2B). Using its default database, Taxonomer correctly classified 59.5% of the reads, and recovered 94.9% of species. Using Kraken's default database (RefSeq DB), Taxonomer's correctly classified 27% of the reads and recovered 71.6% of the species, similar to Kraken's results when using the same database: 29% and 71%, respectively. Also presented in FIG. 2B are Taxonomer's classification and recovery rates using the RDP database (RDP DB). For classification by RDP, classifications were resolved to the rank with a minimum confidence level of ≥0.5. Although Taxonomer misclassified very few reads using the RDP database, overall performance was substantially better using Taxonomer's default database.

Figure 2C:
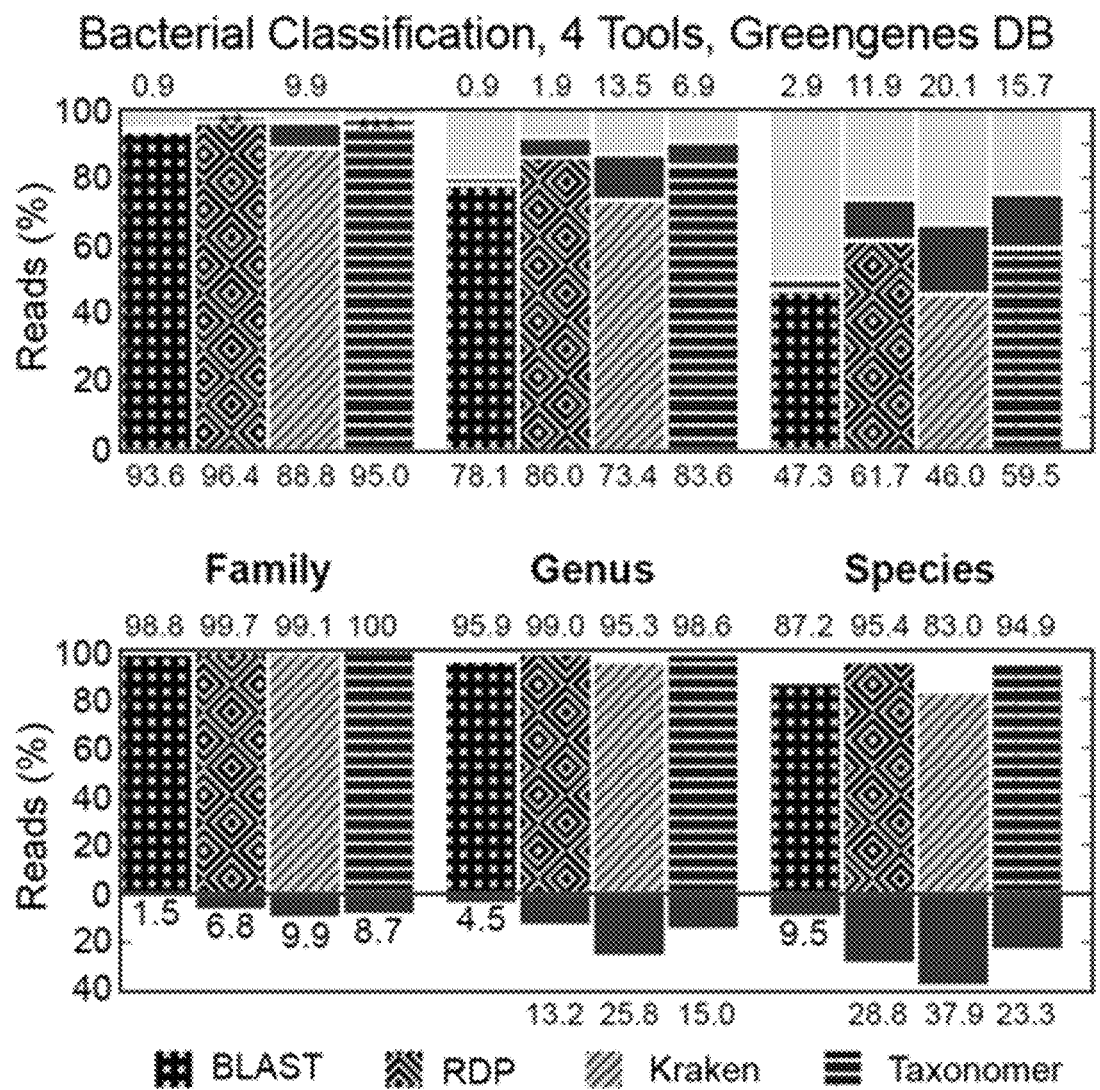
Figure 2D:
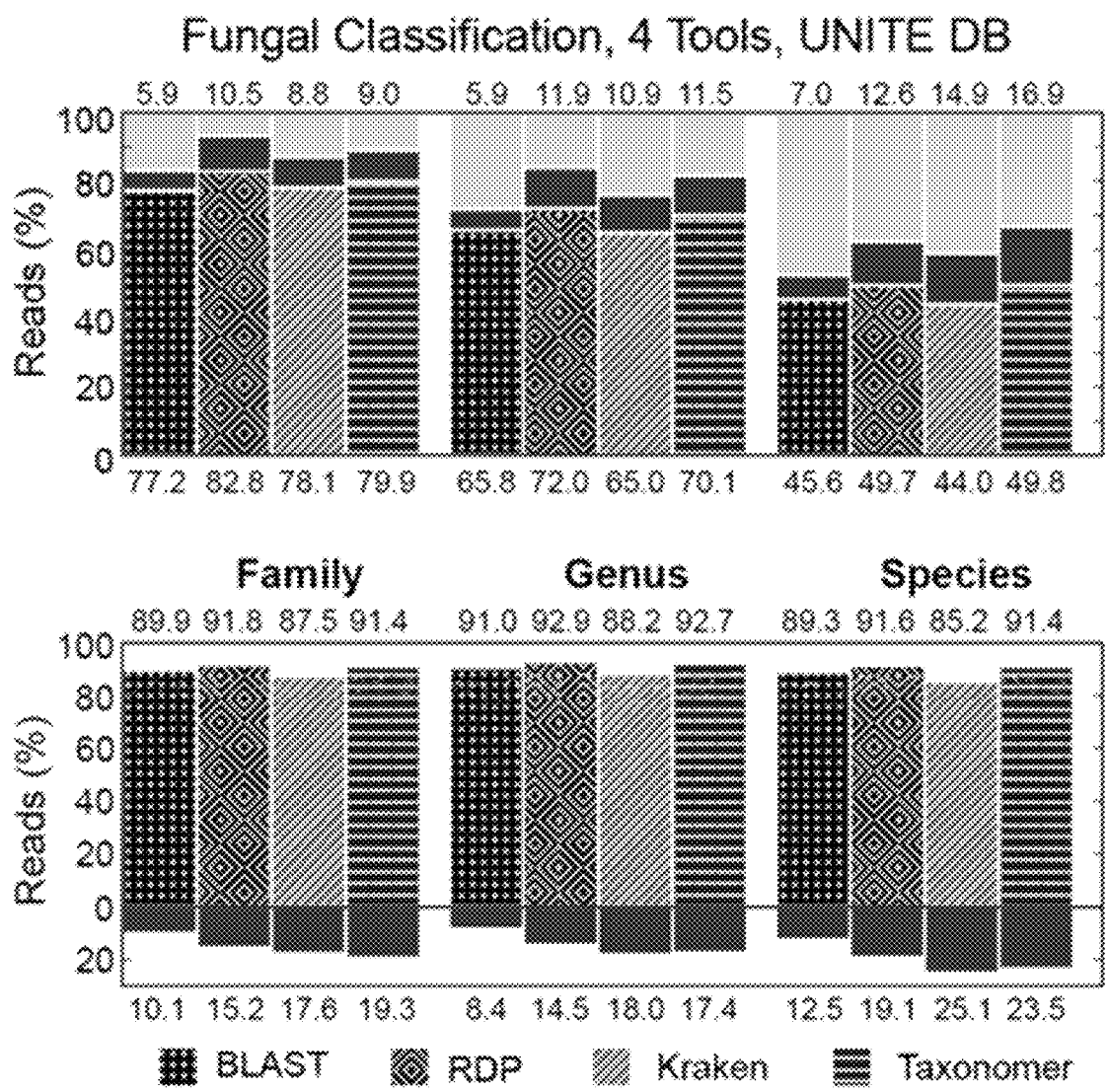
Figure 12A:
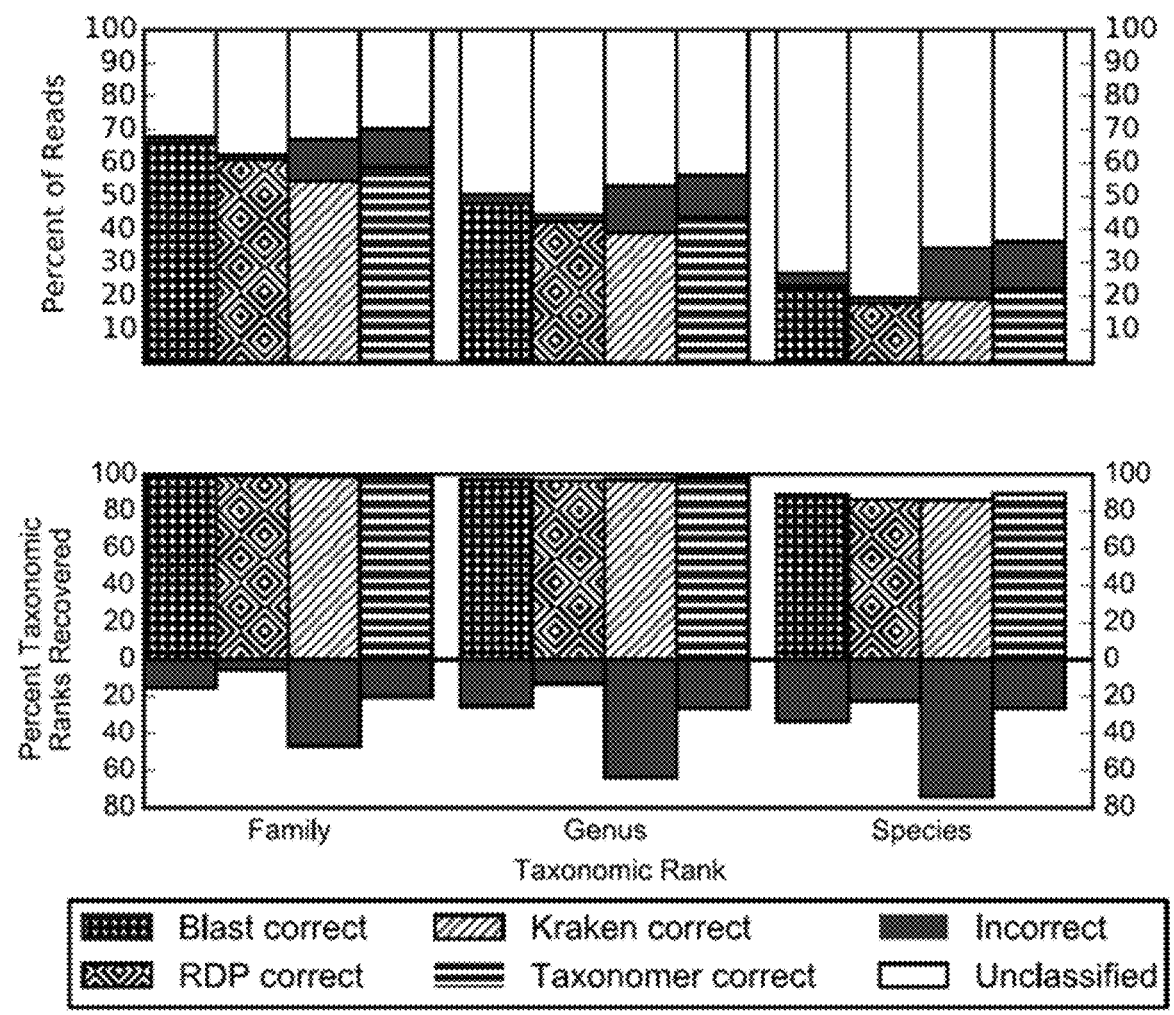
FIGS. 12A-B show the read-level (top) and taxon-level (bottom) bacterial classification accuracy of BLAST, the RDP Classifier, Kraken, and an embodiment of Taxonomer.
Figure 12B:
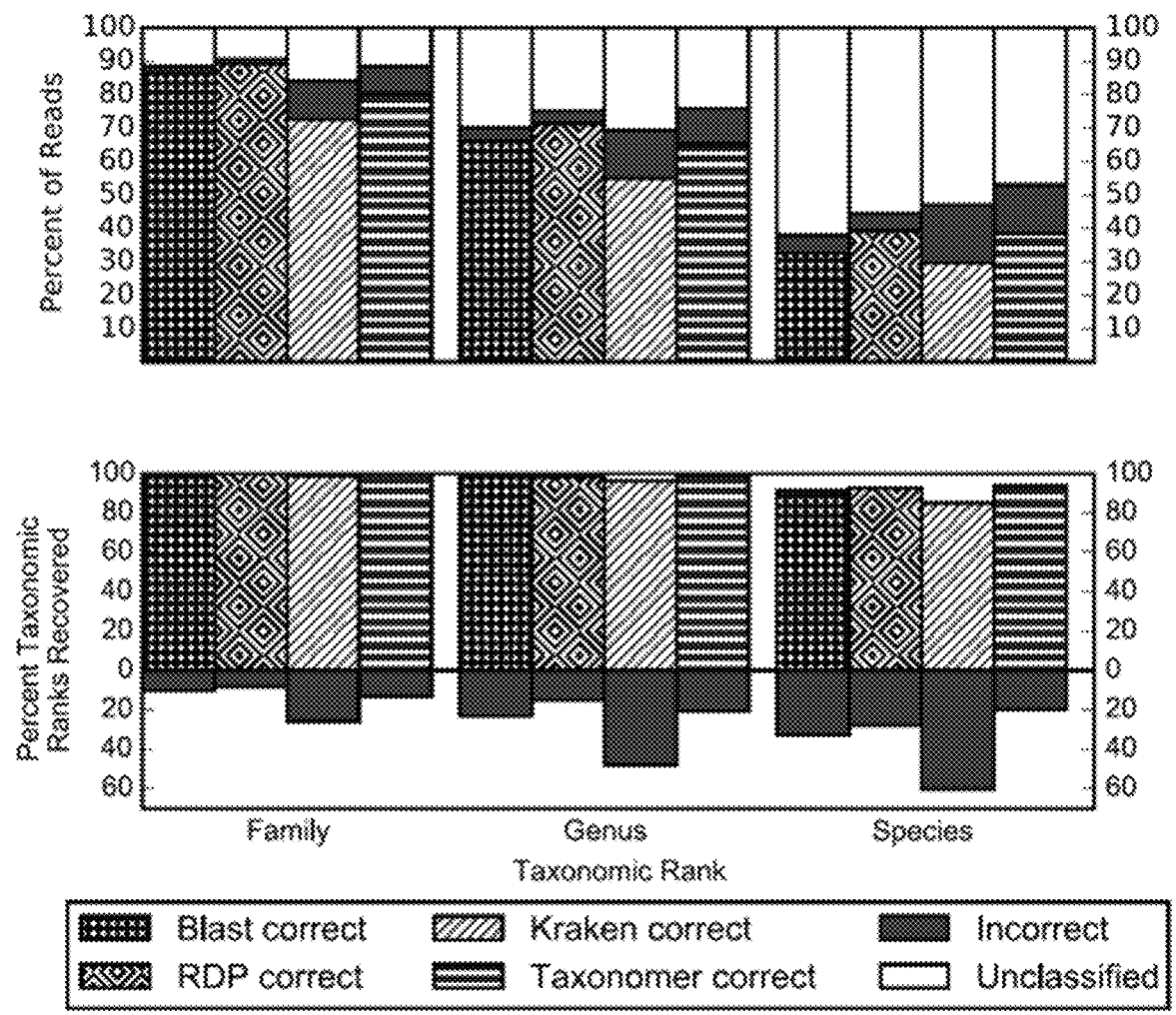
Figure 13:
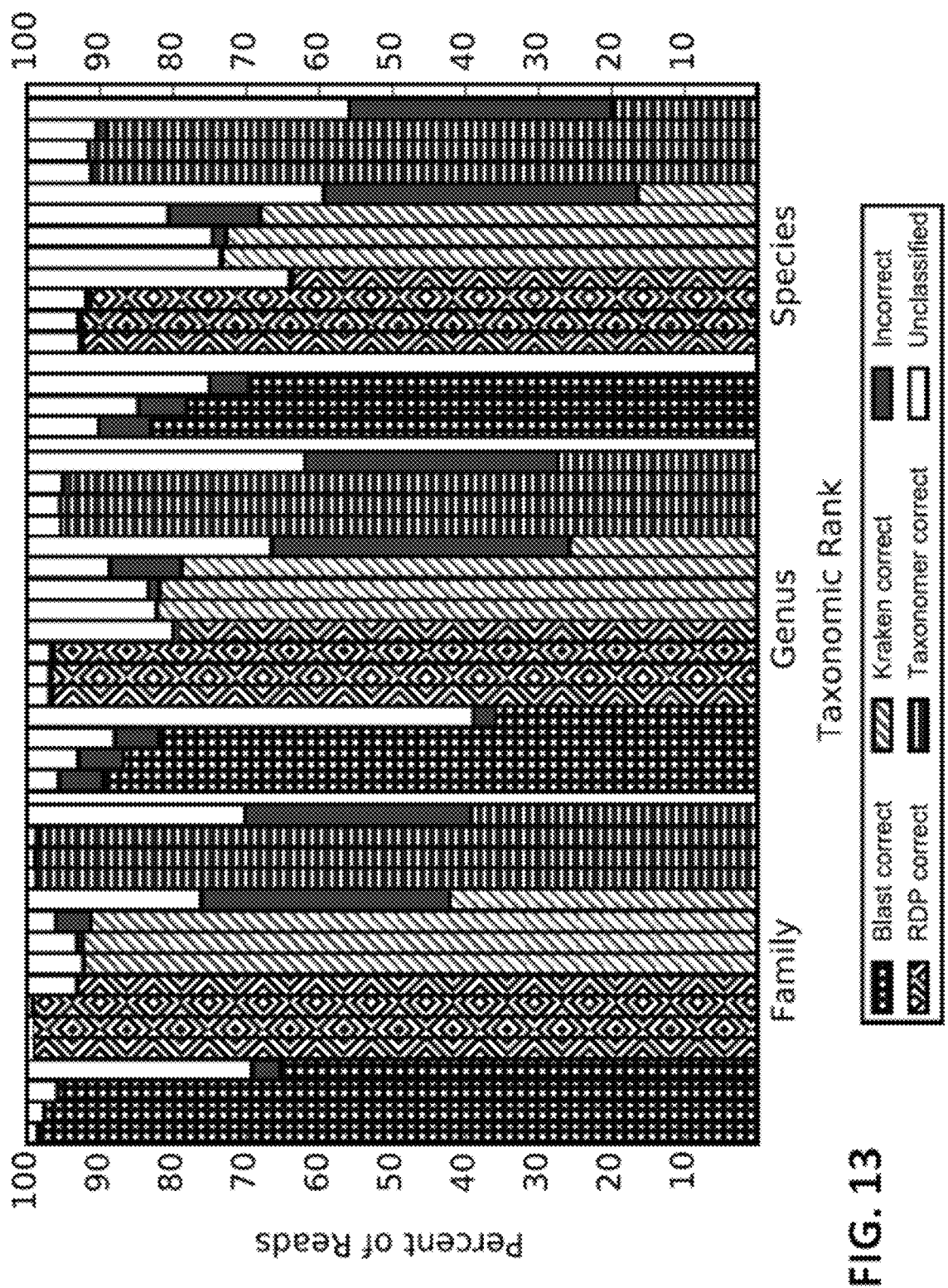
FIG. 13 illustrates the impact of sequencing error rates on different classification methods.

The four classification tools, MegaBLAST, the RDP Classifier, Kraken, and Taxonomer, were compared using Taxonomer's default 16S database. For this example, default MegaBLAST parameters were used. Top scoring references were identified and used to assign operational taxonomic units (OTUs) or species hypotheses (SHs) Multiple OTUs/SHs were assigned to reverse-translated reads when more than one OTU/SH reference shared 100% identity. If no OTU/SH had 100% identity to a read than all OTUs within 0.5% of the top hit were assigned to the read. The taxonomy of the assigned OTUs/SHs was compared and the highest rank in common was used to assign a taxonomic value to the read. The percent identity was used to determine the assignment of the highest taxonomic rank. Sequence reads with >97% identity to a reference were assigned to a species, >90% identity to a genus, and <90% to a family when lineage information was available at this rank. For classification by RDP, classifications were resolved as above to the rank with a minimum confidence level of ≥0.5. SURPI was not included in the comparison because there is no option to employ a user-provided database. As shown in FIG. 2C, Taxonomer's performance in classifying the simulated bacterial reads closely approximated that of the RDP Classifier, an established reference tool. At the species level, Taxonomer and RDP classified 59.5% and 61.4% of reads correctly, and recovery rates are very similar. Although Kraken's classification and recovery rates improved dramatically using Taxonomer's database compared to its own, Taxonomer still correctly classified 13.5% more reads compared to Kraken (59.5% vs. 46%) and also had a lower false positive-rate (15.7% vs. 20.1%). Taxonomer also outperformed Kraken on taxon recovery rate (94.9% vs. 83%), and Taxonomer's false-recovery rate was lower as well (23.3% vs. 37.9%). We examined the impact of read length (FIG. 12) and sequencing errors upon classification accuracy (see FIG. 13). FIG. 12 shows the read-level (top) and taxon-level (bottom) bacterial classification accuracy of BLAST, the RDP Classifier, Kraken, and Taxonomer run using the Greengenes 99% OTU database. The reads were either using 100 bp single-end (FIG. 12A) or (B) 100 bp paired-end (FIG. 12B) 16S rDNA reads simulated at 5× coverage from 1,013 randomly selected SILVA references with ≥97% sequence identity to reference sequences. The performance of Taxonomer was comparable to the RDP Classifier and superior to Kraken, whereas given the applied criteria BLAST was less sensitive but more specific. FIG. 13 shows family, genus and species level classification accuracy for BLAST, the RDP Classifier, Kraken and Taxonomer using the same read-length and database across error rates of 0.01%, 0.1%, 1%, 5%, and 10%. Performance improved for all tools as a function of read lengths. Taxonomer and Kraken were both more sensitive to sequencing errors than BLAST and the RDP Classifier due to their reliance on exact k-mer matches. Nevertheless, these same analyses demonstrate that Taxonomer's nucleotide classification algorithm is error resistant, with Taxonomer achieving greater classification accuracies than Kraken for sequences with less than 5% errors. FIG. 2D shows classification and recovery rates using Taxonomer's fungal database. As can be seen, the same general trends are seen in both FIG. 2C-D, demonstrating that Taxonomer's performance advantages are not restricted to bacterial classification.

TABLE 13

Accession numbers for published 16S amplicon data used in for bacterial abundance estimates (FIG. 2E), numbers of reads, and analysis times for the RDP Classifier and Taxonomer. Number of reads for reference (b) is based on mate pairs.

| Sample | Source | Ref. | Reads | RDP Classifier [min] | Taxonomer [min] |
|---|---|---|---|---|---|
| ERR498444 | Human gut | a | 20,469 | 285 | 0.91 |
| ERR498459 | Human gut | a | 8,413 | 303 | 0.45 |
| ERR498467 | Human gut | a | 16,864 | 426 | 0.62 |
| ERR498476 | Human gut | a | 19,066 | 402 | 0.96 |
| ERR498532 | Human gut | a | 20,458 | 315 | 1.02 |
| ERR498541 | Human gut | a | 18,803 | 354 | 0.78 |
| ERR498566 | Human gut | a | 12,612 | 200 | 0.60 |
| ERR498576 | Human gut | a | 10,070 | 258 | 0.49 |
| ERR498611 | Human gut | a | 19,506 | 342 | 0.96 |
| ERR498653 | Human gut | a | 14,311 | 225 | 0.61 |
| ERR502969 | Dog nose | b | 62,836 | 492 | 1.26 |
| ERR502989 | Human nose | b | 79,093 | 930 | 2.37 |
| ERR503004 | Kitchen floor | b | 74,061 | 594 | 2.00 |
| ERR503007 | Human hand | b | 67,144 | 615 | 1.41 |
| ERR503052 | Human nose | b | 54,569 | 468 | 0.87 |
| ERR503054 | Human hand | b | 77,382 | 822 | 2.67 |
| ERR503166 | Bedroom floor | b | 57,718 | 498 | 1.10 |
| ERR503209 | Kitchen floor | b | 64,996 | 534 | 1.91 |
| ERR503211 | Bathroom door knob | b | 70,964 | 630 | 1.44 |
| ERR503212 | Human nose | b | 124,363 | 852 | 3.27 |

Here Ref (a) and Ref (b) refer to the publications from which the data was derived: (Ref (a) was Subramanian, S. et al. Nature 510, 417-421 (2014); Ref (b) was Lax, S. et al. Science 345, 1048-1052 (2014)).

Figure 14A:
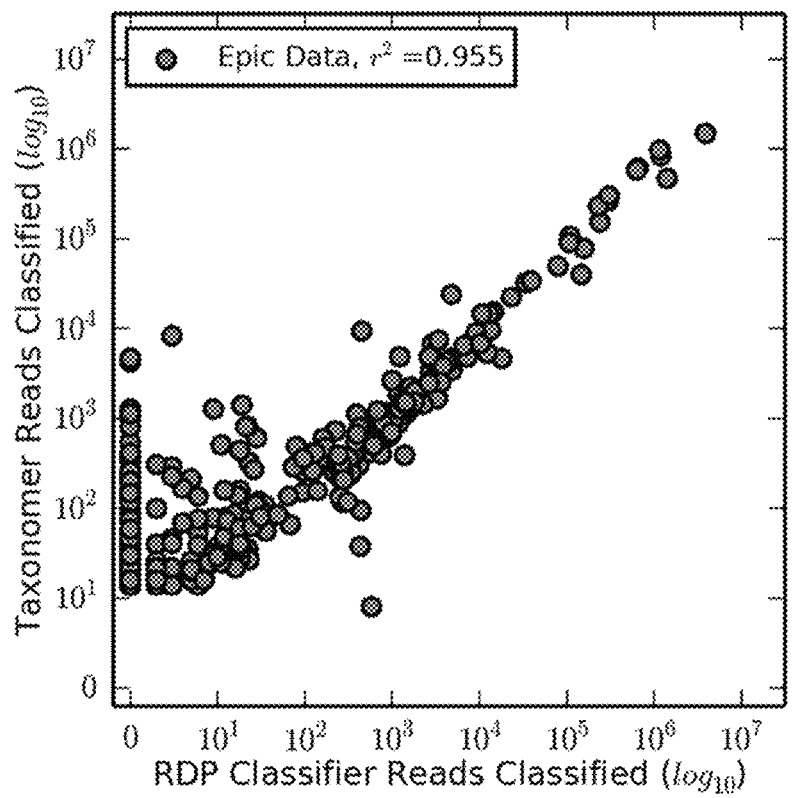
FIGS. 14A-D illustrate results showing that an embodiment of Taxonomer classifies bacterial 16S rRNA reads at >200-fold increased speed compared to the RDP Classifier while providing highly comparable bacterial community profiles.
Figure 14B:
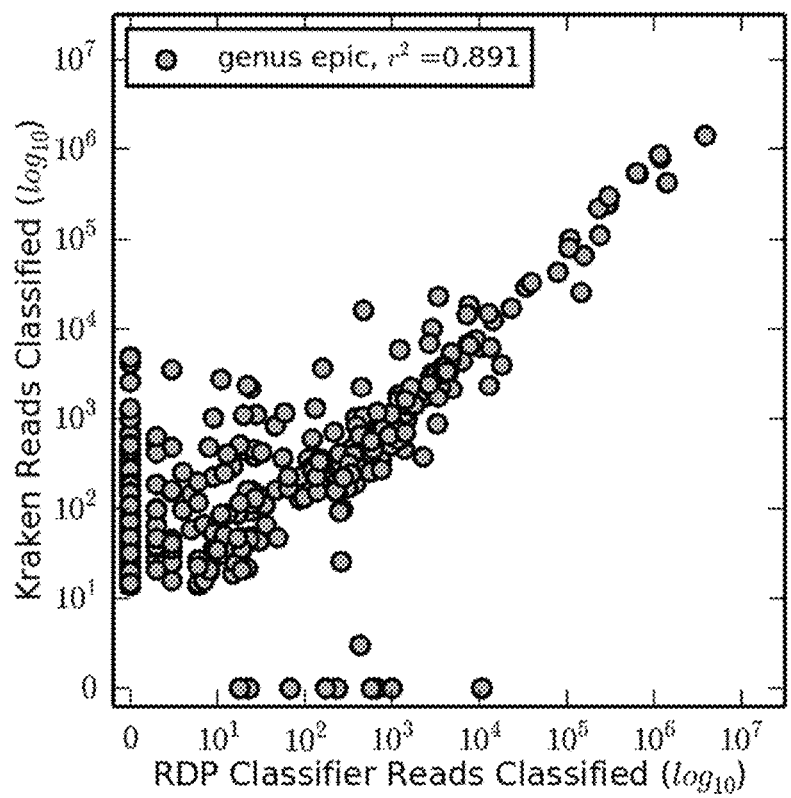
Figure 14C:
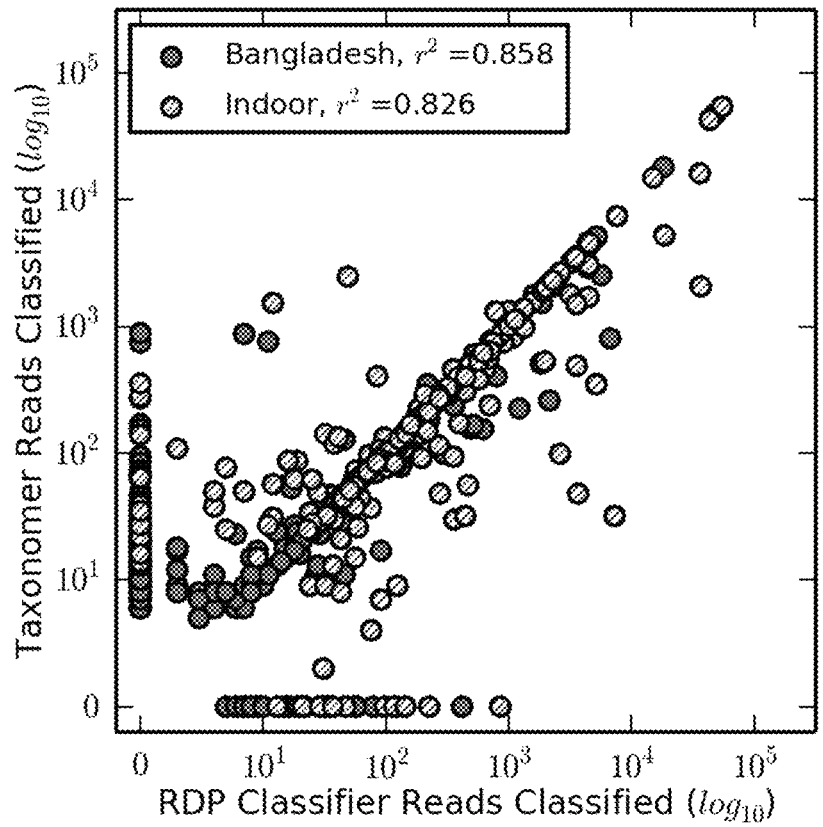
Figure 14D:
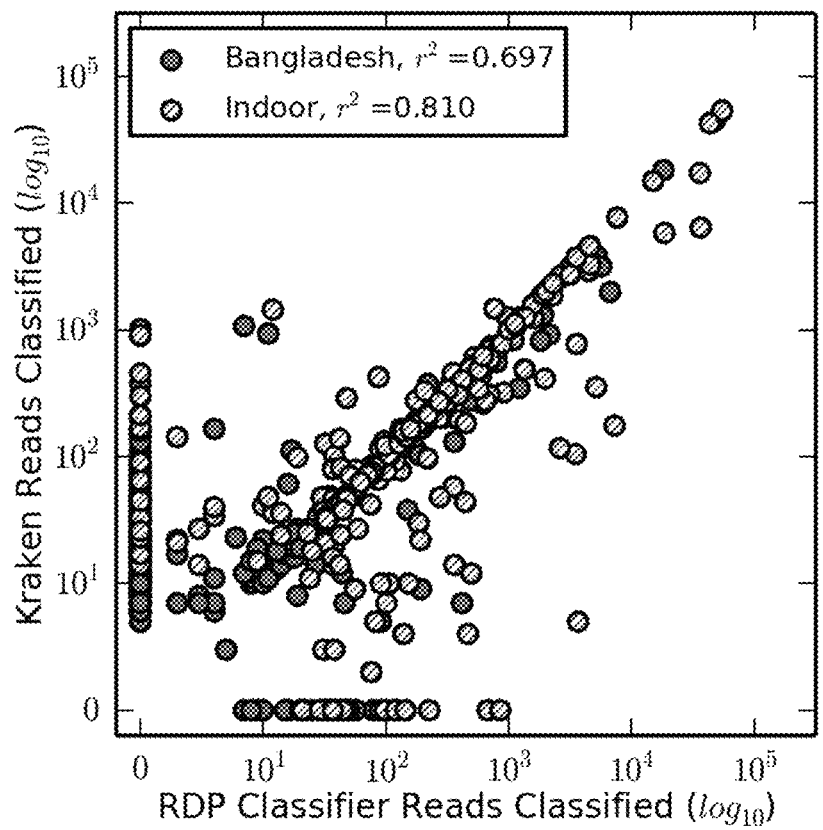
Figure 15:
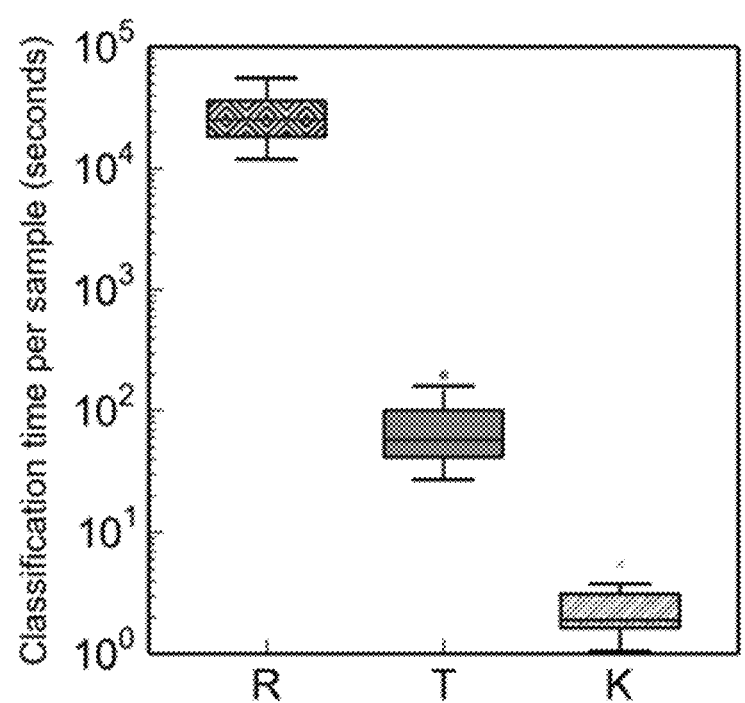
FIG. 15 shows example analysis times for the RDP Classifier (R), an embodiment of Taxonomer (T), and Kraken (K) for classification of samples shown in FIGS. 14A-D.

Since quantifying microbial community composition is a frequent goal of metagenomics studies, we also compared Taxonomer's bacterial abundance estimates to those of the RDP Classifier using recently published 16S amplicon sequencing data (see Table 13) and RNA-Seq-based metagenomics (FIG. 2E). Taxonomer's abundance estimates were highly correlated with RDP's across taxonomic levels for all three datasets. Taxonomer provided highly comparable community profiles at >200-fold increased speed (Spearman correlation coefficient: r2=0.955 for 2×100 bp reads); average of 1,630,923 2×100 bp reads/sample; average run times were 27.4 minutes (Taxonomer) versus 120.7 hours (RDP Classifier) on 1 CPU. FIGS. 14A and 14B show RNA-Seq metagenomics results comparing Taxonomer Kraken using the Greengenes 99% OTU reference database. Correlation of Kraken with abundance estimates based on the RDP Classifier were weaker (Spearman correlation coefficient: $r^2$=0.891 2×100 bp reads); average run times were 42 seconds/sample. FIG. 14C and FIG. 14D show 16S rRNA gene amplicon sequences of variable region 4 from two published data sets generated on HiSeq2000 (dark green, 1×150 bp reads) and MiSeq instruments (light green, 2×150 reads). The correlation of abundance estimates (limited to taxa with relative abundance>0.1% per sample) are shown for Taxonomer and the RDP Classifier (FIG. 14C, Spearman correlation coefficients: $r^2$=0.858 for 1×150 bp reads, and $r^2$=0.826 for 2×150 bp reads). The average number of reads per sample was 44,685 and the average processing times (using 1 CPU) were 1:28 minutes for Taxonomer and 7.9 hours for the RDP Classifier. The correlation of abundance estimates as determined Kraken using the Greengenes 99% OTU reference database with abundance estimates based on the RDP Classifier were weaker (Spearman correlation coefficient: $r^2$=0.697 for 1×150 bp reads, and $r^2$=0.810 for 2×150 bp reads); average run times were 2.5 seconds/sample. Spearman Correlation coefficients (p) were 0.96 and 0.997 (order) and 0.858 and 0.826 (genus) for 16S amplicon data as well as 0.992 (order) and 0.955 (genus) for RNA-Seq (FIGS. 2E and 14). However, Taxonomer's average analysis times were 260 to 440-fold faster (FIG. 2E and FIG. 15). Collectively, these benchmarks illustrate the important role of Taxonomer's classification databases and the power and speed of its classification algorithm.

Example 7: Viral Classification

Figure 8B:
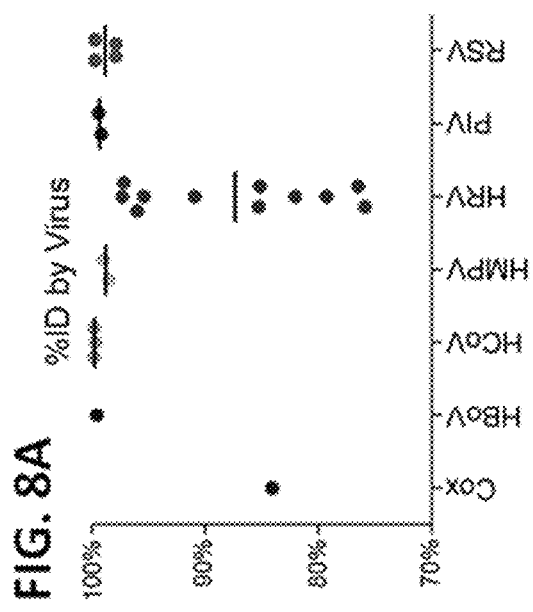

In this example, the embodiment of Taxonomer described in Example 1 was used to classify reads derived from viral sources. RNA-Seq data from 24 samples known to harbor particular respiratory viruses was used. The mean pairwise, genome-level sequence identities of the 24 respiratory viruses to reference sequences in the NCBI nt database were 93.7% (range: 75.9-99.8%; see Table 14 and FIG. 8A). The sequencing reads from each sample were binned by Binner, and the 'viral' and 'unclassified' bins (see FIGS. 1A and 6C) were taxonomically classified by Protonomer, RAPSearch2 (default and fast settings), and DIAMOND (default and sensitive settings). RAPSearch 2 is employed by SURPI (see Zhao, Y., Tang, H & Ye, Y. *RAPSearch2: a fast and memory-efficient protein similarity search tool for next-generation sequencing data. Bioinformatics* 28, 125-126 (2012)), whereas DIAMOND is an ultrafast, BLAST-like protein search tool (see Buchfink, B., Xie, C. & Huson, D. H. *Fast and sensitive protein alignment using DIAMOND. Nature methods* (2014)). Protonomer showed a sensitivity of 94.6±2.7%, RAPSearch2 had a sensitivity of 95.0±2.2% in default mode and 94.8±2.2% in fast mode; both were more sensitive than DIAMOND, which had a sensitivity of 90.5±2.7% in default mode and 90.5±2.7% in sensitive mode. Conversely, Protonomer (90.7±17.1%) and DIAMOND (default: 92.0±17.1%, sensitive: 91.9±14.9%) provided significantly higher specificity than RAPSearch2 in default mode (88.0±20.0%). Protonomer classified reads faster than RAPSearch2 (24-fold compared to default mode, 11-fold compared to fast mode) and DIAMOND (2.6-fold compared to default mode, 3.3-fold compared to sensitive mode) on a computer with 16 central processing units. Protonomer demonstrated the best overall performance, being more sensitive (median 94.6%) than DIAMOND (90.5%) and more specific (90.7%) than RAPSearch2 (88.0%) (FIG. 3A-C). True viral reads were determined by mapping all reads to a manually constructed viral consensus genome sequence for each sample. As expected, sensitivity for all tools correlated with pairwise identities of viral genome to reference sequences, with DIAMOND being most vulnerable to novel sequence polymorphisms (FIG. 8B). Of note, DIAMOND does not support joint analysis of paired sequencing reads. In this comparison, the results of the mate pair with the lowest E-value were used rather than reconciling results of read mates, which likely resulted in optimistic performance estimates for DIAMOND. Protonomer is also the fastest of the three tools, classifying $10^4$ to $10^6$ reads/sample (Protonomer: 14 seconds; DIAMOND: 37 seconds in default and 46 seconds in sensitive mode; RAPSearch2: 343 seconds in default and 169 seconds in rapid modes, FIG. 8).

Taxonomer was further used to analyze published RNA-Seq data from three patients in whom viral pathogens with significance to public health were detected: a serum sample from a patient with hemorrhagic fever caused by a novel rhabdovirus (Bas Congo Virus, FIG. 3D); a throat swab from a patient with avian influenza (H7N9 subtype, FIG. 3E), and a plasma sample from a patient with Ebola virus (FIG. 3F). Taxonomer detected the relevant viruses in all three cases, even after removal of the target sequence from the reference database, thus demonstrating the utility of Taxonomer for rapid virus detection and discovery in public health emergencies. Its web-based deployment enables the rapid sharing and review of analysis results, even across great geographic distances.

TABLE 14

Figure 8C:
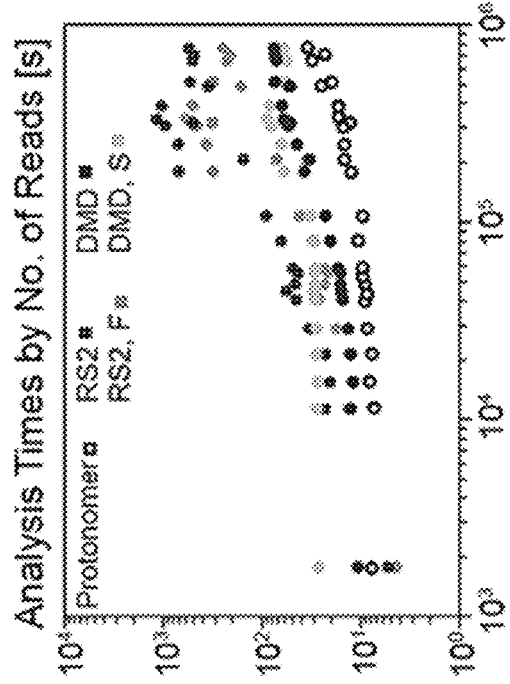

Viruses, percent nucleotide-level identity to reference sequences in the NCBI nt database, as well as numbers of total and viral reads for pediatric upper respiratory tract specimens used to compare 'Protonomer', RAPSearch2, and DIAMOND for protein-level classification of viral sequences (see FIGS. 3, 8 & 9). HCoV—human coronavirus, HBoV—human bocavirus, HMPV—human metapneumovirus, HRV—rhinovirus, PIV—parainfluenza virus, RSV—respiratory syncytial virus.

| Virus | Nucleotide ID | GenBank Accession | Total Reads | Target Reads (n) | Target Reads (%) |
|---|---|---|---|---|---|
| HCoV (HKU1) | 99.8% | KF686344 | 317,354 | 305,544 | 96.3% |
| HCoV (NL43) | 99.8% | JQ765567 | 44,825 | 20,800 | 46.4% |
| HCoV (OC43) | 99.7% | AY903460 | 15,515 | 6,919 | 44.6% |
| Coxsackie Virus B4 | 84.1% | KF878966 | 21,399 | 1,027 | 4.8% |
| HBoV | 99.6% | JQ923422 | 206,869 | 1,119 | 0.5% |
| HMPV | 98.5% | GQ153651 | 80,362 | 7,059 | 8.8% |
| HMPV | 99.0% | EF535506 | 55,240 | 2,683 | 4.9% |
| HRV-A | 90.9% | EF173415 | 11,369 | 2,413 | 21.2% |
| HRV-C | 85.2% | DQ875932.2 | 490,829 | 491 | 0.10% |

TABLE 14-continued

Viruses, percent nucleotide-level identity to reference sequences in the NCBI nt database, as well as numbers of total and viral reads for pediatric upper respiratory tract specimens used to compare 'Protonomer', RAPSearch2, and DIAMOND for protein-level classification of viral sequences (see FIGS. 3, 8 & 9). HCoV—human coronavirus, HBoV—human bocavirus, HMPV—human metapneumovirus, HRV—rhinovirus, PIV—parainfluenza virus, RSV—respiratory syncytial virus.

| Virus | Nucleotide ID | GenBank Accession | Total Reads | Target Reads (n) | Target Reads (%) |
|---|---|---|---|---|---|
| HRV-C | 85.3% | DQ875932.2 | 704,819 | 394 | 0.06% |
| HRV-C | 79.3% | JF436925.1 | 662,784 | 200 | 0.03% |
| HRV-C | 97.3% | JX074056 | 385,808 | 208,446 | 54.0% |
| HRV-C | 82.1% | JF317017 | 306,436 | 232,451 | 75.9% |
| HRV-C | 97.2% | JX074056 | 246,973 | 35,474 | 14.4% |
| HRV-C | 75.9% | KF958311 | 28,862 | 2,657 | 9.2% |
| HRV-C | 96.0% | JN990702 | 330,157 | 252,416 | 76.5% |
| HRV-C | 76.5% | GQ223228 | 179,888 | 153,429 | 85.3% |
| HRV-C | 95.4% | GQ323774 | 58,005 | 1,369 | 2.4% |
| PIV-1 | 99.2% | JQ901989 | 107,818 | 9,392 | 8.7% |
| PIV-3 | 99.4% | KF530232 | 48,547 | 15,651 | 32.2% |
| RSV-A | 99.7% | KF826849.1 | 762,085 | 2,218 | 0.29% |
| RSV-B | 97.9% | JQ582843 | 1,784 | 1,035 | 58.0% |
| RSV-B | 97.9% | JQ582843 | 40,707 | 32,047 | 78.7% |
| RSV-B | 99.7% | JN032120.1 | 516,693 | 495,469 | 95.9% |

Example 8: Human mRNA Transcript Profiling

In this example, the embodiment of Taxonomer described in Example 1 was used to profile a host response, which is of growing interest for infectious diseases testing and for quality-control of cell lines and tissues where microbial contaminants may confound transcript expression profiles. Taxonomer is the only ultrafast metagenomics tool with this capability. Taxonomer's default databases included ERCC control sequences, allowing users to normalize transcript counts. By default these reference transcripts and corresponding gene models (GTF file) from the ENSMBL human reference sequence, GRCh37.75. A k-mer of size of 20 was used, which works well for mapping reads to human transcripts.

TABLE 15

Accession numbers for human brain RNA-Seq data used to compare with MAQC qPCR data

| Sample | Source | Reads |
|---|---|---|
| SRR037452 | Human brain | 11,712,885 |
| SRR037453 | Human brain | 11,413,794 |
| SRR037454 | Human brain | 11,816,021 |
| SRR037455 | Human brain | 11,244,980 |
| SRR037456 | Human brain | 12,081,324 |
| SRR037457 | Human brain | 11,365,146 |
| SRR037458 | Human brain | 11,616,331 |

Figure 4A:
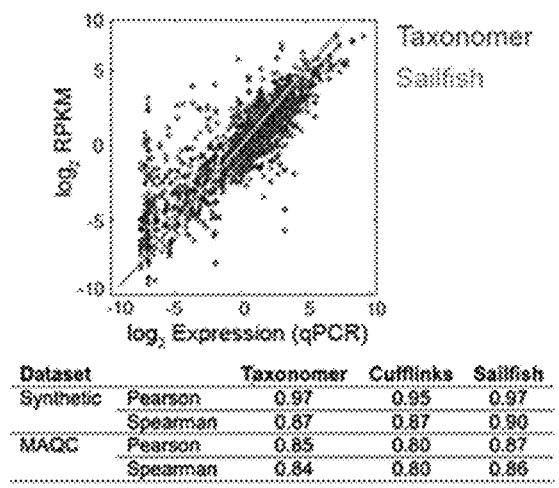
Figure 4B:
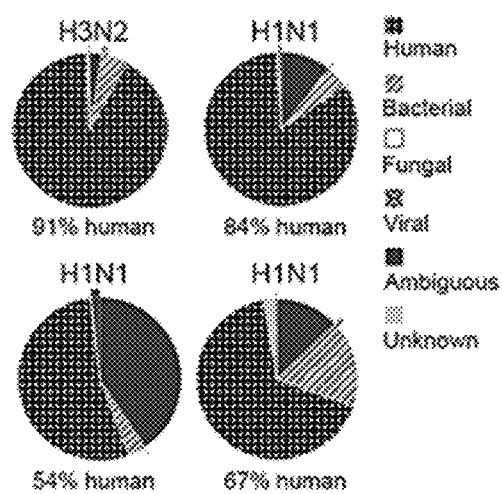
Figure 4C:
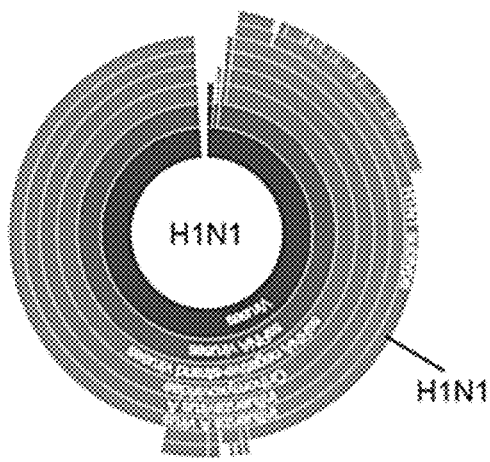
Figure 4D:
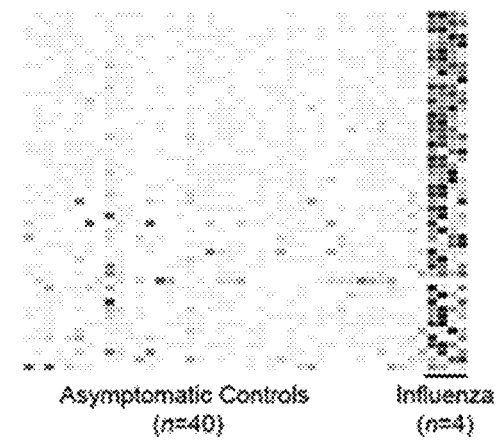

Taxonomer's expression profiles were compared to those of standard transcript expression profiling tools Sailfish and Cufflinks, as well as quantitative PCR. Gene-level Pearson and Spearman correlation coefficients for RNA-seq versus qPCR were 0.85 and 0.84 for Taxonomer, 0.87 and 0.86 for Sailfish, and 0.80 and 0.80 for Cufflinks, respectively. These results showed that Taxonomer's quantification of synthetic reads and a commercially available RNA standard (MAQC specifically, human brain tissue samples, see Table 15) was accurate over a broad range of transcript abundance. Indeed, accuracy was intermediate between Sailfish's and Cufflink's (FIG. 4A). To demonstrate the utility of Taxonomer's capacity for simultaneous pathogen detection and transcript expression profiling, Taxonomer was used to analyze RNA-Seq data from respiratory samples of patients with influenza A virus infection (n=4) with varying abundance of host versus microbial RNA (FIG. 4B) and compared mRNA expression profiles to those of asymptomatic controls (n=40). Influenza A virus was detected in all samples by Taxonomer (FIG. 4C). Normalized gene-level expression of the 50 most differentially expressed host genes is shown in FIG. 4D. Expression profiles for 17 host genes were significantly higher in influenza-positive patients, (Table 16, examples in FIG. 4F) and their expression profiles clearly differentiated cases from controls in a principal component analysis with PC1 accounting for 84.7% of the total variance (FIG. 4E).

Gene ontology assignments for the top 50 differentially expressed genes were also analyzed for enrichment of biological processes (FIG. 4G) and molecular functions (FIG. 4H), demonstrating their involvement in recognition of pathogen-associated molecular patterns and antiviral host response. Most but not all of these genes are known to be differentially regulated in response to influenza virus or other viral infections in vitro or in peripheral blood of patients. Together, these results demonstrate the accuracy and power for discovery and a potential future diagnostic application of Taxonomer's combined pathogen detection and host response profiling.

Taxonomer's performance was compared to Sailfish and Cufflinks using synthetic RNA-seq reads (2×76 bp, n=15,000,000) generated with the Flux Simulator tool (see Griebel, T. et al. Modelling and simulating generic RNA-Seq experiments with the flux simulator. Nucleic acids research 40, 10073-10083 (2012)); see Table 17 for parameters. TopHat (see Trapnell, C., Pachter, L. & Salzberg, S. L. TopHat: discovering splice junctions with RNA-Seq. Bioinformatics 25, 1105-1111 (2009)) was used to produce alignments for Cufflinks. Like Taxonomer, Sailfish does not need external alignment information.

TABLE 16

Genes (n = 17) that are differentially regulated in nasopharyngeal and oropharyngeal swabs from children with pneumonia who tested positive for influenza virus (n = 4) compared to asymptomatic controls (n = 40). Read counts and p-values (raw and adjusted) are shown. A—controls; B—influenza

| Gene ID | Base Mean A | Base Mean B | Fold Change | p | p (adj) |
|---|---|---|---|---|---|
| IFIT1 | 0.7 | 73.4 | 104.5 | 7.1E−19 | 1.5E−14 |
| IFI6 | 0.5 | 31.4 | 64.8 | 6.3E−13 | 6.7E−09 |
| IFIT2 | 2.1 | 135.5 | 63.8 | 7.8E−09 | 5.5E−05 |
| ISG15 | 1.4 | 61.2 | 43.3 | 1.4E−08 | 6.4E−05 |
| OASL | 0.6 | 20.3 | 33.3 | 1.5E−08 | 6.4E−05 |
| IFIT3 | 2.1 | 81.2 | 38.7 | 5.4E−08 | 1.9E−04 |
| NT5C3A | 0.7 | 20.1 | 30.7 | 3.3E−07 | 9.9E−04 |
| MX2 | 1.4 | 27.4 | 19.2 | 4.0E−07 | 1.1E−03 |
| IFITM1 | 2.4 | 32.8 | 14.0 | 6.4E−07 | 1.5E−03 |
| CXCL10 | 0.6 | 37.3 | 64.6 | 9.0E−07 | 1.9E−03 |
| IFI44L | 1.5 | 26.6 | 17.8 | 1.6E−06 | 3.1E−03 |
| MX1 | 4.2 | 56.5 | 13.5 | 1.8E−06 | 3.2E−03 |
| IFIH1 | 1.4 | 21.3 | 15.0 | 9.7E−06 | 1.6E−02 |
| OAS2 | 2.8 | 37.5 | 13.2 | 1.3E−05 | 1.9E−02 |
| SAMD9 | 2.8 | 61.9 | 22.5 | 2.6E−05 | 3.7E−02 |
| RSAD2 | 1.4 | 47.0 | 33.7 | 2.9E−05 | 3.8E−02 |
| DDX58 | 1.1 | 16.6 | 15.3 | 3.9E−05 | 4.8E−02 |

TABLE 17

Flux Simulator parameters used to generate simulated RNAseq reads for benchmarking transcript assignment. Following the benchmarks used for Sailfish we filtered the transcript GTF using the gffread utility with the flags-C-M-E and -T, as well as any transcripts consisting solely of Ns. The GTF was sorted using the FluxSimulator sortGTF command and used to generate the synthetic data for benchmarking.

| Stage | Parameters |
|---|---|
| Expression | NB_MOLECULES 5000000 |
| | REF_FILE_NAME |
| | Homo_sapiens_ENSMBL_37.75.gtf |
| | TSS_MEAN 50 |
| | POLYA_SCALE NaN |
| | POLYA_SHAPE NaN |
| Fragmentation | FRAG_SUBSTRATE RNA |
| | FRAG_METHOD UR |
| | FRAG_UR_ETA NaN |
| | FRAG_UR_D0 1 |
| Reverse Transcription | RTRANSCRIPTION YES |
| | RT_PRIMER RH |
| | RT_LOSSLESS YES |
| | RT_MIN 500 |
| | RT_MAX 5500 |
| Filtering & Amplification | FILTERING YES |
| | GC_MEAN NaN |
| | PCR_PROBABILITY 0.05 |
| Sequencing | READ_NUMBER 150000000 |
| | READ_LENGTH 76 |
| | PAIRED_END YES |
| | ERR_FILE 76 |
| | FASTA YES |
| | UNIQUE_IDS NO |

Example 9: Identification of Infection and Contamination

In this example, the embodiment of Taxonomer described in Example 1 was used to identify infection and contamination in a biological sample. Taxonomer was used to analyze RNA-Seq data from the plasma of patients suspected of being infected with Ebola virus, but who had tested negative for Ebola virus (FIG. 5A). Taxonomer detected HIV, Lassa virus, Enterovirus (typed by Taxonomer as Coxsackievirus), and GB virus C. FIG. 16B shows that Taxonomer classified a reported Enterovirus as Enterovirus A in plasma from a patient with suspected Ebola virus disease in Sierra Leone (SRR1564825). Mean sequencing depth was 162× covering 96% of the reference sequence (AY421765). Analysis of a manually constructed viral consensus genome sequences identified the strain as sharing 80% nucleotide sequence identity with Coxsackievirus A7, strain Parker. Taxonomer also detected the previously unrecognized bacterial infections Chlamydophila psittaci and Elizabethkingia meningoseptica, which may have caused a patients' symptoms (FIGS. 5A and 16). FIG. 16A shows that Taxonomer detected Elizabethkingia meningoseptica in sample SAMN03015718 (SRR1564828). The mean coverage of the 16S rRNA gene was 16,162-fold and the consensus sequence shared 99.9% nucleotide sequence identity with the type strain of E. meningoseptica (AJ704540, ATCC 13253). Coverage of the bacterial 16S rRNA gene was >1,000× for both cases and pairwise sequence identities to type strain sequences were >99%, enabling reliable identification. The 16S rRNA gene of C. psittaci was covered a mean of 7,035-fold with the consensus 16S rRNA sequence from this isolate sharing 99.9% identity with the type strain (6BC, ATCC VR-125, CPU68447). Positions of 2 single-nucleotide polymorphisms are highlighted in red in FIG. 5A. C. psittaci is the causative agent of psittacosis, an uncommon zoonotic infection acquired from birds that generally presents with fever, headache, cough and sometimes diarrhea. *E. meningoseptica* is a ubiquitous gram-negative bacterium that characteristically causes meningitis or sepsis in newborns, but can also infect immunocompromized adults.

Figure 17:
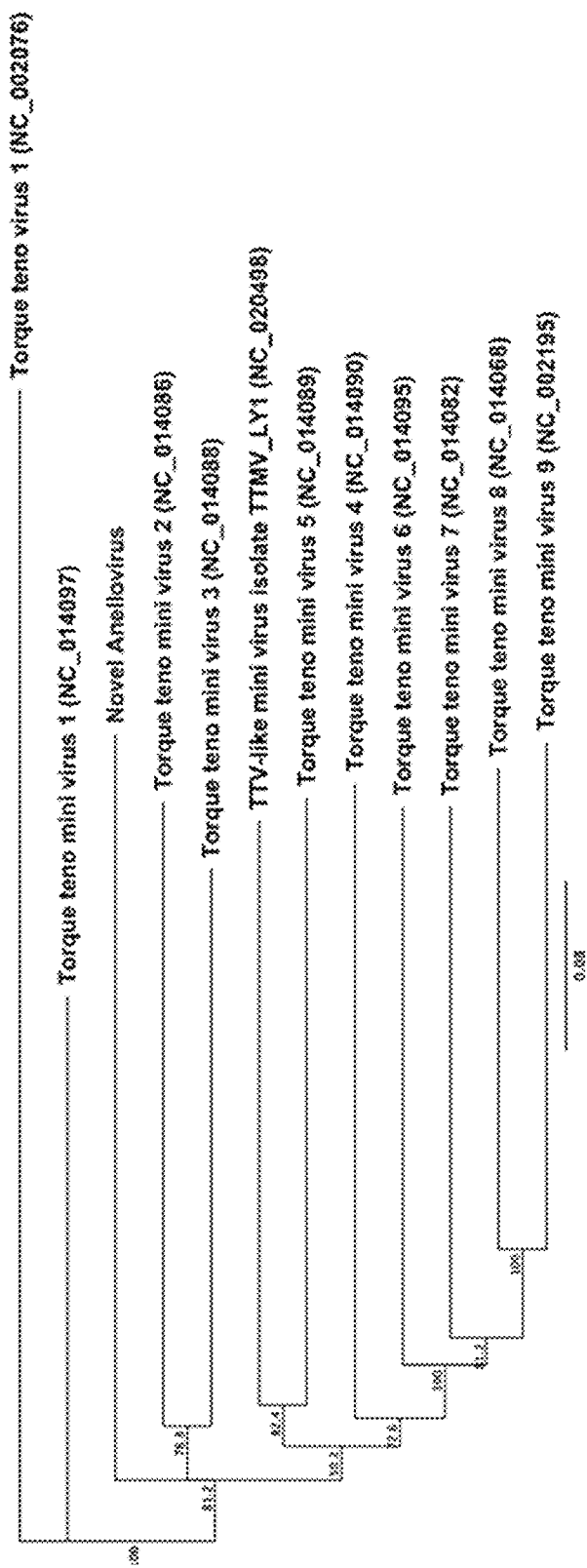
FIG. 17 shows the phylogenetic tree of the consensus sequence of a novel Anellovirus with reference sequences for Torque teno mini viruses, as determined by an embodiment of Taxonomer.

Taxonomer was employed to detect viral infection from a respiratory sample of a child with pneumonia. Reads classified as "viral" or "unknown" were assembled using Trinity (see e.g. Grabherr M G, et al. Nat Biotechnol, 2011 May 15; 29(7):644-52) into 2,325 contigs (run time 6 seconds). Four of the contigs were identified as unclassified members of the family Anelloviridae (FIG. 5B). The consensus genome sequences had 68.5% pairwise identity with TTV-like mini virus isolate LIL-y1 (EF538880.1) and the predicted protein sequences were 44%-60% identical with those of strain LIL-y1. The pie chart and sunburst in FIG. 5B show contig-level classification. Mapping reads back to a manually-constructed viral consensus genome sequence showed 14-fold mean coverage. A phylogenetic tree was constructed using the consensus sequence of the novel Anellovirus (FIG. 5B) with reference sequences for Torque teno mini viruses. Torque teno virus 1 is shown as the outgroup (FIG. 17), demonstrating that Taxonomer is not restricted to short reads, allowing re-analysis of contigs for still greater classification sensitivity. The 239 reads used to generate the annelovirus contigs were analyzed with Afterburner in combination with Protonomer. Consistent with the benchmark data presented in FIG. 9, Protonomer classified 19 of the 239 reads as derived from Anellovirus, whereas Protonomer in combination with Afterburner identified 89 of the 239 reads as derived from Anellovirus. Protonomer did not misclassify any Anellovirus-derived reads, whereas Afterburner misclassified 110 of the Anellovirus-derived reads to other viral taxa.

Figure 9A:
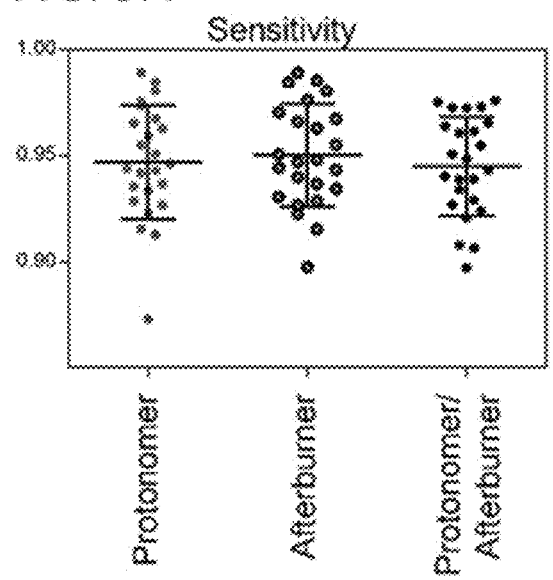
FIGS. 9A-C show relative performances and sensitivities of embodiments of Taxonomer's Protonomer, Afterburner, and the combination of Protonomer/Afterburner.
Figure 9B:
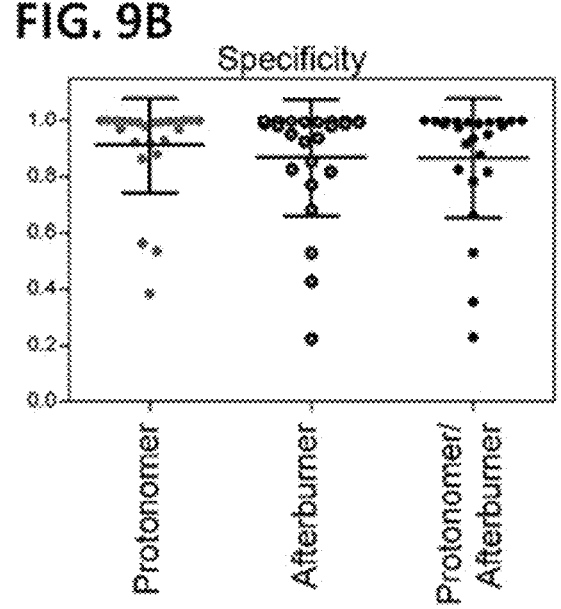
Figure 9C:
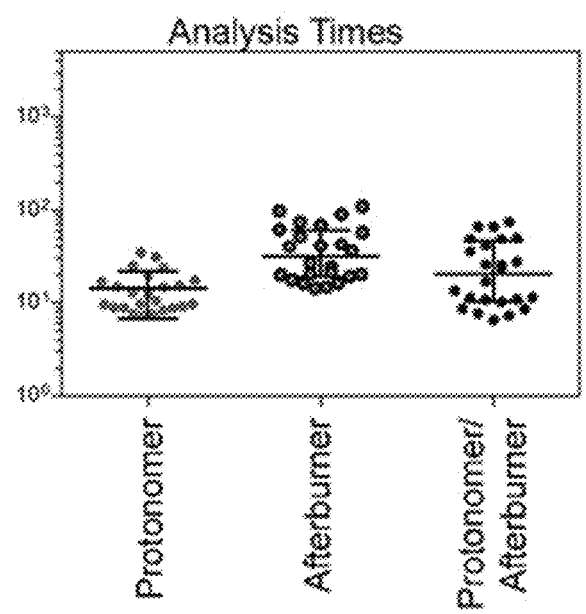

The benchmark data in FIG. 9 shows RNA-Seq data from 23 samples known to harbor respiratory viruses (Table 14; human coronavirus, n=3; Coxsackievirus, n=1; human bocavirus, n=1; human metapneumovirus, n=2; rhinovirus, n=10; parainfluenza virus, n=2; and respiratory syncytial virus, n=4) were binned and the 'viral' and 'unclassified' bins were taxonomically classified by Protonomer, Afterburner, and Protonomer followed by Afterburner analysis of previously unclassified reads (samples as in FIGS. 4A-H, see FIGS. 14A-D and Table 6). FIG. 9A shows that Protonomer (94.6±2.7%) and Afterburner (94.5±2.3%) had comparable sensitivity while their combination was slightly more sensitive (95.0±2.4%). FIG. 9B shows, conversely, that Protonomer (91.1±16.8%) was slightly more specific than Afterburner (86.6±21.4%) and a combination of the two tools (86.8±20.7%). True viral reads were determined by mapping of all reads to a manually constructed viral consensus genome sequence for each sample. FIG. 9C showed the mean analysis times were 14.3±7.5 seconds (Protonomer), 27.4±21.5 seconds (Protomer/Afterburner), and 41.7±28.7 seconds (Afterburner). All tools were run on 16 CPU.

Taxonomer detected highly similar proportions of viral (influenza A from a nasopharyngeal swab) and bacterial (*Mycoplasma pneumonia* from a bronchoalveolar lavage) pathogens in respiratory tract samples subjected to 2 different library preparation methods and 3 different next-generation sequencing platforms (see FIG. 5D and FIG. 20). While the same sequencing libraries were analyzed with the MiSeq and HiSeq instruments, separate sequencing libraries were prepared for the Ion Proton instrument. Similar proportions of viral (0.43% to 0.55% of all reads) and bacterial (16S rRNA sequences representing 0.004% to 0.006% of all reads) pathogen sequences were obtained with all experimental conditions. The presence of both pathogens was confirmed by qPCR. With each of the three platforms, >99% viral reads identified by Taxonomer were classified as influenza A virus. Proportion of bacterial 16S reads identified as *Mycoplasma pneumoniae* were more viriable (MiSeq 69.3%, HiSeq 65.9%, Ion Proton 30.5%). These results demonstrate the versatility of Taxonomer and how it can be used with a variety of sequencing instruments to detect previously missed pathogens and for quality control of expression profiling studies.

Taxonomer was used to detect contamination in a cell culture. RNA-seq data was analyzed from induced pluripotent stem cell cultures with and without *Mycoplasma* contamination. Quality control of the RNA-Seq data by Taxonomer immediately highlighted bacterial contamination (pie chart) and identified the organism as *M. yeatsii* (99.4% sequence identity with the type strain, MYU67946). High expression of rRNA was demonstrated by 32% of RNA-Seq reads mapping to the *M. yeatsii* 16S rRNA gene (245,000× coverage).

Example 10: Taxonomic Classification in Education

Teachers can design genomics related curriculum around taxonomic methods and systems described herein, such as Taxonomer as described in Example 1, to allow students designing experiments, collecting samples and analyzing with Taxonomer. Students collect soil samples, extract DNA/RNA from the soil samples, perform Next Generation Sequencing, then use Taxonmer to analyze taxonomic composition and then compare samples collected from different locations.

Example 11: Taxonomic Classification for Consumers

A consumer can collect sample, either swab from mouth, skin or kitchen sink, seal the sample in a zip bag, mail the sample to a sequencing laboratory, and then analyze the sequencing result online using taxonomic methods and systems described herein, such as Taxonomer as described in Example 1. As a non-limiting example, a dentist can obtain a sample using mouth, tooth, or gum swab to test for mouth or tooth microbes.

Example 12: Taxonomic Classification for Food Safety and Authenticity

Food safety inspectors, food manufacturers, vendors and consumers can check food for contamination by examining microbial content in food, or food authenticity by examining whether food ingredients match the label, using taxonomic methods and systems described herein, such as Taxonomer as described in Example 1. As a non-limiting example, a swab from a food surface or a small piece of the food can be tested.

Example 14: Taxonomic Classification for Hospital Safety and Contamination Monitoring Hospitals and health officials can monitor microbial contamination in hospital equipment, rooms, and patient belongings using taxonomic methods and systems described herein, such as Taxonomer as described in Example 1. As a non-limiting example, a swab from equipment, belongings, wall or floor surface, can be tested for microbial contaminants. As a non-limiting example, such microbial contaminants can be multiple-drug resistant strains of microbes.

Example 15: Taxonomic Classification for Biological Product Quality and Safety Monitoring Inspectors and consumers can monitor microbial contamination in biological products and in biological product manufacturing process using taxonomic methods and systems described herein, such as Taxonomer as described in Example 1. As a non-limiting example, biological products can be tested for microbial contamination. In another non-limiting example, cell lines or other material used for biological product manufacturing processes can be tested for host gene expression profiling, quality monitoring, and microbial contamination.

Example 16: Taxonomic Classification for Animal Disease Diagnostics and Treatment A person involved in animal disease management, such as a veterinary practitioner, a farmer, or a pet owner can diagnose or treat an animal using taxonomic methods and systems described herein, such as Taxonomer as described in Example 1. As non-limiting examples, a mouth swab, blood, a nasalpharyngeal swab, urine, stool, or a swab from a wound site can be collected, sequenced, and analyzed using Taxonomer. The results of the analysis can be used by a veterinary medicine practitioner for diagnostics and treatment plan development.

Example 17: Taxonomic Classification for Microbial Strain Profiling

The taxonomic methods and systems described herein, such as Taxonomer as described in Example 1, can be used to profile microbial strains. A Taxonomer database can be constructed containing microbial strain information (e.g. a bacterial database constructed from different strain, including multiple-drug resistant strains). For example, whole-genome DNA sequences or sequencing reads from multiple strains of one bacterial species can be used for database construction. In another example, sequences of strains can be from a virus, such as HIV, HCV, HBV, and influenza. For such applications, one could use a k-mer subtraction method to identify and retain k-mers that are uniquely diagnostic for a particular node or leaf in the classification database; this approach may be used to remove k-mers that are common to multiple nodes or leaves that frustrate diagnostic efforts. For example, one could specifically produce an antibiotic resistance or virulence factor classification database that allows the unique identification of reads arising from particular resistance markers or virulence factors.

In one embodiment, detecting microbial strain is achieved by calculating the probability that a certain microorganism was in the sample given the probability that one or more of its reference sequences (e.g. 16S, CDSs, etc.) were observed.

First, we can compute the number of times a kmer ($K_i$) is expected to be seen in a given reference sequence tagged by a read due to errors as shown in Eq. 2:

$$|K_{i_{obs\_err}}| = (E_{base} \times L_K \times |NBRS|) \times |reads_{K_{nbrs}}| \quad \text{Eq. 2}$$

Here '|NBRS|' denotes the number of kmers in the database of reference sequences that differ by a single or more nucleotide from $K_i$, $L_k$ is the Kmer length. $E_{base}$ is the per-base error rate of the sequencing platform; and $|reads_{K_{nbrs}}|$ is the number of reads that contain those neighboring kmers.

$$|K_{i_{obs\_err}}|$$

is the number of times $K_i$ would be expected to be observed due to sequencing errors.

Then we can calculate the probability that $K_i$ was actually observed because it was actually in the sample as shown in Eq. 3:

$$pK_{i_{obs}} = 1 - \left(P_{|reads|_{k_i}} \mid |\widehat{K_{i_{obs\_err}}}|\right) \text{ for } |reads_{ki}| > \quad \text{Eq. 3}$$
$$|K_{i_{obs\_err}}| \text{ else } P_{|reads|_{k_i}} == 0$$

where $$1 - \left(P_{|reads|_{k_i}} \mid |\widehat{K_{i_{obs\_err}}}|\right)$$

is the Gaussian expectation of observing |reads| containing $K_i$ solely due to errors.

Then we can calculate the probability that 1 or more of those reads containing $K_i$ originated from reference $Seq_j$ as shown in Eq. 4.

$$pR_{seqj} \mid K_i = \left(1 - \left(\frac{1}{|seqs_{K_i}|}\right)^{|r|}\right). \quad \text{Eq. 4}$$

where $|Seqs_{Ki}|$ is the number of reference sequences in the database that contain $Ki$, and $|r|$ is the number of reads containing $K_i$. In other words, every reference sequence having $K_i$ is equally likely to have given rise to a read containing $K_i$.

The likelihood that reference $Seq_j$ was observed given the probability that each of its k-mers ($K_i$) was observed in the sequence reads, is a recursive conditional probability, as shown in Eq. 5.

$$\text{For all } K_i \text{ in } Seq_j \rightarrow pK_{i_{seqj}} = \left(pK_{i_{obs}} \times [PR_{seqj} \mid K_i]\right) \times pK_{i-1_{seqj}} \quad \text{Eq. 5}$$

The final value of the recursion gives a conditional probability that $Seq_j$ was observed based upon the probability that each of its kmers was observed one or more times in the read dataset: $pSeq_j | \Pi_n^i pK_{i_{seqj}}$ In practice, this formulation can be extended to a collection of ORFs, or other reference sequences, that may comprise a bacterial stereotype, a viral genome, or a bacterial genome, or specific microorganism reference sequences, as shown in Eq. 6.

For all Seq j E collection:

$$p\text{Collection}=\Pi_c^j(pSeq_j | \Pi_n^i pK_{i_{seqj}}) \quad \text{Eq. 6.}$$

Figure 21A:
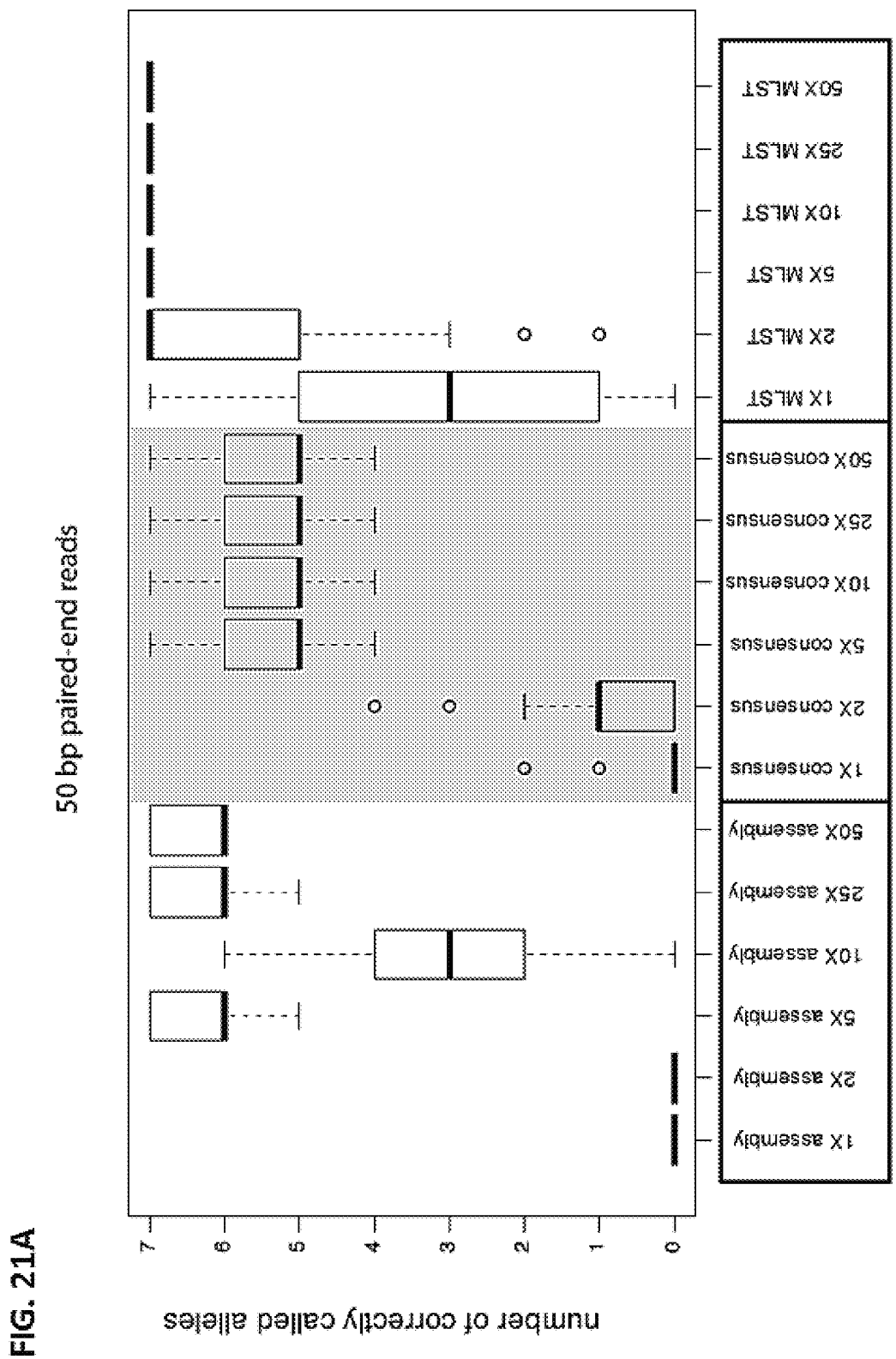
FIGS. 21A-C illustrate results of an example sequence analysis for microbial strain profiling in accordance with embodiments of the disclosure.
Figure 21B:
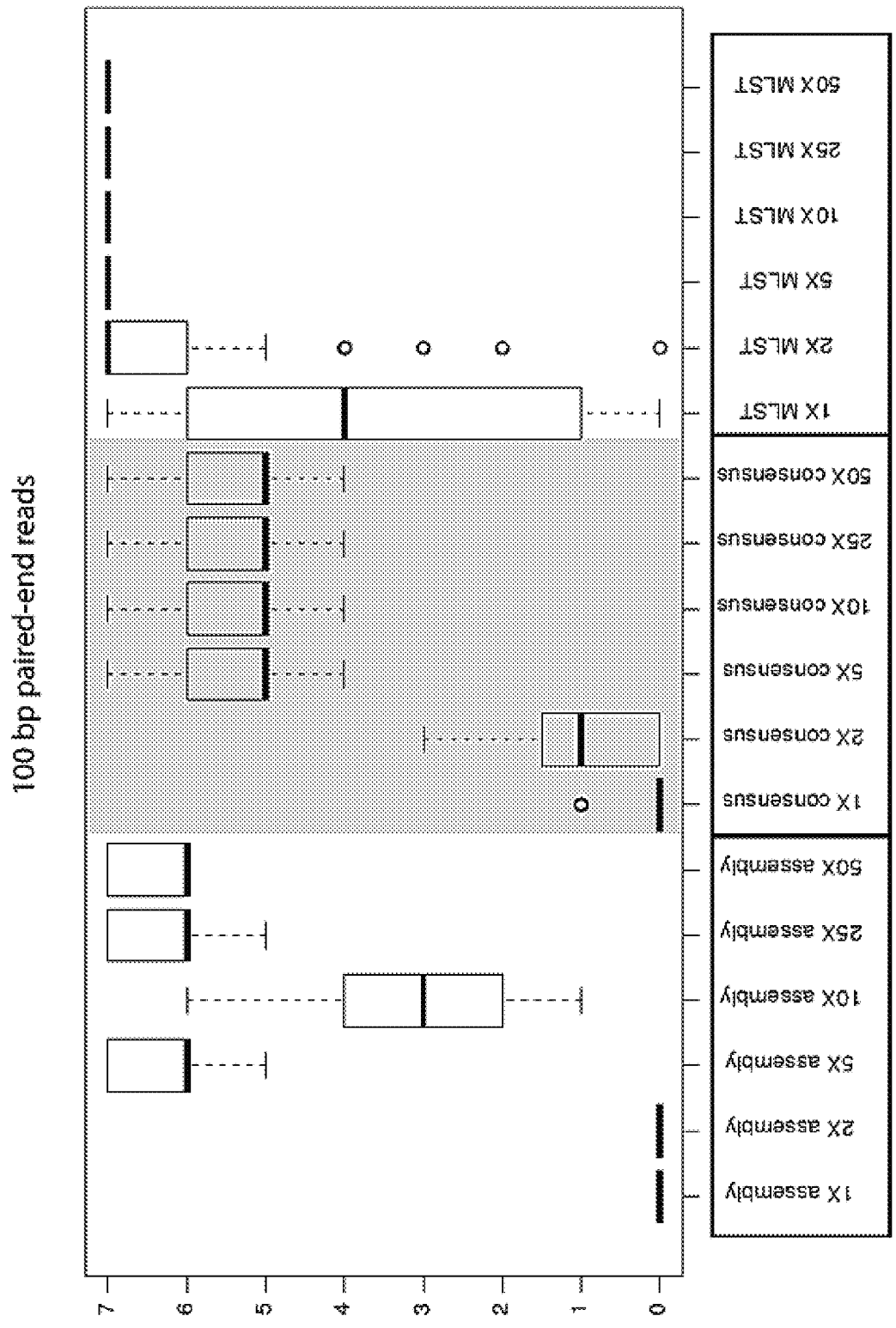
Figure 21C:
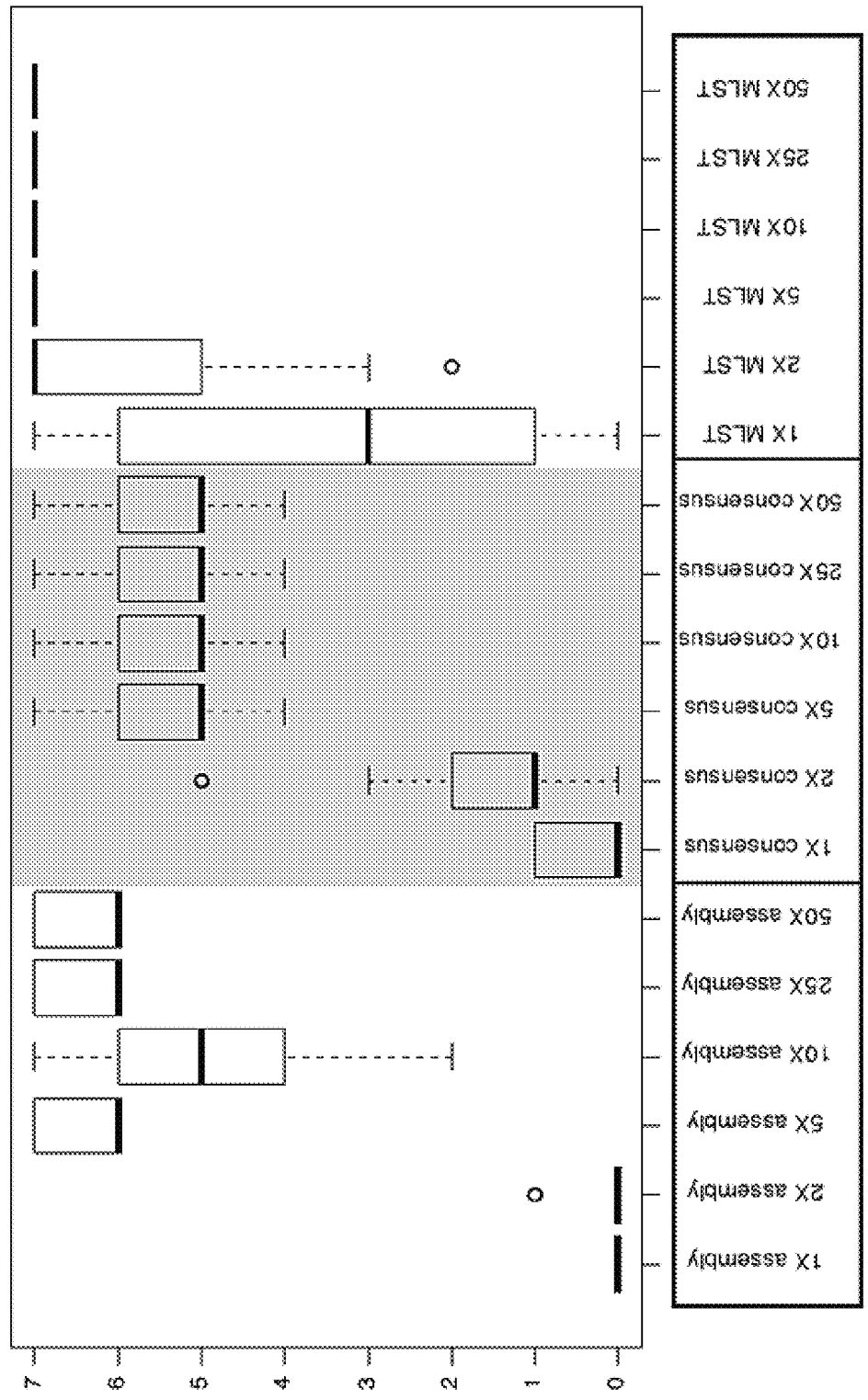

In one example, we applied this approach using sequence information from 7 genetic loci in the *S. pneumonia* genome. Paired-end Illumina sequence reads of 50 (FIG. 21A), 100 (FIG. 21B) and 125 bases (FIG. 21C) in length were simulated using the reference genome with the native Multilocus Sequencing Typing (MLST) loci replaced with randomly chosen, previously observed MLST alleles for each of the 7 loci. This process was repeated for 100 simulated whole genomes under 6 different average levels of genome-wide coverage (1, 2, 5, 10, 25 and 50×). MLST alleles were determined using three methods: (1) de novo assembly ("assembly") in which reads were assembled using the Velvet assembler after which the best allelic match was determined using BLAST to a database of known MLST alleles; (2) Consensus read mapping ("consensus") in which reads were mapped to the R6 reference genome using bwa followed by majority rules consensus base calling at the MLST loci and allelic assignment; and (3) kmer-based MLST typing ("MLST" in FIGS. 21A-C) which catalogues the k-mer content of a read set, determines the probability of their observation and uses a composite likelihood framework to assign the best allele call and composite MLST genotype. Boxplots in FIGS. 21A-C show the number of correctly identified loci using each of the three sequence typing methods and under the 6 different simulated coverage scenarios. The results are stratified by simulated read length with (FIG. 21A) 50 bp reads, (FIG. 21B) 100 bp reads and (FIG. 21C) 125 bp reads.

Figure 22A:
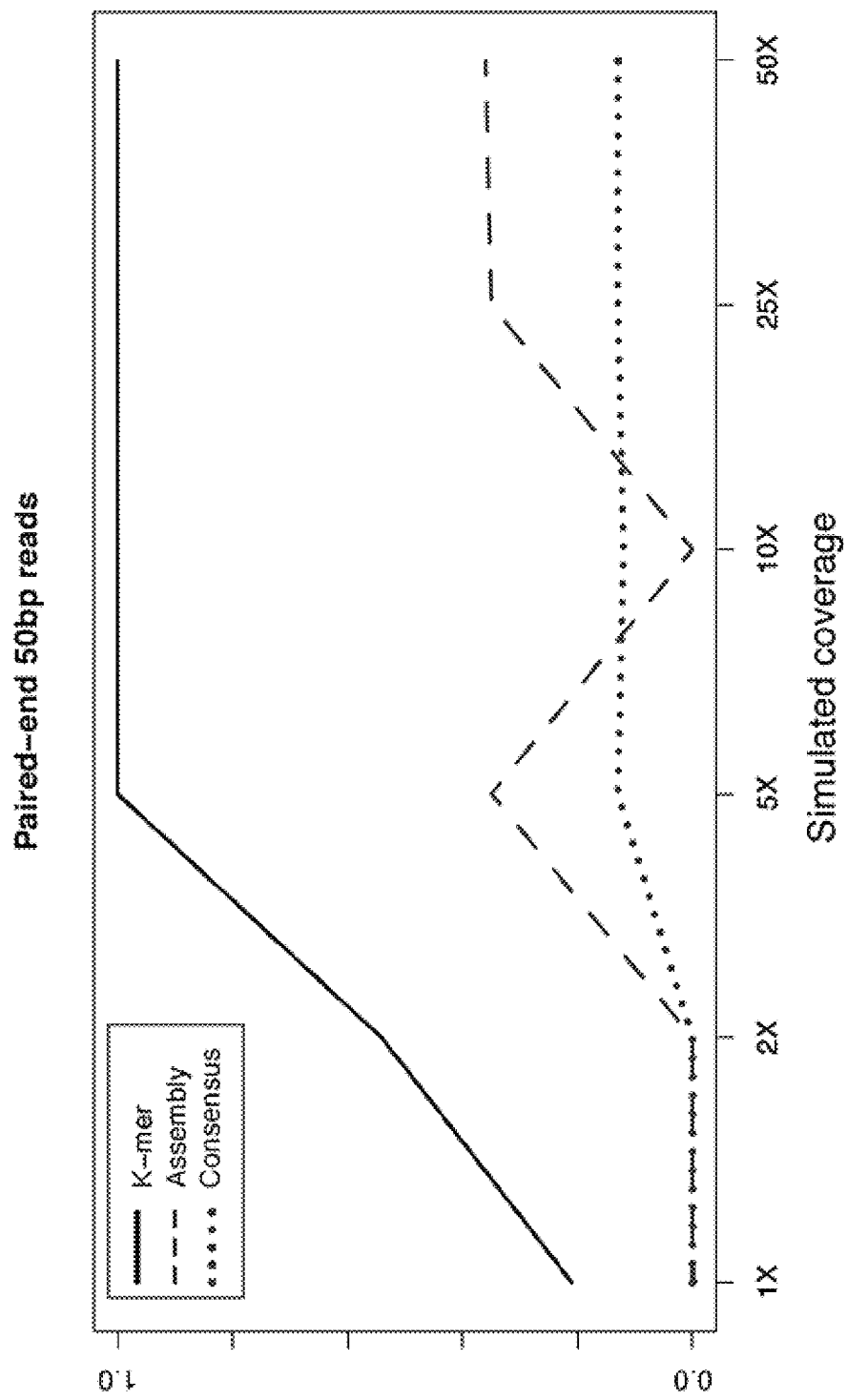
FIGS. 22A-C illustrate results of an example sequence analysis for microbial strain profiling in accordance with embodiments of the disclosure. The y-axis presents the fraction of correctly-typed strains.
Figure 22B:
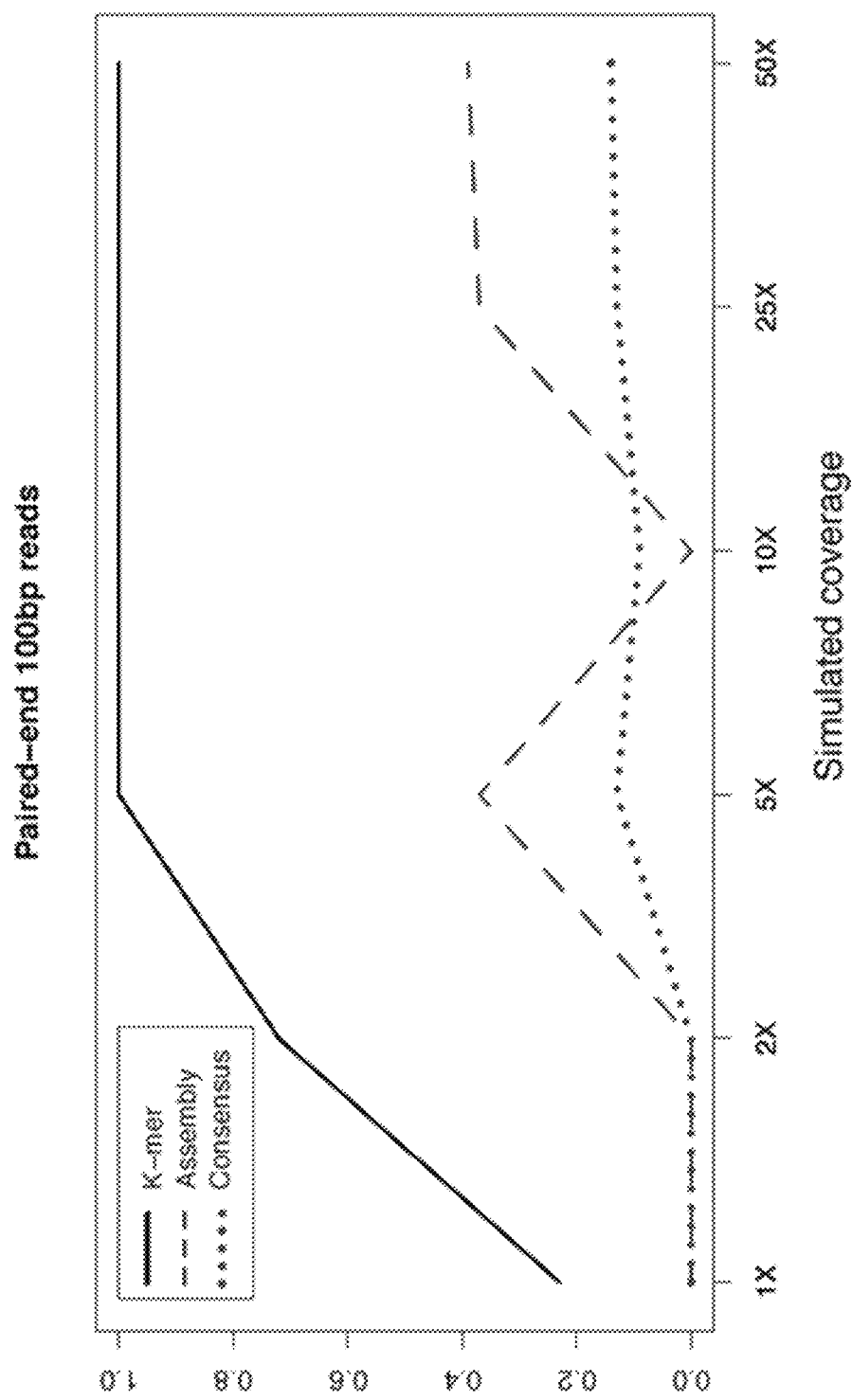
Figure 22C:
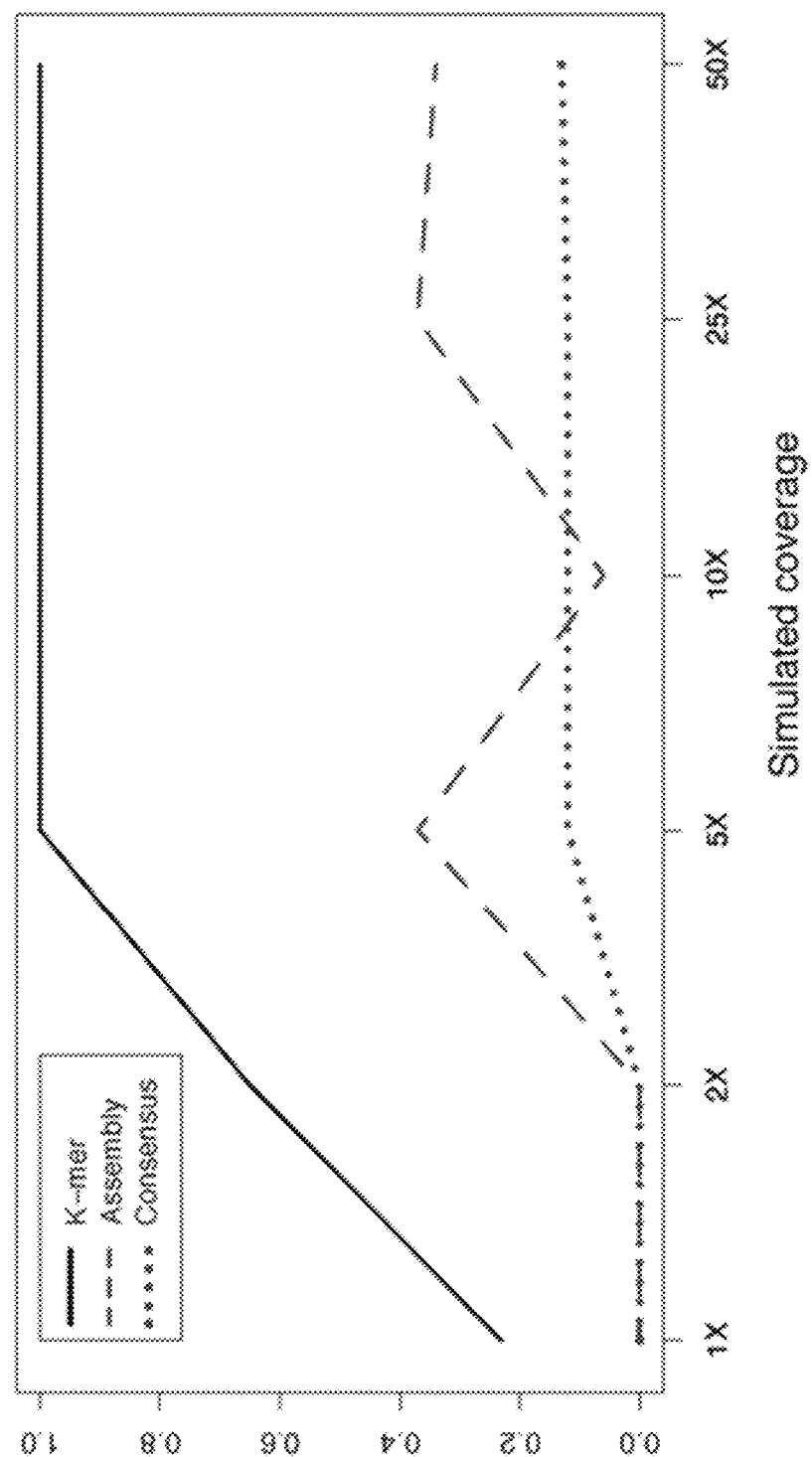

We also show the fraction of correctly MLST genotyped simulated *S. pneumoniae* strains under different coverage scenarios in FIGS. 22A-C. Simulated Illumina reads were generated as in FIGS. 21A-C for 100 *S. pneumoniae* strains. The sequence reads were processed using (1) a k-mer MLST typing pipeline ("K-mer", black), (2) de novo assembly ("Assembly", blue), and (3) read mapping and consensus calling ("Consensus", green) as detailed in FIGS. 21A-C. After determining the allelic composition of each locus using either the composite likelihood approach (1) or finding the BLAST based highest scoring pair (HSP; 2&3), we determined the fraction of correctly identified MLST genotypes under 6 different simulated coverage scenarios from paired-end reads of 50 (FIG. 22A), 100 (FIG. 22B) and 125 (FIG. 22C) bases in length.

In another embodiment, one can determine what organisms are present in a set of query sequences, e.g. sequencing reads from Next Generation Sequencing, given a database of reference sequences of known organisms by summarizing how well an organism's reference sequences are represented by the query sequences into a single score, or rank metric.

This may be achieved in two steps. First, one can k-merize the query sequences, and place the k-mers over the references sequences at the matching locations. Second, for a single organism the dot product is computed between the relative uniqueness of a k-mer location in the reference sequence and the binarized k-mer coverage (where binarized coverage=1 if k-mer coverage>0 and 0 otherwise). K-mer uniqueness is calculated as the fraction of a particular k-mer, $k_i$, in a specific organism compared to the count of $k_i$ in the entire database. For example, if $k_i$ is found 3 times in a particular organism and $k_i$ is counted present 10 times in the database, the uniqueness of $k_i$ in the organism would be 3/10 or 0.3. As an example, suppose a reference sequence contains three k-mers: $k_1$, $k_2$, and $k_3$. These three k-mers have a relative uniqueness of $u_1$, $u_2$, and $u_3$. These k-mers have binarized coverage of $bc_1$, $bc_2$, and $bc_3$. The dot product would then be computed as ($u_1*bc_1+u_2*bc_2+u_3*bc_3$). Next one can calculate the proportion of bases for a single organism's reference sequences that have nonzero coverage compared to the total number of bases in the organism's reference sequences, call this term pi. This information can be summarized using a weighted sum into a single number called the rank metric. Given the weights w1 and w2, we can calculate the rank metric as $w_1*(u_1*bc_1+u_2*bc_2+u_3*bc_3)+w_2*pi$. The rank metric is a condensed summary of how well an organism's reference sequences are represented by the query sequences. The weight is a number between 0 and 1, and the sum of all weights, in this example w1+w2, is 1. In practice, one can use simulation and machine learning methods, e.g. random forests, to compute optimal weights with training data sets or on extensive simulations, and discover rank metric cutoffs that allow making informed calls about which organisms' DNA and/or RNA is present or absent in a given set of query sequences.

In one embodiment, the cutoff of positively identifying an organism is a fixed value. In another embodiment, the cutoff of positively identifying an organism varies depending on the rank metric of other organisms presented in the query sequences. Because of homology or sequence similarity between different organisms, a k-mer from the sequence of one organism can match to sequences of other organisms, therefore a set of k-mers from one organism can generate different rank metrics values to a set of different organisms. The cutoff can be defined to be greater than rank metric values of the set of predefined different organisms.

Example 18: Taxonomic Classification for Tumor Profiling

The taxonomic methods and systems described herein, such as Taxonomer as described in Example 1, can be used to profile tumor-derived DNA. DNA sequences of different tumors from different tissues can be used to construct a tumor database, which can then be used in Taxonomer for analyzing sequences obtained from tumor tissues. Taxonomer can assign each read to a most likely tumor type using a tumor database so constructed. As non-limiting examples, a whole genome assembly or genomic sequence reads can be used for database construction.

Example 19: Taxonomic Classification for Forensic Profiling

The taxonomic methods and systems described herein, such as Taxonomer as described in Example 1, can be used to assign sequencing reads to individual of a population if such database constructed from genomic sequences of individuals from the population. The population used to construct a database, in some examples, people with criminal records, aliens who enter the United States, or the people living in a country. DNA material from a crime scene can be sequenced and analyzed with Taxonomer as described above to determine if a DNA sample derived from an individual is present.

Example 20: Taxonomic Classification for Genetic Testing

The taxonomic methods and systems described herein, such as Taxonomer as described in Example 1, can be used with an artificial k-mer database containing all simulated k-mers with DNA polymorphisms associated with diseases or conditions. Taxonomer can then be used to assign sequencing reads from an individual to particular disease-causing genotypes. The DNA being analyzed with Taxonomer can, as an example, be fetal-derived cell-free DNA from a pregnant woman for prenatal screening, or the DNA can be derived from a mouth swab, saliva, or blood from an individual undergoing genetic testing.

Example 21: Use of k-Mer Weights or Other Measure to Calculate a Pairwise Distance Between Every Sequence in a Classification Database The taxonomic methods and systems described herein, such as Taxonomer as described in Example 1, can be used to calculate a pairwise distance between every sequence in a classification database. Such a pairwise distance can be used to identify sequences with discordant neighbors, thus identifying misannotated or mislocated sequences within a previously existing taxonomy or classification database. The pairwise distances can be used to produce a new phylogenetic tree, having the optimal structure for accurate classification and diagnosis. Bootstrap or other node-confidence metrics can be used to collapse polytomies and poorly resolved nodes in a taxonomic tree, for reasons such as speeding classification, improving classification, or improving diagnostic accuracy. The abovementioned database can be used to classify reference sequences previously annotated as derived from a common clinical strain, isolate, or otherwise named organism as used in diagnostic parlance. This name can be associated with appropriate leaves and nodes of the database in order to associate the taxonomic associations in the database with commonly used diagnostic names for organisms. A similar process can be used to produce a protein database organized by sequence similarity such that the different branches correspond to different types of genes or proteins, such as different functions, GO classifications, gene-families, etc. . . . . Similarly to as described for the nucleotide taxonomic database, the name of the organism the protein(s) are derived from can be attached to the appropriate leaf and node in the protein taxonomy. This approach can be used to distinguish between closely related pathogens, such as *E. coli* and *Shigella* or Anthrax and other Bacilli that cannot be distinguished using 16S sequence alone. For example, other proteins and nucleotide sequences can be used to confirm the presence of a particular pathogen, wherein the presence is indicated by a first piece of data, such as the 16S sequence, and reads are also present that are classified as a taxon-specific protein. These confirmatory findings can be reported to improve a diagnosis. For example, viruses can be classified using the above process to produce a protein database organized upon sequence similarity or pairwise distance such that different branches would correspond to different types of viral genes, such that different branches would correspond to different types of viral genes. Non-limiting examples of these genes can be gag, env, or pol. The names of the viruses from which these sequences are derived can be attached to the appropriate leaves and nodes of the taxonomic structure. The viral database can be used to establish what portion of a viral or viral taxon's genome is present in the query dataset. For example, one could test that HIV was detected in a sample and specifically the sample contain HIV gag and pol sequences, but not HIV env sequences.

Example 22: Effect of Joint Analysis of Mate Pairs on Read Binning

In this example, the effect of joint analysis of mate pairs on read binning using Taxonomer as described in Example 1 is described. Sample 2 from FIG. 18 was analyzed with the 'Binner' module either using only read 1, only read 2, or analyzing both reads jointly after concatenation. Concatenation of mate pairs results in fewer reads with unknown (−13%) and ambiguous bin assignment (−19%) compared to results based on read 1 alone. The largest relative change is seen for phages (+58%), bacteria (+19%), fungi (+18%), and 'Other' (+17%), see Table 18.

TABLE 18

Effect of joint analysis of mate pairs on read binning.

| Bin | Read 1 Reads | % | Read 2 Reads | % | Concatenated Reads | % | Change |
|---|---|---|---|---|---|---|---|
| Human | 1,907,759 | 32.2 | 1,902,495 | 32.1 | 1,944,049 | 32.8 | +2% |
| Bacterial | 952,402 | 16.1 | 953,957 | 16.1 | 1,134,751 | 19.1 | +19% |
| Fungal | 274,232 | 4.6 | 274,800 | 4.6 | 324,874 | 5.5 | +18% |
| Viral | 4,792 | 0.1 | 4,799 | 0.1 | 5,470 | 0.1 | +14% |
| Phage | 1,292 | 0.0 | 1,434 | 0.0 | 2,041 | 0.0 | +58% |
| Ambiguous | 840,208 | 14.2 | 841,933 | 14.2 | 681,413 | 11.5 | −19% |
| Other | 449,774 | 7.6 | 452,366 | 7.6 | 528,242 | 8.9 | +17% |
| Unknown | 1,498,009 | 25.3 | 1,496,761 | 25.2 | 1,308,191 | 22.1 | −13% |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of identifying a presence or an absence of taxa in a sample from a sample source, the method comprising:
(a) obtaining, for each respective k-mer in a plurality of k-mers, for each respective reference polynucleotide sequence ($ref_i$) in a set of reference polynucleotide sequences, a corresponding k-mer weight for the respective k-mer for the respective reference polynucleotide sequence that is a measure of how likely it is that the corresponding k-mer originates from the respective reference polynucleotide sequence, thereby forming a plurality of k-mer weights, wherein each k-mer in the plurality of k-mers has the same length of k nucleotides and wherein k is in a range of 3 to 30;

(b) providing a set of sample sequencing reads for a plurality of polynucleotides from the sample, wherein the set of sample sequencing reads comprises at least 500,000 sample sequencing reads, and wherein each sample sequencing read in the set of sample sequencing reads has a length of 30 nucleotides or more, and for each respective sample sequencing read:
  (i) performing, with a computer system, a sequence comparison between the respective sample sequencing read and the set of reference polynucleotide sequences, wherein the processing comparison comprises determining, for each respective reference polynucleotide sequence in the set of reference polynucleotide sequences, a respective set of k-mers within the respective sample sequencing read that are also found in the respective reference polynucleotide sequence by comparison of each k-mer in the respective sample sequencing read of length k to each respective k-mer in the plurality k-mers; and
  (ii) calculating a respective probability that the respective sample sequencing read corresponds to a particular reference polynucleotide sequence in the set of reference polynucleotide sequences based on the k-mer weights, in the plurality of k-mer weights, for the respective set of k-mers within the sample sequencing read that are also found in the particular reference polynucleotide sequence, thereby generating a respective sequence probability that the respective sample sequencing read matches the particular reference polynucleotide sequence;
(c) calculating one or more scores for the presence or absence of one or more taxa in the sample based on the respective sequence probabilities of each sequencing read in the set of sample sequencing reads; and
(d) identifying a presence or an absence of the taxa based at least in part on the one or more scores.

2. The method of claim 1, wherein the taxa comprise a first bacterial strain identified as present and a second bacterial strain identified as absent based on one or more nucleotide differences in sequence.

3. The method of claim 1, wherein the first bacterial strain is identified as present and the second bacterial strain is identified as absent based on a single nucleotide difference in sequence.

4. The method of claim 1, wherein the set of reference polynucleotide sequences comprises sequences from a plurality of taxa, and a reference polynucleotide sequence in the set of reference polynucleotide sequences is associated with a reference k-mer weight indicative of a likelihood that a reference k-mer within the reference polynucleotide sequence originates from a taxon within the plurality of taxa.

5. The method of claim 1, wherein the performing the sequence comparison is performed for all sequencing reads in parallel.

6. The method of claim 1, further comprising quantifying an amount of a polynucleotide corresponding to the set of reference polynucleotide sequences based on a number of corresponding reference sequencing readings.

7. The method of claim 1, wherein the set of reference polynucleotide sequences comprises reference polynucleotide sequences of one or more of bacteria, archaea, chromalveolata, viruses, fungi, plants, fish, amphibians, reptiles, birds, mammals, and humans.

8. The method of claim 1, wherein the set of reference polynucleotide sequences consists of sequences from a reference individual or a reference sample source.

9. The method of claim 1, wherein the set of reference polynucleotide sequences comprises k-mers having one or more mutations with respect to known polynucleotide sequences, such that a plurality of variants of the known polynucleotide sequences are represented in the set of reference polynucleotide sequences.

10. The method of claim 8, wherein the method further comprises identifying the polynucleotides from the sample source as being derived from the reference individual or the reference sample source.

11. The method of claim 1, wherein the set of reference polynucleotide sequences comprises a plurality of marker gene sequences for taxonomic classification of bacterial sequences.

12. The method of claim 11, wherein the plurality of marker gene sequences comprises 16S rRNA sequences.

13. The method of claim 1, wherein the set of reference polynucleotide sequences comprises sequences of human transcripts, and wherein the performing the sequence comparison comprises determining whether the sample sequencing read is derived from a human subject.

14. The method of claim 1, wherein the set of reference polynucleotide sequences consists of sequences associated with a condition.

15. The method of claim 14, further comprising identifying the sample source as having the condition.

16. The method of claim 1, further comprising identifying a condition of the sample source at least in part based on a comparison of the results of step (d) to a biosignature.

17. The method of claim 16, wherein the condition is contamination.

18. The method of claim 17, wherein the contamination is food contamination, surface contamination, or environmental contamination.

19. The method of claim 16, wherein the condition is infection.

20. The method of claim 19, wherein the biosignature comprises (i) sequences of host transcripts or levels of sequences of host transcripts; and/or (ii) sequences of one or more infectious agents.

21. The method of claim 19, wherein the infection is influenza and the biosignature consists of sequences of one or more of IFIT1, IFI6, IFIT2, ISG15, OASL, IFIT3, NT5C3A, MX2, IFITM1, CXCL10, IFI44L, MX1, IFIH1, OAS2, SAMD9, RSAD2, and DDX58.

22. The method of claim 16, wherein the sample source is a subject.

23. The method of claim 22, further comprising monitoring treatment in an infected subject by identifying the presence or absence of the biosignature in samples from the infected subject at multiple times after beginning treatment.

24. The method of claim 23, further comprising changing treatment of the infected subject based on results of the monitoring.

25. The method of claim 1, wherein the set of reference polynucleotide sequences comprises polynucleotide sequences reverse-translated from amino acid sequences.

26. The method of claim 25, wherein the reverse-translating uses a non-degenerate code comprising a single codon for each amino acid.

27. The method of claim 26, wherein a sequencing read is translated to an amino acid sequence and then reverse-translated using the non-degenerate code prior to comparison with the reverse-translated reference sequences.

28. The method of claim 1, wherein a k-mer weight in the plurality of k-mer weights relates a count of a particular k-mer within a particular reference polynucleotide sequence, a count of the particular k-mer among a group of sequences comprising the reference polynucleotide sequence, and a count of the particular k-mer among all reference polynucleotide sequences in the set of reference polynucleotide sequences.

29. The method of claim 1, wherein a user uploads the set of sequencing reads to the computer system, and the method is performed concurrently with the upload.

30. The method of claim 29, wherein the user uploads the set of sequencing reads to the computer system, and the results of step (d) are reported to the user for one or more of the set of sequencing reads while other sequencing reads of the set of sequencing reads are uploading.

31. The method of claim 29, wherein the computer system is remote with respect to the user.

32. The method of claim 1, further comprising selecting a medical action based on the results of step (b), and optionally performing the medical action.

33. The method of claim 32, wherein the medical action comprises administering a pharmaceutical composition.

34. The method of claim 33, wherein the pharmaceutical composition comprises an antibiotic.

35. The method of claim 1, further comprising assaying the set of polynucleotides to obtain the set of sequencing reads.

36. The method of claim 1, wherein the corresponding k-mer weight for the respective k-mer ($K_i$) for the respective reference polynucleotide sequence ($ref_i$) is calculated as:

$$KWref_i = \frac{C_{ref}(K_i)/C_{db}(K_i)}{C_{db}(K_i)/\text{Total } kmer \text{ count}}$$

wherein,
 $KWref_i$ is the corresponding k-mer weight for the respective k-mer,
 $C_{ref}(K_i)$ is a count of a number of occurrences of the respective k-mer ($K_i$) in the respective reference polynucleotide sequence ($ref_i$),
 $C_{db}(K_i)$ is a count of a number of occurrences of the respective k-mer ($K_i$) in the set of reference polynucleotide sequences, and
 Total kmer count is a number of k-mers of length k-nucleotides in the set of reference polynucleotide sequences.

37. The method of claim 1, wherein the set of reference polynucleotide sequences comprises at least 10 reference polynucleotide sequences.

38. The method of claim 1, wherein the set of reference polynucleotide sequences comprises at least 100000 reference polynucleotide sequences.

39. The method of claim 1, wherein the set of reference polynucleotide sequences comprises at least $1\times10^6$ reference polynucleotide sequences.

40. The method of claim 1, wherein the providing (b) performs the sequence comparison between the respective sample sequencing read and the set of reference polynucleotide sequences at a rate of at least about 500000 sequence comparison per minute.

* * * * *